US012018255B2

(12) United States Patent
Chamberlain et al.

(10) Patent No.: US 12,018,255 B2
(45) Date of Patent: Jun. 25, 2024

(54) COMPOSITIONS AND METHODS FOR TREATING DISORDERS OF GENOMIC IMPRINTING

(71) Applicant: University of Connecticut, Farmington, CT (US)

(72) Inventors: Stormy Chamberlain, Oxford, CT (US); Justin Cotney, Guilford, CT (US); Maéva Langouët, Montreal (CA); Marc Lalande, Palm Harbor, FL (US)

(73) Assignee: University of Connecticut, Farmington, CT (US)

( * ) Notice: Subject to any disclaimer, the term of this patent is extended or adjusted under 35 U.S.C. 154(b) by 740 days.

(21) Appl. No.: 16/770,877

(22) PCT Filed: Dec. 7, 2018

(86) PCT No.: PCT/US2018/064517
§ 371 (c)(1),
(2) Date: Jun. 8, 2020

(87) PCT Pub. No.: WO2019/113472
PCT Pub. Date: Jun. 13, 2019

(65) Prior Publication Data
US 2021/0171943 A1 Jun. 10, 2021

Related U.S. Application Data

(60) Provisional application No. 62/596,397, filed on Dec. 8, 2017.

(51) Int. Cl.
*C07H 21/04* (2006.01)
*C12N 9/22* (2006.01)
*C12N 15/11* (2006.01)
*C12N 15/90* (2006.01)
*A61K 38/00* (2006.01)

(52) U.S. Cl.
CPC .............. *C12N 15/11* (2013.01); *C12N 9/22* (2013.01); *C12N 15/907* (2013.01); *A61K 38/00* (2013.01); *C12N 2310/20* (2017.05); *C12N 2510/00* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 4,554,101 | A | 11/1985 | Hopp |
| 5,580,859 | A | 12/1996 | Felgner et al. |
| 5,679,647 | A | 10/1997 | Carson et al. |
| 5,703,055 | A | 12/1997 | Felgner et al. |
| 9,920,317 | B2 * | 3/2018 | Lee ...................... C12N 15/113 |
| 2005/0244851 | A1 * | 11/2005 | Blume ................. C12Q 1/6876 435/287.2 |
| 2010/0099746 | A1 * | 4/2010 | Yamada .................... A61P 9/10 435/325 |
| 2011/0212058 | A1 * | 9/2011 | Lamond .................. A61P 37/06 435/254.2 |

FOREIGN PATENT DOCUMENTS

| WO | 199324640 A2 | 12/1993 |
|---|---|---|
| WO | 2016170348 A2 | 10/2016 |

OTHER PUBLICATIONS

Peters, Jo. "The role of genomic imprinting in biology and disease: an expanding view." Nature Reviews Genetics 15.8 (2014): 517-530.*
Miotto et al. ("Emerging concept in DNA methylation: role of transcription factors in shaping DNA methylation patterns." Journal of cellular physiology 230.4 (2015): 743-751).*
European Patent Office Extended Search Report for Application No. 18886571.1 dated Aug. 3, 2021 (14 pages).
Angulo, M.A., Butler, M.G. and Cataletto, M.E. (2015) Prader-Willi syndrome: a review of clinical, genetic, and endocrine findings. J Endocrinol Invest, 38, 1249-1263.
Bailey, T.L., Williams, N., Misleh, C., and Li, W.W. (2006). MEME: discovering and analyzing DNA and protein sequence motifs. Nucleic Acids Res 34, W369-373.
Banda, E. and Grabel, L. (2016) Directed Differentiation of Human Embryonic Stem Cells into Neural Progenitors. Methods Mol Biol, 1307, 289-298.
Bressler, J., Tsai, T.F., Wu, M.Y., Tsai, S.F., Ramirez, M.A., Armstrong, D. and Beaudet, A.L. (2001) The SNRPN promoter is not required for genomic imprinting of the Prader-Willi/Angelman domain in mice. Nat. Genet., 28, 232-240.
Buiting, K., Barnicoat, A., Lich, C., Pembrey, M., Malcolm S. and Horsthemke, B. (2001) Disruption of the bipartite imprinting center in a family with Angelman syndrome. Am. J. Hum. Genet., 68, 1290-1294.
Burnett, L.C., LeDuc, C.A., SuJsona, C.R., Paull, D., Rausch, R., Eddiry, S., Carli, J.F .. Morabito, M.V., Skowronski, A.A., Hubner, G. el al. (2017) Deficiency in prohormone convertasc PCI impairs prohormone processing in Prader-Willi syndrome. J. Clin. Invest., 127. 293-305.
Cassidy, S.B., Schwartz, S., Miller, J.L. and Driscoll, D.J. (2012) Prader-Willi syndrome. Genet. Med., 14, 10-26.
Castle, J.C., Armour, C.D., Lower, M., Haynor, D., Biery, M .. Bouzck, H., Chen, R., Jackson, S., Johnson, J.M., Rohl, C.A. el al. (2010) Digital genome-wide ncRNA expression, including SnoRNAs, across 11 human tissues using polyA-neutral amplification. PLoS One, 5, el 1779.

(Continued)

*Primary Examiner* — Kimberly Chong
(74) *Attorney, Agent, or Firm* — Michael Best & Friedrich LLP

(57) ABSTRACT

Disclosed herein are compositions, kits, and methods for treating a disorder of genomic imprinting in a subject. The method may include modifying a zinc-finger protein 274 (ZNF274) binding site on maternal chromosome 15 at position 15q11-q13 of the subject, such that the binding of a ZNF274 protein to the ZNF274 binding site is reduced relative to a control. The ZNF274 binding site comprises a polynucleotide having at least 90% sequence identify to SEQ ID NO: 1 or SEQ ID NO: 42. Further provided are DNA targeting systems that bind to a ZNF274 binding site or to a gene encoding a ZNF274 protein.

6 Claims, 25 Drawing Sheets

Specification includes a Sequence Listing.

(56) References Cited

OTHER PUBLICATIONS

Cavaille, J., Buiting, K., Kiefmann, M., Lalande, M., Branna, C.I., Horstbemke, B., Bachellerie, J.P., Brosius, J. and Huttenhofer, A. (2000) Identification of brain-specific and imprinted small nucleolar RNA genes exhibiting an unusual genomic organization. Proc Natl Acad Sci USA, 97, 14311-14316.
Chamberlain, S.J. and Lalande, M. (2010) Angelman syndrome, a genomic imprinting disorder of the brain. J Neurosci., 30, 9958-9963.
Chamberlain, SJ., Chen, P.F., Ng, K.Y., Bourgois-Rocha, F., Lemtiri-Chlich, F., Levine, E.S. and Lalande, M. (2010) Induced pluripotent stem cell models of the genomic imprinting disorders Angelman and Prader-Willi syndromes. PNAS Early Edition, 1-6.
Chen, P.F., Hsiao, U.S., Sirois, C.L. and Chamberlain, SJ. (2016) RBFOXI and RBFOX2 are dispensable in iPSCs and iPSC-derived neurons and do not contribute to neural-specific paternal UBE3A silencing. Sci Rep, 6, 25368.
Clayton-Smith, J. and Laan, L. (2003) Angelman syndrome: a review of the clinical and genetic aspects. J. Med. Genet., 40, 87-95.
Cotney, J.L. and Noonan, J.P. (2015) Chromatin immunoprecipitation with fixed animal tissues and preparation for high-throughput sequencing. Cold Spring Harb Protoc, 2015, 191-199.
Cruvinel, E., Budinetz, T., Gennain, N., Chamberlain, S., Lalande, M. and Martins-Taylor, K. (2014) Reactivation of maternal SNORD116 cluster via SETDB1 knockdown in Prader-Willi syndrome iPSCs. Hum. Mol. Genet., 23, 4674-4685.
Dittrich, B., Buiting, K., Korn, B., Rickard, S., Buxton, J., Saitoh, S., Nicholls, R.D., Poustka, A., Winterpacbt, A., Zabel, B. et al. (1996) Imprint switching on human chromosome 15 may involve alternative transcripts of the SNRPN gene. Nat. Genet., 14, 163-170.
Doege. C.A., Inoue, K., Yamashita, T., Rhee, D.B., Travis, S., Fujita. R., Guarnieri, P., Bhagat, G., Vanti, W.B., Shih, A. et al. (2012) Early-stage epigenetic modification during somatic cell reprogranuning by Parpl and Tet2. Nature, 488. 652-655.
Donnelly et al., "DNA Vaccines," Ann. Rev. Immunol. 1997, 15, 617-648.
DuBose, A.J., Smith, E.Y., Johnstone, KA. and Resnick, J.L. (2012) Temporal and developmental requirements for the Prader-Willi imprinting center. Proc Natl Acad Sci USA, 109, 3446-3450.
Farber, C., Dittrich, B., Buiting, K. and Horsthemke, B. (1999) The chromosome 15 imprinting centre (IC) region has undergone multiple duplication events and contains an upstream exon of SNRPN that is deleted in all Angelman syndrome patients with an IC microdeletion. Hum. Mol. Genet., 8, 337-343.
Ficz, G., Branco, M.R., Seisenberger, S., Santos, F., Krueger, F., Hore, T.A., Marques, CJ., Andrews, S. and Reik, W. (2011) Dynamic regulation of 5-hydroxymethylcytosine in mouse ES cells and during differentiation. Nature, 473, 398-402.
Frietze, S., O'Geen, H., Blahnik, K.R., Jin, V.X. and Farnham, P.J. (2010) ZNF274 recruits the histone methyltransfcrase SETDB1 to the 3' ends of ZNF genes. PLoS One, 5, e15082.
Germain, N.D., Banda, E.C., Becker, S., Naegele, J.R. and Grabel, L.B. (2013) Derivation and isolation of NKX2.1-positive basal forebrain progenitors from human embryonic stem cells. Stem Cells Dev, 22, 1477-1489.
Germain, N.D., Chen, P.F., Plocik, A.M., Glatt-Deeley, H., Brown, J., Fink, J.J., Bolduc, KA., Robinson, T.M., Levine, E.S., Reiter, L.T. et al. (2014) Gene expression analysis of human induced pluripotent stem cell-derived neurons carrying copy number variants of chromosome 15q11-q13.1. Mol Autism, 5, 44.
Grant, C.E., Bailey, T.L., and Noble, W.S. (2011). FIMO: scanning for occurrences of a given motif. Bioinformatics 27, 1017-1018.
Heagerty et al., "Time-Dependent ROC Curves for Censored Survival Data and a Diagnostic Marker," Biometrics 2000, 56, 337-44.
Imbeault, M., Helleboid, P.Y. and Trono, D. (2017) KRAB zinc-finger proteins contribute to the evolution of gene regulatory networks. Nature, 543, 550-554.
Johnstone, K.A .. DuBose, A.J., Futtner, C.R., Elmore, M.D., Brannan, C.I. and Resnick, J.L. (2006) A human imprinting centre demonstrates conserved acquisition but diverged maintenance of imprinting in a mouse model for Angolman syndrome imprinting defects. Hum. Mol. Genet., 15, 393-404.
Kim, Y., Lee, H.M., Xiong, Y., Sciaky, N., Hulbert, S.W., Cao, X., Everitt, J.I., Jin, J., Roth, B.L. and Jiang, Y.H. (2017) Targeting the histone methyltransferase G9a activates imprinted genes and improves survival of a mouse model of Prader-Willi syndrome. Nat. Med., 23(2):213-222.
Kyte et al., "A Simple Method for Displaying the Hydropathic Character of a Protein," J. Mol. Biol. 1982, 157, 105-132.
Landers. M., Bancescu, D.L., Le Meur, E., Rougeulle, C., Glatt-Deeley, H., Brannan, C., Muscatclli, F. and Lalande, M. (2004) Regulation of the large (approximately 1000 kb) imprinted murine Ube3a antisense transcript by alternative exons upstream of Snurf/Snrpn. Nucleic Acids Res., 32, 3480-3492.
Langouet et al., "Zinc finger protein 274 regulates imprinted expression of transcripts in Prader-Willi syndrome neurons" Human Molecular Genetics, (Advance Access Publication Date: Dec. 7, 2017) 27(3):505-515.
Lewis, M.W., Brant, J.O., Kramer, J.M., Moss, J.I., Yang, T.P., Hansen, P.J., Williams, RS. and Resnick, J.L. (2015) Angelman syndrome imprinting center encodes a transcriptional promoter. Proc Natl Acad Sci USA, 112, 6871-6875.
Martins-Taylor, K., Hsiao, J.S., Chen, P.F., Glatt-Deeley, H., De Smith, A.J., Blakemore, A.J., Lalande, M. and Chamberlain, S.J. (2014) Imprinted expression of UBE3A in non-neuronal cells from a Prader-Willi syndrome patient with an atypical deletion. Hum. Mol. Genet., 23, 2364-2373.
Martins-Taylor, K., Schroeder, D.I., LaSalle, J.M., Lalande, M. and Xu, R.H. (2012) Role of DNMT3B in the regulation of early neural and neural crest specifiers. Epigenetics, 7, 71-82.
Meng, L., Person, R.E. and Beaudet, A.L. (2012) Ube3a-ATS is an atypical RNA polymerase II transcript that represses the paternal expression of Ube3a. Hum. Mol. Genet., 21, 3001-3012.
Numata, K., Kohama, C., Abe, K. and Kiyosawa, H. (2011) Highly parallel SNP genotyping reveals high-resolution landscape of mono-allelic Ube3a expression associated with locus-wide antisense transcription. Nucleic Acids Res., 39, 2649-2657.
Ohta, T., Gray, T.A., Rogan, P.K., Buiting, K., Gabriel, J.M., Saitoh, S., Muralidhar, B., Bilienska, B., Krajcwska-Walasck, M., Driscoll, D.J. et al. (1999) Imprinting-mutation mechanisms in Prader-Willi syndrome. Am. J. Hum. Genet., 64, 397-413.
Polex-Wolf, J., Yeo, G.S. and O'Rabilly, S. (2017) Impaired prohormone processing: a grand unified theory for features of Prader-Willi syndrome? J. Clin. Invest., 127, 98-99.
Powell, W.T., Coulson, R.L., Crary, F.K., Wong, S.S., Ach, R.A., Tsang, P., Alice Yamada, N., Yasui, D.H. and Lasalle, J.M. (2013) A Prader-Willi locus lncRNA cloud modulates diurnal genes and energy expenditure. Hum. Mol. Genet., 22, 4318-4328.
Rodriguez-Jato, S., Nicholls, R.D., Driscoll, DJ. and Yang, T.P. (2005) Characterization of cis- and trans-acting elements in the imprinted hunan SNURF-SNRPN locus. Nucleic Acids Res., 33, 4740-4753.
Rougeulle, C., Cardoso, C., Fontes, M., Collcaux, L. and Lalande, M. (1998) An imprinted antisense RNA overlaps UBE3A and a second maternally expressed transcript. Nat. Genet., 19, 15-16.
Runte, M., Huttenhofer, A., Gross, S., Kiefmann, M., Horsthemke, B. and Buiting, K. (2001) The IC-SNURF-SNRPN transcript serves as a host for multiple small nucleolar RNA species and as an antisense RNA for UBE3A. Hum. Mol. Genet., 10, 2687-2700.
Sanjana, N.E., Shalem, O. and Zhang, F. (2014) Improved vectors and genome-wide Libraries for CRISPR screening. Nat. Methods, 11, 783-784.
Shalem, O., Sanjana, N.E., Hartenian, E., Shi, X., Scott, D.A., Mikkelsen, T.S., Heckl, D., Ebert, B.L., Root, D.E., Doench, J.G. et al. (2014) Genome-scale CRISPR-Cas9 knockout screening in human cells. Science, 343, 84-87.
Shemer, R., Hershko, A.Y., Perk, J., Mostoslavsky, R., Tsuberi, B., Cedar, H., Buiting, K. and Razin, A. (2000) The imprinting box of the Prader-Willi/Angelman syndrome domain. Nat. Genet, 26, 440-443.

(56) References Cited

OTHER PUBLICATIONS

Sutcliffe, J.S., Nakao, M., Christian, S., Orstavik, K.H., Tommerup, N., Ledbetter, D.H. and Beaudet, AL. (1994) Deletions of a differentially methylated CpG island at the SNRPN gene define a putative imprinting control region. Nat. Genet., 8, 52-58.

Valle-Garcia, D., Qadeer, Z.A., McHugh, D.S., Ghiraldini, F.G., Chowdhury, A.H., Hasson, D., Dyer, M.A., Recillas-Targa, F. and Bernstein, E. (2016) ATRX binds to atypical chromatin domains at the 3' exons of zinc finger genes to preserve H3K9me3 enrichment. Epigenetics, 11, 398-414.

Wawrzik, M., Spiess, A.N., Herrmann, R., Buiting, K. and Horsthemke, B. (2009) Expression of SNURF-SNRPN upstream transcripts and epigenetic regulatory genes during human spermatogenesis. Eur J Hum Genet, 17, 1463-1470.

Williams, C.A., Lossie, A., Driscoll, D. and Unit, R.C.P. (2001) Angelman syndrome: mimicking conditions and phenotypes. Am J Med Genet, 101, 59-64.

Witzgall, R., O'Leary, E., Leaf, A., Onaldi, D. and Bonventre, J.V. (1994) The Kruppel-associated box-A (KRAB-A) domain of zinc finger proteins mediates transcriptional repression. Proc Natl Acad Sci USA, 91, 4514-4518.

Wu, M.Y., Jiang, M., Zhai, X., Beaudet, A.L. and Wu, R.C. (2012) An unexpected function of the Prader-Willi syndrome imprinting center in maternal imprinting in mice. PLoS One, 7, e34348.

Zeschnigk, M., Schmitz, B., Dittrich, B., Buiting, K., Horsthemke, B. and Doerfler, W. (1997) Imprinted segments in the human genome: different DNA methylation patterns in the Prader-Willi/Angelman syndrome region as determined by the genomic sequencing method. Hum. Mol. Genet., 6, 387-395.

International Search Report and Written Opinion for Application No. PCT/US2018/064517 dated May 7, 2019 (17 pages).

International Preliminary Report on Patentability for Application No. PCT/US2018/064517 dated Jun. 18, 2020 (9 pages).

Japanese Patent Office Action for application 2020-550047, mailed on Nov. 14, 2022 (6 pages with translation).

\* cited by examiner

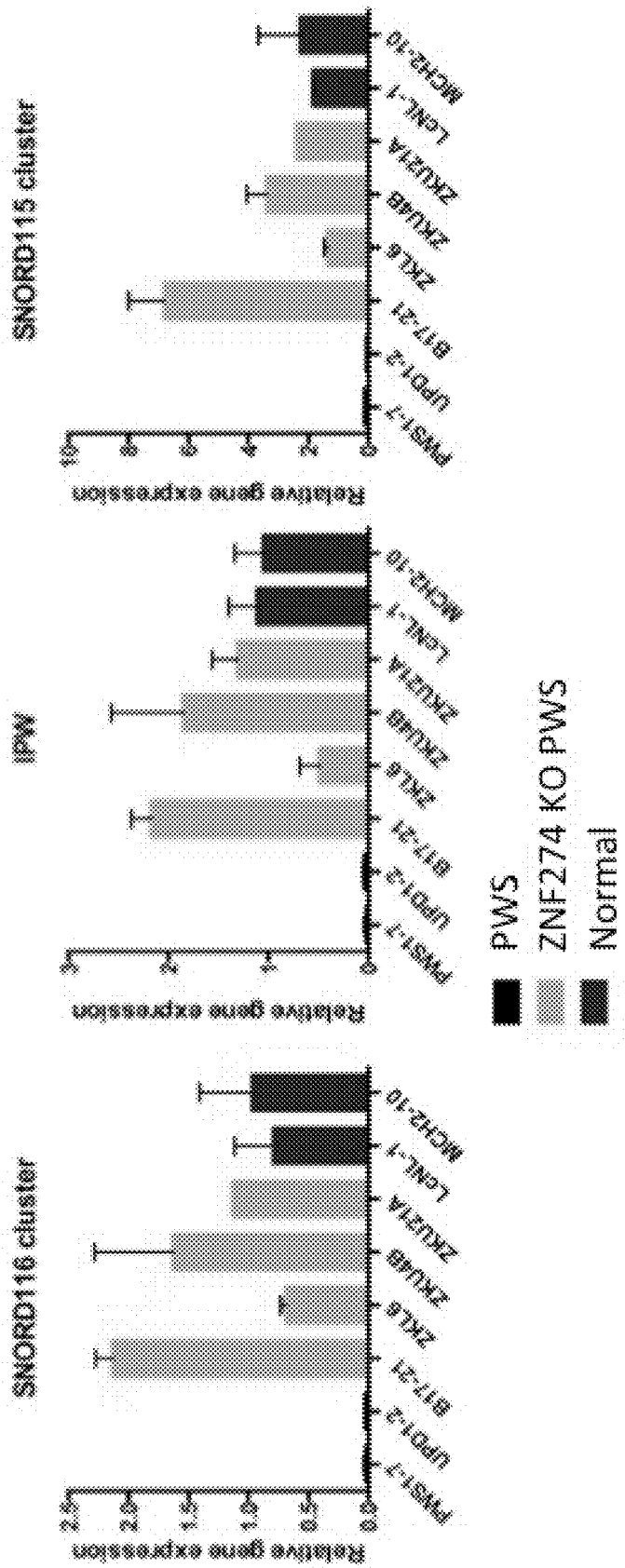

COMPOSITIONS AND METHODS FOR TREATING DISORDERS OF GENOMIC IMPRINTING

CROSS-REFERENCE TO RELATED APPLICATIONS

This patent application is the U.S. national stage entry, under 35 U.S.C. § 371, of International Application Number PCT/US2018/064517, filed Dec. 7, 2018, which claims priority to U.S. Provisional Application No. 62/596,397, filed Dec. 8, 2017, the entire contents of each of which are incorporated herein by reference.

FIELD

This disclosure relates to compositions and methods for treating genetic diseases such as disorders of genomic imprinting.

SEQUENCE LISTING

The instant application contains a Sequence Listing which has been submitted electronically in ASCII format and is hereby incorporated by reference in its entirety. Said ASCII copy, created on Dec. 7, 2018 is named "209670-9024-WO01 Sequence Listing" and is 9,816 bytes in size.

INTRODUCTION

Prader-Willi syndrome (PWS) is a genetic disorder that affects 1 in 10,000 to 30,000 people and maps to chromosome 15. It is characterized by neonatal hypotonia, and later in development, hyperphagia and consequent obesity as well as obsessive-compulsive behaviors and temper tantrums. Through a normal process called genomic imprinting, the chromosome 15 that is inherited from the father has a set of genes that are switched on while the same set of genes on the chromosome 15 inherited from the mother are switched off. In Prader-Willi syndrome (PWS), there is no normal copy of the paternal chromosome 15, so patients only have the silent copies inherited from the mother. PWS is a disorder of genomic imprinting, an epigenetic process by which the chromosome 15 that is inherited from the father has a set of genes that are transcriptionally active while the same set of genes on the chromosome 15 inherited from the mother are transcriptionally silenced. In PWS, there is no normal copy of the paternal chromosome 15, so patients only have the silent copies inherited from the mother.

PWS diagnosis can be confirmed within the first week of life by using a widespread diagnostic test based on DNA methylation. The DNA methylation test is prescribed for all newborns displaying hypotonia or developmental delay. As a result, new cases of PWS are frequently diagnosed early in the prenatal period. Most individuals with PWS display a growth hormone deficiency. Recombinant human growth hormone (HGH) therapy has been used since 2000 with several benefits including increased height and muscle mass and decreased body fat. HGH therapy involves daily subcutaneous injections and, despite some therapeutic benefit, there remains a major obstacle in controlling food intake in PWS adolescents and adults. There are also drugs to treat PWS features such as daytime sleepiness, and there is a clinical trial for control of hyperphagia with oxytocin. The behavioral and psychiatric abnormalities associated with PWS remain a major therapeutic challenge. There is currently no cure for PWS and no current therapeutic strategies for activating the silenced maternal RNA transcripts at the PWS locus. Thus, there remains an unmet need for an effective treatment for PWS and its several manifestations.

SUMMARY

The present disclosure relates to a guide RNA (gRNA) molecule comprising a polynucleotides sequence corresponding to SEQ ID NO: 13, SEQ ID NO: 14, SEQ ID NO: 43, SEQ ID NO: 44, SEQ ID NO: 45, SEQ ID NO: 46, SEQ ID NO: 47, SEQ ID NO: 48 or SEQ ID NO: 48.

The present disclosure also relates to a DNA targeting system that binds to a ZNF274 binding site. The DNA targeting system comprises at least one gRNA that binds and targets a polynucleotide sequence comprising a nucleotide sequence corresponding to at least one of SEQ ID NO: 1, SEQ ID NO: 42, SEQ ID NO: 43, SEQ ID NO: 44, SEQ ID NO: 45, SEQ ID NO: 46, or variant thereof.

The present disclosure further relates to a DNA targeting system that binds to a gene encoding a ZNF274 protein. The DNA targeting system comprises at least one gRNA that binds and targets a polynucleotide sequence comprising a nucleotide sequence corresponding to at least one of SEQ ID NO: 13, SEQ ID NO: 14, SEQ ID NO: 16, SEQ ID NO: 17, SEQ ID NO: 47, SEQ ID NO: 48, or variant thereof.

The present disclosure further relates to an isolated polynucleotide sequence comprising the gRNA molecule described above.

The present disclosure further relates to an isolated polynucleotide sequence encoding the DNA targeting system described above.

The present disclosure further relates to a vector comprising the isolated polynucleotide sequence described above.

The present disclosure further relates to a vector encoding the gRNA molecule described above and a Clustered Regularly Interspaced Short Palindromic Repeats associated (Cas) protein.

The present disclosure further relates to a cell comprising the gRNA described above, the DNA targeting system described above, the isolated polynucleotide sequence described above, the vector described above, or a combination thereof.

The present disclosure further relates to a kit comprising the gRNA described above, the DNA targeting system described above, the isolated polynucleotide sequence described above, the vector described above, the cell described above, or a combination thereof.

The present disclosure further relates to a pharmaceutical composition comprising the gRNA described above, the DNA targeting system described above, the isolated polynucleotide sequence described above, the vector described above, the cell described above, or a combination thereof.

The present disclosure further relates to a method for treating a disorder of genomic imprinting in a subject. The method comprises: modifying a zinc-finger protein 274 (ZNF274) binding site on maternal chromosome 15 at position 15q11-q13 of the subject, such that the binding of a ZNF274 protein to the ZNF274 binding site is reduced relative to a control, wherein the ZNF274 binding site comprises a polynucleotide having at least 90% sequence identity to SEQ ID NO: 1 or SEQ ID NO: 42.

The present disclosure further relates to a method for treating a disorder of genomic imprinting in a subject. The method comprises: administering to the subject a pharmaceutically effective amount of an agent that reduces the interaction of a ZNF274 protein with a ZNF274 binding site on maternal chromosome 15 at position 15q11-q13 of the subject relative to a control, wherein the ZNF274 binding site comprises a polynucleotide having at least 90% sequence identity to SEQ ID NO: 1 or SEQ ID NO: 42.

The present disclosure further relates to a formulation for treating a disorder of genomic imprinting in a subject. The formulation comprises an agent that reduces relative to a control the binding of a ZNF274 protein to a ZNF274 binding site on a maternal nucleotide sequence, the ZNF274 binding site comprising a polynucleotide having at least 90% sequence identity to SEQ ID NO: 1 or SEQ ID NO: 42.

The disclosure provides for other aspects and embodiments that will be apparent in light of the following detailed description and accompanying Figures.

BRIEF DESCRIPTION OF THE DRAWINGS

(FIG. 1A) Simplified genetic and allelic expression map of 15q11.2-q13. Active and inactive (repressed) transcripts are denoted by open and closed boxes, respectively. Arrows indicate the direction of transcription. A solid black line represents paternal SNURF/SNRPN transcripts expressed in most cell types, whereas a dashed black line indicates neuron-specific transcripts, including upstream exons of SNRPN and UBE3A-ATS. UBE3A is maternally expressed in neurons whereas other genes are only paternally expressed in all cell types. The PWS-IC is denoted by the black (methylated)/white (unmethylated) circle. Orange dashes under the SNORD116 cluster represent the six ZNF274 binding sites within the SNORN116s classified as Group 1 (SNOG1-BS1 to SNOG1-BS6). (FIG. 1B) ChIP assay for ZNF274 in iPSCs. Here and in subsequent figures, PWS patient lines are shown in black, their corresponding ZNF274 KO lines in green, control (CTRL) cell lines in blue and AS, used as a negative control, in white. Here and in subsequent figures, quantification of ChIP was performed and calculated as percent input for each sample. Binding at ZNF180, a previously reported ZNF274 binding site associated with high levels of H3K9mc3 signal, was used as a positive control and, for each line, all other binding sites were normalized to this one. The PWS parental line was set as 1 for each panel and relative normalization to this positive sample was done for each cell line. A minimum of 2 biological replicates per cell line were performed. Significance was calculated using two-way analysis of variance (ANOVA) test with a Dunnett post-test to compare the two large deletion (LD) KOs to PWS LD and the three UPD KOs to PWS UPD. Here and in subsequent figures, *P<0.05, P<0.01, *P<0.001, ****P<0.0001. (FIG. 1C) ChIP assay for the repressive histone modification H3K9me3 in iPSCs. The same color code as in FIG. 1B is used for AS, CTRLs, PWS, and ZNF274 KO cell lines.

FIG. 2A) Gene expression of the SNRPN U exons (U4/ex2), (FIG. 2B) SNRPN major promoter (ex 1/2), and (FIG. 2C) SNRPN mRNA (cx3/4) in iPSCs. The same color code as in FIG. 1B is used. Here and in subsequent figures, gene expression was assessed using the comparative CT method, GAPDH was used as an endogenous control. Data were normalized to CTRL1 for each panel and plotted as the mean with Standard Deviation (SD). A minimum of 3 biological replicates per cell line were performed. Significance was calculated using one-way analysis of variance (ANOVA) test with a Dunnett post-test to compare the two LD KOs to PWS LD and the three UPD KOs to PWS UPD. (FIG. 2D) DNA methylation level at the PWS-IC in iPSCs was evaluated using a quantitative restriction endonuclease assay (EpiMark 5hmC and 5mC Analysis Kit) that measures the relative levels of 5-methylcytosine (5mC), 5-hydroxymethylcytosine (5hmC), and unmodified cytosine (C). As expected, CTRL iPSCs show approximately equal levels of 5mC and Cat the PWS-IC whereas PWS LD and AS iPSCs display respectively, almost complete (5mC) and almost no (C) methylation. Although a slight shift from 5mC to 5hmC is apparent, there is almost complete methylation (5mC) of the maternal PWS-IC in the ZNF274 KO PWS iPSCs. A minimum of 2 biological replicates per cell line were performed. Significance was calculated using two-way analysis of variance (ANOVA) test with a Dunnett post-test to compare the two LD KOs to PWS LD.

(FIG. 4A) LD KOs and (FIG. 4B) UPD KOs. FIG. 4C shows the combined data. The same color code as in FIG. 1B is used. Significance was calculated using two-way analysis of variance (ANOVA) test with a Dunnett post-test to compare the combined LD KOs to PWS LD and the combined UPD KOs to PWS UPD.

(FIG. 5A) Gene expression of the SNRPNU exons (U4/cx2), (FIG. 5B) SNRPN major promoter (ex1/2), and (FIG. 5C) SNRPN transcript body (ex3/4) in neurons. The same color code as in FIG. 1B is used. Data were normalized to CTRL1 or CTRL2 for each panel and plotted as the mean with Standard Deviation (SD). A minimum of 2 biological replicates per cell line were performed. Significance was calculated using one-way analysis of variance (ANOVA) test with a Dunnett post-test to compare the two LD KOs to PWS LD and the three UPD KOs to PWS UPD. FIG. 5D shows schematics of expression and splicing of 5' SNRPN exons in ZNF274 KO neurons. (FIG. 5E) DNA methylation level at the PWS-IC in mature 10-week-old neurons evaluated as in FIG. 2B. As expected, CTRL neurons show approximately equal levels of 5mC and C at the PWS-IC whereas PWS (LD and UPD) and AS neurons display, respectively, almost complete (5mC) and almost no (C) methylation. There is almost complete methylation (5mC) of the maternal PWS-IC in the ZNF274 KO PWS neurons. A minimum of 2 biological replicates per cell line were performed. Significance was calculated using two-way analysis of variance (ANOVA) test with a Dunnett post-test to compare the two LD KOs to PWS LD and the UPD KO to PWS UPD.

(FIG. 8A) Genetic map of the 8 exons of the ZNF274 gene. KRAB, SCAN, and DBD domains. The blue box represents the coding region. Arrows represent the start codons for the two major isoforms. CRISPR/Cas9-mediated knockout of ZNF274 was performed in PWS LD and PWS UPD, by designing two different single guide RNAs (sgRNAs), in exon 2 and 6 of the ZNF274 gene (NM_133502) to target the two major isoforms of ZNF274 (TABLE 4). 5 clonal iPSC clones were selected after screening for non-homologous end-joining-mediated insertions/deletions (indels) resulting in a frameshift and a premature stop codon. Magenta lines represent the positions of the guide RNAs. (FIG. 8B) Pluripotency validation of novel reprogrammed and engineered stem cell lines in this work. Phase images, DAPI, OCT4, and SSEA4 staining were viewed on an inverted Microscope at 10×, Olympus CKX41.

(FIG. 9A) ChIP assay of ZNF274 binding in iPSCs to four chromosome 19 ZNF274 binding sites. Same experimental conditions as for FIG. 1B (FIG. 9B and FIG. 9C) ChIP assay for the repressive histone modification H3K9me3 in iPSCs at the four ZNF274 chromosome 19 binding sites, and at the SNORD116 cluster Group 2 and 3 (G2 and G3) subregions as well as the PWS-IC. Same experimental conditions as for FIG. 1B. (FIG. 9D) Gene expression of the SNORD116 Host Gene Group 1 (116HGGI) in each cell line in iPSCs. The same color code as in FIG. 1B is used for PWS and ZNF274 KO cell lines. Gene expression was assessed using the comparative CT method, GAPDH was used as an endogenous control. Data were normalized to the PWS parental line for each panel and plotted as the mean with Standard Deviation (SD). A minimum of 3 biological replicates per cell line were performed. Significance was calculated using one-way analysis of variance (ANOVA) test with a Dunnett post-test to compare the two LD KOs to PWS LD and the three UPD KOs to PWS UPD.

FIG. 10 shows CRISPR-mediated knock out of ZNF274 in neurons from PWS iPSCs re-activated expression of maternal transcripts. The ZNF274 knockout clonal derivatives of PWS1-7 (B17-21 and ZKL6) and UPD1-2 (ZKU4B and ZKU21A) iPSCs were generated using LentiGuide CRISPR vectors with guide RNAs targeting the ZNF274. RNA was isolated from these neurons after 10 weeks of differentiation of PWS 1-7, B17-21, ZKL6, UPD1-2, ZKU4B, ZKU21A, and the normal control lines LcNL-1 and MCH2-10. Steady state RNA levels of SNORD116, IPW, and SNORD115 were measured by RT-qPCR using Taqman (ABI) assays.

FIG. 11 shows Group 1 SNORD116s share a 48 nt segment of DNA sequence identity except for single base pair substitutions within the yellow-highlighted ZNF274 motif. ZNF274 is highly enriched at SNORD116-3, -5, -7, -8, & -9.

DETAILED DESCRIPTION

Figure 1A:
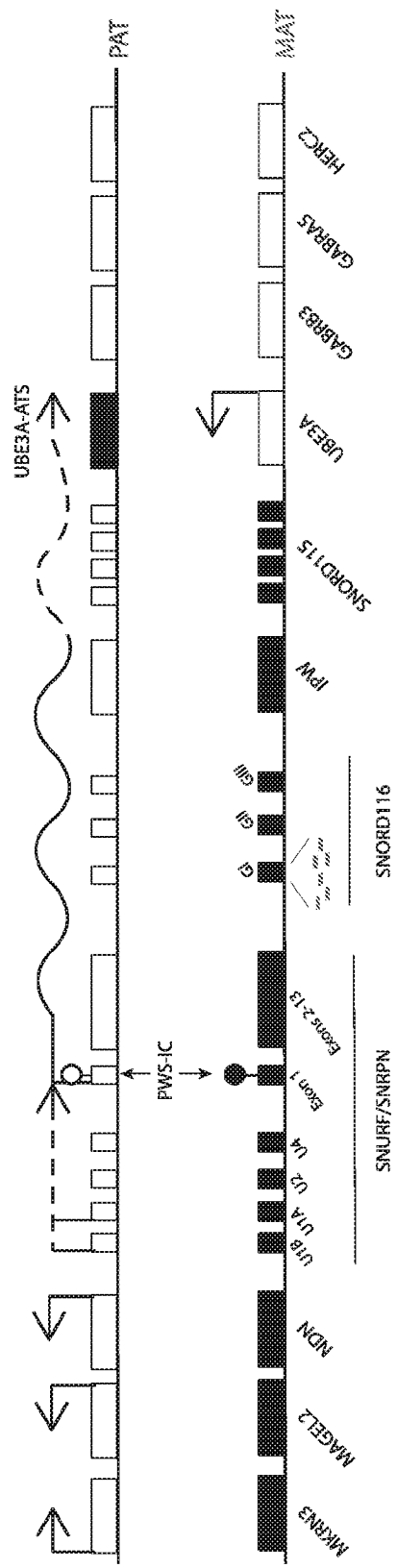
FIGS. 1A-1C show that CRISPR/Cas9-mediated Knock-Out of ZNF274 reduces H3K9me3 and activates SNORD116 expression in PWS iPSCs.

Described herein are compositions and methods for studying or treating a disorder of genomic imprinting, such as Prader-Willi Syndrome (PWS). The inventors discovered a component of the switch off mechanism, a protein called ZNF274 (zinc-finger protein ZNF274), which tethers a complex to the maternal PWS critical region (PWSCR). The PWSCR is a region on chromosome 15 at region 15q11-q13 that encompasses the cluster of 30 SNORD116 small nucleolar RNAs. Binding of the ZNF274 complex to the maternal PWSCR silences the genes encoded therein and silences RNA transcripts that are needed for normal development. Deletion of the ZNF274 protein or gene, as disclosed herein, can be used as a tool for further examination of disorders of genomic imprinting such as PWS.

In one disclosed example, ZNF274 was targeted for destruction in neurons derived from PWS-specific induced pluripotent stem cells, resulting in fully activating the maternal transcripts within the PWSCR. The inventors targeted ZNF274 using CRISPR/Cas9 technology and followed the impact of the knockout on maternal allele expression in PWS-specific iPSCs through the process of neuronal differentiation.

The inventors also discovered the nucleotide sequence of the binding site for ZNF274, which is involved in the pathology of PWS. Modification of the ZNF274 binding site can restore the expression of the silenced maternal genes within region 15q11-q13 and can be used as a treatment for PWS. As disclosed herein, activation of maternal PWSCR transcripts by blocking the interaction of a specific protein to DNA is a completely novel strategy and method of treating PWS. The identity of this DNA sequence greatly enables the disclosed therapeutic approach to PWS in which agents are developed, formulated, and administered to block the interaction between ZNF274 and the PWSCR.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of," and "consisting essentially of," the embodiments or elements presented herein, whether explicitly set forth or not.

All ranges disclosed herein are inclusive of the endpoints, and the endpoints are independently combinable with each other. Each range disclosed herein constitutes a disclosure of any point or sub-range lying within the disclosed range. For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another.

The modifier "about" used in connection with a quantity is inclusive of the stated value and has the meaning dictated by the context (e.g., it includes, at a minimum the degree of error associated with measurement of the particular quantity). The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed.

Chemical compounds are described using standard nomenclature. Unless defined otherwise, all technical and scientific terms used herein have the same meaning as is commonly understood by one of skill in the art to which this invention belongs.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Clustered Regularly Interspaced Short Palindromic Repeats" and "CRISPRs", as used interchangeably herein, refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Complement" as used herein can mean 100% complementarity (fully complementary) with the comparator nucleotide sequence or it can mean less than 100% complementarity (e.g., substantial complementarity)(e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity). Complement can also be used in terms of a "complement" to or "complementing" a mutation.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group.

Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target, gene expression, or for a protein activity may be defined in accordance with standard practice. A control may be a subject or cell without an agent or DNA targeting system as detailed herein. A control may be a subject or cell without a modified ZNF274 binding site as detailed herein. A control may be a subject or cell without a deleted ZNF274 as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene can be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

The term "genome" as used herein includes an organism's chromosomal/nuclear genome as well as any mitochondrial, and/or plasmid genome.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

An "isolated" polynucleotide or an "isolated" polypeptide is a nucleotide sequence or polypeptide sequence that, by the hand of man, exists apart from its native environment and is therefore not a product of nature. In some embodiments, the polynucleotides and polypeptides of the disclosure are "isolated." An isolated polynucleotide or polypeptide can exist in a purified form that is at least partially separated from at least some of the other components of the naturally occurring organism or virus, for example, the cell or viral structural components or other polypeptides or polynucleotides commonly found associated with the polypeptide or polynucleotide. In representative embodiments, the isolated polynucleotide and/or the isolated polypeptide is at least about 1%, 5%, 10%, 20%, 30%, 40%, 50%, 60%, 70%, 80%, 90%, 95%, or more pure.

In other embodiments, an isolated polynucleotide or polypeptide can exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue, or organ in which expression occurs or, with respect to the developmental stage at which expression occurs, or in response to external stimuli such as physiological stresses, pathogens, metal ions, or inducing agents. Representative examples of promoters include the EFS promoter, bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, human U6 (hU6) promoter, and CMV IE promoter.

A "protospacer sequence" refers to the target double stranded DNA and specifically to the portion of the target DNA (e.g., or target region in the genome) that is fully or substantially complementary (and hybridizes) to the spacer sequence of the CRISPR arrays. A spacer is designed to be complementary to the protospacer.

A "protospacer adjacent motif (PAM)" is a short motif of 2-4 base pairs present immediately 3' or 5' to the protospacer.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount.

"Sample" or "test sample" as used herein can mean any sample in which the presence and/or level of a target is to be detected or determined or any sample comprising an agent, DNA targeting system, gene, or gene product as detailed herein. Samples may include liquids, solutions, emulsions, or suspensions. Samples may include a medical sample.

Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

"Subject" as used herein can mean a mammal that wants or is in need of the herein described agents or methods. The subject may be diploid. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In some embodiments, the subject has a specific genetic marker.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

The terms "transformation," "transfection," and "transduction" as used interchangeably herein refer to the introduction of a heterologous nucleic acid molecule into a cell. Such introduction into a cell can be stable or transient. Thus, in some embodiments, a host cell or host organism is stably transformed with a polynucleotide of the disclosure. In other embodiments, a host cell or host organism is transiently transformed with a polynucleotide of the disclosure. "Transient transformation" in the context of a polynucleotide means that a polynucleotide is introduced into the cell and does not integrate into the genome of the cell. By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid, and the plastid genome, and therefore includes integration of the nucleic acid construct into, for example, the chloroplast or mitochondrial genome. Stable transformation as used herein can also refer to a transgene that is maintained extrachromasomally, for example, as a minichromosome or a plasmid. In some embodiments, the nucleotide sequences, constructs, expression cassettes can be expressed transiently and/or they can be stably incorporated into the genome of the host organism.

"Treatment" or "treating," when referring to protection of a subject from a disease, means suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid.

2. DISORDER OF GENOMIC IMPRINTING

Provided herein are compositions and methods for treating disorders of genomic imprinting. Genomic imprinting is an epigenetic process in diploid organisms wherein a gene is expressed or not expressed (silenced) based on the parent from which the gene originated. In diploid organisms, somatic cells have two copies of the genome, one inherited from the father and one from the mother. Each autosomal gene is therefore represented by two copies, or alleles, with one copy inherited from each parent at fertilization. For most autosomal genes in a diploid organism, expression of a gene occurs from both alleles simultaneously. In mammals, however, some genes are imprinted, meaning that gene expression occurs from only one allele. The expressed allele is dependent upon its parental origin. Various disorders may arise when, for example, the expressed allele is missing while the allele still present is silenced. Disorders of genomic imprinting include, for example, Prader-Willi Syndrome (PWS), and Angelman Syndrome.

a) Prader-Willi Syndrome (PWS)

Prader-Willi Syndrome (PWS) is a disorder of genomic imprinting. In healthy subjects, chromosome 15 that is inherited from the father has a set of genes that are transcriptionally active while the same set of genes on the chromosome 15 inherited from the mother are transcriptionally silenced. In PWS, there is no normal copy of the paternal chromosome 15, so subjects only have the silent copies inherited from the mother. More specifically, PWS is caused by the absence of a normal paternal contribution to chromosome 15 at position 15q11-q13. In some embodiments, the absence of paternal chromosome 15 at region 15q11-q13 is due to a large deletion (LD) of the approximately 5,000 kb imprinted paternal region. In other embodiments, the absence of paternal chromosome 15 at region 15q11-q13 is due to maternal uniparental disomy (mUPD) of chromosome 15 at region 15q11-q13. UPD is when a subject has two copies of a chromosome or portion thereof from one parent, and no copy of the chromosome or portion thereof from the other parent.

PWS may be characterized by neonatal hypotonia, failure to thrive during infancy, developmental delay, hyperphagia, obesity, cognitive disability, behavioral abnormalities, or a combination thereof.

Angelman Syndrome is caused by an inherited deletion of maternal chromosome 15 at region 15q11-q13, or by paternal UPD of chromosome 15 at region 15q11-q13. Angelman Syndrome is characterized by seizures, movement difficulty, cognitive disability, failure to speak, or a combination thereof.

b) Genes

The PWS Critical Region (PWSCR) is a region on chromosome 15 within position 15q11-q13. The germline imprint of chromosome 15 at region 15q11-q13 is a differentially methylated CG-rich segment, termed the PWS-IC, which is located in the first exon of the gene encoding small nuclear ribonucleoprotein polypeptide N (SNRPN). SNRPN is a bicistronic transcript that also encodes SNURF (also referred to as SNRPN). In the brain, a long non-coding RNA (lnc RNA) initiates at upstream (U) exons of SNRPN (FIG. 1A), extends >600 kb distally to overlap UBE3A, and silences the paternal UBE3A allele via an antisense-mediated mechanism.

The PWSCR has been narrowed to a 91 kb segment encompassing the SNORD116 cluster and the IPW (Imprinted In Prader-Willi Syndrome) transcript. The SNORD116 cluster is a polynucleotide encoding 30 SNORD116 small nucleolar RNAs. Small nucleolar RNAs (snoRNAs) are a class of small RNA molecules that primarily guide chemical modifications of other RNAs, such as ribosomal RNAs, transfer RNAs, and small nuclear RNAs. The two main classes of snoRNA are the C/D box snoRNAs, which are associated with methylation, and the H/ACA box snoRNAs, which are associated with pseudouridylation. The long non-coding antisense RNA (lncRNA) serves as the host gene (HG) to several box C/D class small nucleolar RNAs including the SNORD116 and SNORD115 clusters.

The cluster of 30 copies of SNORD116s in the PWSCR are classified into three groups based on DNA sequence similarity. Group 1 (SNOG1) includes SNORD116 1-9. Group 2 (SNOG2) includes SNORD116 10-24. Group 3 (SNOG3) includes SNORD116 25-30. Loss of SNORD116 in both human iPSC deletion and mouse models of PWS have a deficiency of prohormone convertase PC1 that may potentially be associated with the neuroendocrine dysfunction in PWS, which may indicate an association between SNORD116 deletion and PWS.

c) Zinc Finger Protein 274 (ZNF274)

Zinc Finger Protein 274 (ZNF274) is a component of the silencing mechanism of maternal chromosome 15 at position 15q11-q13. ZNF274 tethers a complex to maternal chromosome 15 at position 15q11-q13 that silences RNA transcripts that are needed for normal development. The complex may include the SET domain bifurcated 1 (SETDB1) histone H3 lysine 9 (H3K9) methyltransferase. The complex of ZNF274 and the methyltransferase may mediate the deposition of the repressive H3K9me3 chromatin mark on the maternal allele.

i. ZNF274 Binding Site

The ZNF274 protein binds to a ZNF274 binding site that comprises a polynucleotide sequence on chromosome 15 within position 15q11-q13. The ZNF274 consensus binding sequence is contained within the 48-nucleotide sequence of SNORD116-3, -5, -7, -8 and -9. The functionality of the predicted binding ZNF274 binding site at SNORD116 has been confirmed by genome editing technology. The 48-nucleotide ZNF274 consensus sequence in the PWSCR is conserved in nonhuman primates and, thus, the disclosed strategy and methods could be applied in animal models. In one aspect of developing agents for treatment of PWS, compounds are selected or designed based on their ability to interfere with ZNF274 binding to the PWSCR and thereby activate the maternal PWSCR RNA transcripts.

As detailed herein, a computational approach was used to identify the 14-nucleotide consensus binding site sequence that is recognized by ZNF274 for binding to DNA throughout the human genome. This 14-nucleotide consensus binding site sequence was used to find the precise ZNF274 binding sites in chromosome 15 at position 15q11-q13. The ZNF274 binding site in chromosome 15 at position 15q11-q13 is a 18-nucleotide sequence (SEQ ID NO: 1, TGAGT- GAGAACTCATACC) that is contained within the 48-nucleotide sequence of each of the Group 1 SNORD116s (SNORD116-1, 2, 3, 4, 5, 6, 7, 8, or 9). The 48-nucleotide sequences of SNORD116-1, 2, 3, 4, 5, 6, 7, 8, and 9 are identical, except for a single nucleotide change in SNORD116-1, 2, 4 and 6. This single nucleotide difference is within the ZNF274 binding site (TABLE 1; FIG. 11). ZNF274 can bind to SNORD116-3, 5, 7, 8 and 9 in the maternal copy of the SNORD116 cluster, as confirmed by ChIP-Seq analysis (Crunivel et al. *Hum. Mol. Genet.* 2014, 23, 4674-85). SNORD116-2, 4, and 6 each display a G to A substitution at position 8 in the ZNF274 binding site and can also be bound by ZNF274 according to ChIP-Seq data. SNORD116-1 contains a different single nucleotide change from the consensus ZNF274 binding site. The 48-nucleotide conserved sequence of the Group 1 SNORD116s in the PWSCR is conserved in nonhuman primates, except for the substitutions within the ZNF274 binding site. The ZNF274 binding site may comprises a polynucleotide having at least 70%, at least 75%, at least 80%, at least 85%, or at least 90% sequence identity to SEQ ID NO: 1. In some embodiments, the ZNF274 binding site comprises a polynucleotide having at least 90% sequence identity to SEQ ID NO: 1. In some embodiments, the ZNF274 binding site comprises a polynucleotide corresponding to SEQ ID NO: 1. In some embodiments, the ZNF274 binding site consists of a polynucleotide having at least 90% sequence identity to SEQ ID NO: 1. In some embodiments, the ZNF274 binding site consists of a polynucleotide corresponding to SEQ ID NO: 1.

TABLE 1

Sequences of the Group 1 SNORD116s (SNORD116-1, 2, 3, 4, 5, 6, 7, 8, or 9), with the ZNF274 binding site underlined.

| SNORD 116- | SEQUENCE | SEQ ID NO: |
|---|---|---|
| 1 | AAAAACATTCCTTGGAAAAGCTGAACAAAA TGAGTGAGAACTCATAAC | 4 |
| 2 | AAAAACATTCCTTGGAAAAGCTGAACAAAA TGAGTGAAAACTCATACC | 5 |
| 3 | AAAAACATTCCTTGGAAAAGCTGAACAAAA TGAGTGAGAACTCATACC | 6 |
| 4 | AAAAACATTCCTTGGAAAAGCTGAACAAAA TGAGTGAAAACTCATACC | 7 |
| 5 | AAAAACATTCCTTGGAAAAGCTGAACAAAA TGAGTGAGAACTCATACC | 8 |
| 6 | AAAAACATTCCTTGGAAAAGCTGAACAAAA TGAGTGAAAACTCATACC | 9 |
| 7 | AAAAACATTCCTTGGAAAAGCTGAACAAAA TGAGTGAGAACTCATACC | 10 |
| 8 | AAAAACATTCCTTGGAAAAGCTGAACAAAA TGAGTGAGAACTCATACC | 11 |
| 9 | AAAAACATTCCTTGGAAAAGCTGAACAAAA TGAGTGAGAACTCATACC | 12 |

3. Agent that Reduces Interaction of ZNF274 Protein with ZNF274 Binding Site

Provided herein are agents that reduce the interaction of ZNF274 protein with the ZNF274 binding site. In some embodiments, the agent deletes the ZNF274 protein. In other embodiments, the ZNF274 binding site is modified. In some embodiments, the agent is a zinc finger nuclease, a TAL effector nuclease, or DNA targeting system, such as a CRISPR/Cas9 DNA targeting system.

a) Deletion of ZNF274 Protein

Also disclosed herein is a technology for generating PWS-specific iPSC (induced pluripotent stem cells) and their neuronal differentiation to study aspects of epigenetic regulation and the PWS disease mechanism. A ZNF274/SETDB1-containing epigenetic complex was discovered that binds maternal PWSCR to effect epigenetic silencing via the accumulation of H3K9me3 at the PWSCR. In some embodiments, CRISPR lentiviral vectors can be used to target ZNF274 and generate ZNF274 knock out clonal derivatives of the PWS iPSC lines, PWS1-7 large deletion (B17-21 and ZKL6), and UPD 1-2 (ZKU4B and ZKU21A). In some embodiments, the two parental PWS iPSC lines and each of their two ZNF274 KO clonal derivatives as well as two normal controls (LcNL-1 and MCH2-10) can be differentiated into neurons.

In some embodiments, the agent deletes the ZNF274 protein from a subject. The agent may delete the ZNF274 gene from a subject's genome. Without the ZNF274 gene or protein present, expression of genes from maternal chromosome 15 at position 15q11-q13 may be expressed and no longer silenced. Deletion of ZNF274 may activate expression of maternal transcripts from the PWSCR. Deletion of ZNF274 may re-activate expression of silent maternal transcripts from the PWSCR. Deletion of ZNF274 may result in a reduction of H3K9me3 binding within the PWSCR. In some embodiments, deletion of ZNF274 induces expression of transcripts from maternal chromosome 15 at position 15q11-q13 such that the expression level is the same as in a control, the control being, for example, a cell from a non-PWS or healthy subject. Activation of expression upon ZNF274 deletion may be not only within the PWSCR but also throughout the chromosome 15q11-q13 imprinted region.

In some embodiments upon ZNF274 knock out, a complete re-activation of neuronal transcripts is achieved for RNA transcripts from the PWS region, such as, for example, SNORD116, IPW, and SNORD115. In some embodiments, deletion of ZNF274 increases or activates expression of both MAGEL2 and MKRN3. In some embodiments, deletion of ZNF274 increases or activates expression of both MAGEL2 and MKRN3 in PWS LD and UPD neurons.

Knockout of the ZNF274 protein may rescue the expression of silent maternal alleles without affecting DNA methylation at the PWS-Imprinting Center (PWS-IC). The ZNF274 complex may be a separate imprinting mark that represses maternal PWS gene expression in neurons.

Knockout of the ZNF274 protein as detailed herein may be used as a research tool or to screen various potential therapies for disorders such as PWS. Genome-wide knockout of the ZNF274 protein is not a feasible approach to treat PWS. ZNF274 can bind to genome locations other than chromosome 15 at position 15q11-q13, and so genome-wide knockout of the ZNF274 protein in subjects with PWS would likely have additional unfavorable complications.

b) Modification Of ZNF274 Binding Site

In some embodiments, the binding of the ZNF274 protein to the ZNF274 binding site is inhibited by modifications to the ZNF274 binding site. In some embodiments, the ZNF274 binding sites in chromosome 15 at position 15q11-q13 are modified, while other ZNF274 binding sites elsewhere in the genome are not modified. Modifications may include full deletion of the ZNF274 binding site, partial deletion of the ZNF274 binding site, mutation of one or more nucleotides of the ZNF274 binding site, cutting the ZNF274 binding site at one or more nucleotide positions, or a combination thereof. In some embodiments, binding of the ZNF274 protein to the ZNF274 binding site is reduced at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, or about 100% relative to a control.

4. DNA TARGETING SYSTEM

In some embodiments, the agent comprises a DNA targeting system. The DNA targeting system may comprise at least one gRNA. The DNA targeting system may further comprise a Cas protein.

a) Guide RNA (gRNA)

The DNA targeting system may comprise at least one gRNA that binds and targets a polynucleotide sequence. In embodiments wherein the ZNF274 binding is modified, the gRNA binds and targets a polynucleotide sequence corresponding to SEQ ID NO: 1, SEQ ID NO: 42, SEQ ID NO: 43, SEQ ID NO: 44, SEQ ID NO: 45, SEQ ID NO: 46, complement thereof, or variant thereof. In some embodiments, the gRNA molecule binds and targets a polynucleotide sequence having at least about 75%, at least about 80%, at least about 85%, at least about 90%, at least about 95%, at least about 96%, at least about 97%, at least about 98%, at least about 99%, or 100% identity to the polynucleotide sequence of SEQ ID NO: 1, SEQ ID NO: 42, SEQ ID NO: 43, SEQ ID NO: 44, SEQ ID NO: 45, SEQ ID NO: 46, complement thereof. In some embodiments, the gRNA molecule comprises a polynucleotide sequence SEQ ID NO: 43, SEQ ID NO: 44, SEQ ID NO: 45, SEQ ID NO: 46, complement thereof, or a variant thereof. In some embodiments, the gRNA molecule comprises a polynucleotide sequence having at least about 75%, at least about 80%, at least about 85%, at least about 90%, at least about 95%, at least about 96%, at least about 97%, at least about 98%, at least about 99%, or 100% identity to the polynucleotide sequence of SEQ ID NO: 43, SEQ ID NO: 44, SEQ ID NO: 45, SEQ ID NO: 46, or complement thereof.

In embodiments wherein the ZNF274 protein is deleted, the gRNA binds to a gene encoding a ZNF274 protein. The gRNA may bind and target a polynucleotide sequence corresponding to SEQ ID NO: 13, SEQ ID NO: 14, SEQ ID NO: 16, SEQ ID NO: 17, SEQ ID NO: 47, SEQ ID NO: 48, complement thereof, or variant thereof. In some embodiments, the gRNA molecule binds and targets a polynucleotide sequence having at least about 75%, at least about 80%, at least about 85%, at least about 90%, at least about 95%, at least about 96%, at least about 97%, at least about 98%, at least about 99%, or 100% identity to the polynucleotide sequence of corresponding to SEQ ID NO: 13, SEQ ID NO: 14, SEQ ID NO: 16, SEQ ID NO: 17, SEQ ID NO: 47, SEQ ID NO: 48, or complement thereof. In some embodiments, the gRNA molecule comprises a polynucleotides sequence corresponding to SEQ ID NO: 13, SEQ ID NO: 14, SEQ ID NO: 47, SEQ ID NO: 48, complement thereof, or a variant thereof. In some embodiments, the gRNA molecule comprises a polynucleotides sequence having at least about 75%, at least about 80%, at least about 85%, at least about 90%, at least about 95%, at least about 96%, at least about 97%, at least about 98%, at least about 99%, or 100% identity to the polynucleotide sequence of corresponding to SEQ ID NO: 13, SEQ ID NO: 14, SEQ ID NO: 47, SEQ ID NO: 48, or complement thereof.

b) CRISPR-Based Nuclease

The DNA targeting system may include a CRISPR-based nuclease or a nucleic acid sequence encoding a CRISPR-based nuclease. In some embodiments, the nucleic acid sequence encoding a CRISPR-based nuclease is DNA. In some embodiments, the nucleic acid sequence encoding a CRISPR-based nuclease is RNA. The CRISPR system is a microbial nuclease system involved in the defense against invading phages and plasmids and provides a form of acquired immunity. The CRISPR loci in microbial hosts contain a combination of CRISPR-associated (Cas) genes as well as non-coding RNA elements responsible for the specificity of the CRISPR-mediated nucleic acid cleavage.

CRISPR systems are organized into two classes, each composed of 3 system types with are further divided into 19 different subtypes. Class 1 systems use a complex of multiple Cas proteins to aid in the cleavage of foreign nucleic acids. Class 2 uses a single large Cas protein for the same purpose. Since class 2 only requires a single Cas protein, class 2 Cas proteins have been exploited and adapted for use in eukaryotic systems. Each type and most subtypes are characterized by a 'signature gene' found almost exclusively in that category. CRISPR/Cas9 is the most well-known class 2 protein used for genome engineering.

The CRISPR-based nuclease forms a complex with the 3' end of a gRNA. The specificity of the CRISPR-based system depends on two factors: the target sequence and the proto-spacer-adjacent motif (PAM). The target sequence is located on the 5' end of the gRNA and is designed to bond with base pairs on the host DNA at the correct DNA sequence known as the protospacer. By simply exchanging the recognition sequence of the gRNA, the CRISPR-based nuclease can be directed to new genomic targets. The PAM sequence is located on the DNA to be cleaved and is recognized by a CRISPR-based nuclease. PAM recognition sequences of the CRISPR-based nuclease can be species specific. In some embodiments, the CRISPR-based nuclease can be a Cas9 protein or molecule or a Cpf1 protein or molecule, such as a Cas9 endonuclease or a Cpf1 endonuclease.

In some embodiments, the CRISPR-based nuclease is a Cas9 endonuclease derived from a bacterial genus of *Streptococcus, Staphylococcus, Brevibacillus, Corynebacter, Sutterella, Legionella, Francisella, Treponema, Filifactor, Eubacterium, Lactobacillus, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma*, or *Campylobacter*. In some embodiments, the Cas9 protein is selected from the group, including, but not limited to, *Streptococcus pyogenes, Francisella novicida, Staphylococcus aureus, Neisseria meningitides, Streptococcus thermophiles, Treponema denticola, Brevibacillus laterosporus, Campylobacter jejuni, Corynebacterium diphtheria, Eubacterium ventriosum, Streptococcus pasteurianus, Lactobacillus farciminis, Sphaerochaeta globus, Azospirillum, Gluconacetobacter diazotrophicus, Neisseria cinerea, Roseburia intestinalis, Parvibaculum lavamentivorans, Nitratifractor salsuginis*, and *Campylobacter lari*.

In some embodiments, the Cas9 protein or molecule is selected from the group including, but not limited to, *Streptococcus pyogenes* Cas9 (SpCas9) endonuclease, a *Francisella novicida* Cas9 (FnCas9) endonuclease, a *Staphylococcus aureus* Cas9 (SaCas9) endonuclease, *Neisseria meningitides* Cas9 (NmCas9) endonuclease, *Streptococcus thermophiles* Cas9 (StCas9) endonuclease, *Treponema den-*

*ticola* Cas9 (TdCas9) endonuclease, *Brevibacillus laterosporus* Cas9 (BlatCas9) endonuclease, *Campylobacter jejuni* Cas9 (CjCas9) endonuclease, a variant endonuclease thereof, or a chimera endonuclease thereof. In some embodiments, the Cas9 endonuclease is a SpCas9 variant endonuclease. In some embodiments, the SpCas9 variant is a SpCas9 VQR variant endonuclease, a SpCas9 Cas9 VRER variant endonuclease, a SpCas9 Cas9 EQR variant endonuclease, a SpCas9-HF1 variant endonuclease, or an eSpCas9 (1.1) variant endonuclease.

i. PAM Sequence Recognition

The CRISPR nuclease complex unwinds a DNA duplex and searches for sequences complementary to the gRNA and the correct PAM. The nuclease only mediates cleavage of the target DNA if both conditions are met. By specifying the type of CRISPR-based nuclease and the sequence of one or more gRNA molecules, DNA cleavage sites can be localized to a specific target domain. Given that PAM sequences are variant and species specific, target sequences can be engineered to be recognized by only certain CRISPR-based nucleases.

In some embodiments, the Cas9 endonuclease can recognize a PAM sequence NGG (SEQ ID NO: 2) or NGA (SEQ ID NO: 3). In some embodiments, the Cas9 endonuclease is a SpCas9 endonuclease and recognizes the PAM sequence of NGG (SEQ ID NO: 2). In some embodiments, the Cas9 endonuclease is a SpCas9 VQR variant endonuclease and recognizes the PAM sequence of NGA (SEQ ID NO: 3), NGAN (SEQ ID NO: 49) or NGNG (SEQ ID NO: 50).

5. POLYNUCLEOTIDES

Further provided herein is an isolated polynucleotide sequence comprising a gRNA. Also provided herein is an isolated polynucleotide sequence encoding a DNA targeting system. The polynucleotide sequence may be comprised within a vector. The vector may encode a gRNA molecule and a Cas protein. In some embodiments, the vector can be an expression vector or system to produce protein by routine techniques and readily available starting materials including Sambrook et al., Molecular Cloning and Laboratory Manual, Second Ed., Cold Spring Harbor (1989). In some embodiments, the vector can comprise the nucleic acid sequence encoding the gRNA and/or a Cas protein or molecule.

a) Constructs and Plasmids

The genetic construct, such as a plasmid, expression cassette or vector, can comprise a nucleic acid that encodes the gRNA and/or the DNA targeting system, as disclosed herein. The genetic construct can be present in the cell as a functioning extrachromosomal molecule. The genetic construct can be a linear minichromosome including centromere, telomeres or plasmids or cosmids. In some embodiments, the genetic construct can include at least one polynucleotide sequence of SEQ ID NO: 13, 14, 43-48, and/or combinations thereof.

The genetic construct can also be part of a genome of a recombinant viral vector, including recombinant lentivirus, recombinant adenovirus, recombinant adenovirus associated virus, and recombinant herpes simplex virus (HSV). The genetic construct can be part of the genetic material in attenuated live microorganisms or recombinant microbial vectors which live in cells. The compositions, as described above, can comprise genetic constructs that encode the modified lentiviral vector and a nucleic acid sequence that encodes gRNA and/or the DNA targeting system, as disclosed herein.

The nucleic acid sequences can make up a genetic construct that can be a vector. The vector can be capable of expressing the gRNA and/or the DNA targeting system in the cell of a mammal. The vector can be recombinant. The vector can comprise heterologous nucleic acid encoding the gRNA and/or the DNA targeting system. The vector can be a plasmid. The vector can be useful for transfecting cells with nucleic acid encoding the gRNA and/or the DNA targeting system, which the transformed host cell is cultured and maintained under conditions wherein expression of the gRNA and/or the DNA targeting system takes place.

In further embodiments of the disclosure, the genetic constructs and polynucleotides comprising polynucleotides encoding gRNA and/or the DNA targeting system can be operatively associated with a variety of promoters, terminators and other regulatory elements for expression in various organisms or cells. In some embodiments, the genetic constructs can comprise regulatory elements for gene expression of the coding sequences of the nucleic acid. In some embodiments, the regulatory elements can be a promoter, an enhancer, an initiation codon, a stop codon, or a polyadenylation signal.

In representative embodiments, at least one promoter and/or terminator can be operably linked to a polynucleotide of the disclosure. Any promoter useful with this disclosure can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid.

An expression cassette also can optionally include a transcriptional and/or translational termination region (i.e., termination region) that is functional in the selected host cell. A variety of transcriptional terminators is available for use in expression cassettes and can be responsible for the termination of transcription beyond the heterologous nucleotide sequence of interest. The termination region can be native to the transcriptional initiation region, can be native to the operably linked nucleotide sequence of interest, can be native to the host cell, or can be derived from another source (i.e., foreign or heterologous to the promoter, to the nucleotide sequence of interest, to the host, or any combination thereof). In some embodiments of this disclosure, terminators can be operably linked to a recombinant polynucleotide(s) encoding the DNA targeting system.

In addition to expression cassettes, the recombinant polynucleotides described herein (e.g., polynucleotides comprising a polynucleotide encoding CRISPR-based nuclease) can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. A vector as defined herein can transform a eukaryotic host either by integration into the cellular genome or exist as an extrachromosomal element (e.g., minichromosome). In some embodiments, the recombinant polynucleotides described herein can be delivered as a ribonucleoprotein complex.

The vector can comprise heterologous nucleic acid encoding the gRNA and/or the DNA targeting system, and can further comprise an initiation codon, which can be upstream of the gRNA and/or the DNA targeting system, and a stop codon, which can be downstream of the gRNA and/or the DNA targeting system. The initiation and termination codon can be in frame with the gRNA and/or the DNA targeting system. The vector can also comprise a promoter that is operably linked to the gRNA and/or the DNA targeting system.

b) Viral Packaging

In some embodiments, the gRNA or DNA targeting system may be packaged in a viral vector. In some embodiments, the gRNA and the nucleic acid sequence encoding the Cas protein or molecule are packaged in the same viral vector. In some embodiments, the gRNA and the nucleic acid sequence encoding the Cas protein or molecule are packaged in different viral vectors. In some embodiments, the vector may be an adeno-associated virus (AAV) or a lentiviral vector.

i. Modified Lentiviral Vector

Lentiviral vector is a vector belonging to the lentivirus family of retroviruses that are able to infect human and other mammalian species. The compositions for gene editing can include a modified lentiviral vector. The modified lentiviral vector can include one or more polynucleotide sequences encoding the gRNA and/or the nucleic acid sequence encoding the Cas protein or molecule. The modified lentiviral vector can include a first polynucleotide sequence encoding the gRNA and a second polynucleotide sequence encoding the Cas protein or molecule. The one or more polynucleotide sequences can be operably linked to a eukaryotic promoter. The promoter can be a constitutive promoter, an inducible promoter, a repressible promoter, or a regulatable promoter.

ii. Adeno-Associated Virus Vectors

The AAV vector is a small virus belonging to the genus Dependovirus of the Parvoviridae family that infects humans and some other primate species. AAV can be used to deliver the compositions to the cell using various construct configurations. For example, AAV can deliver genetic constructs encoding CRISPR-based nucleases, inserts, and/or gRNA expression cassettes on separate vectors. The composition, as described above, includes a modified adeno-associated virus (AAV) vector. The modified AAV vector can be capable of delivering and expressing the CRISPR-based nuclease in the cell of a mammal. For example, the modified AAV vector can be an AAV-SASTG vector (Piacentino et al. (2012) Human Gene Therapy 23:635-646). The modified AAV vector can be based on one or more of several capsid types, including AAV1, AAV2, AAV5, AAV6, AAV8, AAV9, and AAV-PHP.eB.

6. METHODS OF DELIVERY

The gRNA, DNA targeting system, isolated polynucleotide sequence, vector, or combination thereof, as disclosed in the present invention may be delivered using any method of DNA delivery to cells, including non-viral and viral methods. Common non-viral delivery methods include transformation and transfection. Non-viral gene delivery can be mediated by physical methods such as electroporation, microinjection, particle-mediated gene transfer ('gene gun'), impalefection, hydrostatic pressure, continuous infusion, sonication, chemical transfection, lipofection, or DNA injection (DNA vaccination) with and without in vivo electroporation. Viral mediated gene delivery, or viral transduction, utilizes the ability of a virus to inject its DNA inside a host cell. The genetic constructs intended for delivery are packaged into a replication-deficient viral particle. Common viruses used include retrovirus, lentivirus, adneovirus, adeno-associated virus, and herpes simplex virus. In some embodiments of the present invention, the adeno-associated virus is used for delivery of the genetic constructs.

7. CELLS

Further provided herein are cells. Any of the delivery methods can be utilized with a myriad of cell types, including, but not limited to, eukaryotic cells, like animal cells, such as mouse, rat, hamster, non-human primate, pig, or human cells. In some embodiments, the cell is a eukaryotic cell. In some embodiments, the cell is a human cell. The cells may be used to study aspects of epigenetic regulation, genomic imprinting, the PWS disease mechanism, or a combination thereof. The cell may comprise a gRNA, a DNA targeting system, an isolated polynucleotide sequence, a vector, or a combination thereof. In some embodiments, the cell is an Induced Pluripotent Stem Cell (iPSC). The iPSC may be from a Prader-Willi syndrome (PWS) patient. The iPSC may be differentiated into neurons. The iPSC may be from a PWS1-7 large deletion cell line or UPD 1-2 cell line. In some embodiments, the cell is a neuronal cell. In some embodiments, the cell is a neuronal progenitor cell (NPC).

8. PHARMACEUTICAL COMPOSITIONS

Further provided herein is a pharmaceutical composition. The agents and systems as detailed herein may be formulated into pharmaceutical compositions in accordance with standard techniques well known to those skilled in the pharmaceutical art. The composition may comprise an agent and a pharmaceutically acceptable carrier. The term "pharmaceutically acceptable carrier," as used herein, means a non-toxic, inert solid, semi-solid or liquid filler, diluent, encapsulating material or formulation auxiliary of any type. The pharmaceutical composition may include a gRNA, a DNA targeting system, an isolated polynucleotide sequence, a vector, a cell, or a combination thereof.

The pharmaceutical composition may comprise about 1 ng to about 10 mg of DNA encoding the gRNA, the DNA targeting system, the isolated polynucleotide sequence, or the vector. The pharmaceutical compositions according to the present invention are formulated according to the mode of administration to be used. In cases where pharmaceutical compositions are injectable pharmaceutical compositions, they are sterile, pyrogen free, and particulate free. An isotonic formulation is preferably used. Generally, additives for isotonicity may include sodium chloride, dextrose, mannitol, sorbitol, and lactose. In some cases, isotonic solutions such as phosphate buffered saline are preferred. Stabilizers include gelatin and albumin. In some embodiments, a vasoconstriction agent is added to the formulation.

The pharmaceutical composition containing the gRNA, the DNA targeting system, the isolated polynucleotide sequence, or the vector may further comprise a pharmaceutically acceptable excipient. The pharmaceutically acceptable excipient may be functional molecules as vehicles, adjuvants, carriers, or diluents. The method of administration will dictate the type of carrier to be used. Any suitable pharmaceutically acceptable excipient for the desired method of administration may be used. The pharmaceutically acceptable excipient may be a transfection facilitating agent. The transfection facilitating agent may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. The transfection facilitating agent may be a polyanion, polycation, including poly-L-glutamate (LGS), or lipid. The transfection facilitating agent may be poly-L-glutamate. The poly-L-glutamate may be present in the pharmaceutical composition at a concentration less than 6 mg/mL. The pharmaceutical composition may include transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

The route by which the disclosed agents are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Other embodiments of the agents disclosed herein include formulations and compositions comprising the agents disclosed herein, wherein those formulations and compositions may also comprise pharmaceutically acceptable excipients and other ingredients, which may be active or inactive. For oral administration, the pharmaceutical preparation can be in liquid form, for example, solutions, syrups or suspensions, or can be presented as a drug product for reconstitution with water or other suitable vehicle before use. Preparations for oral administration can be suitably formulated to give controlled release of active compounds.

9. ADMINISTRATION

The agents as detailed herein, or the pharmaceutical compositions comprising the same, may be administered to a subject. Such compositions comprising an agent can be administered in dosages and by techniques well known to those skilled in the medical arts taking into consideration such factors as the age, sex, weight, and condition of the particular subject, and the route of administration.

The specific therapeutically effective amount for a particular patient of an agent, composition or formulation disclosed herein will depend on a variety of factors including the activity of the specific compound employed, the age, body weight, general health, sex, diet, time of administration, route of administration, rate of excretion, drug combination, and the severity of the particular disease undergoing therapy. Concentrations of the agents described herein found in therapeutic compositions will vary depending upon a number of factors, including the dosage of the drug to be administered, the chemical characteristics (e.g., hydrophobicity) of the compounds employed, and the route of administration.

The agent can be administered prophylactically or therapeutically. In prophylactic administration, the agent can be administered in an amount sufficient to induce a response. In therapeutic applications, the agents are administered to a subject in need thereof in an amount sufficient to elicit a therapeutic effect. An amount adequate to accomplish this is defined as "therapeutically effective amount." Amounts effective for this use will depend on, e.g., the particular composition of the compound regimen administered, the manner of administration, the stage and severity of the disease, the general state of health of the patient, and the judgment of the prescribing physician. A therapeutically effective amount is also one in which any toxic or detrimental effects of an agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of an agent, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The agent can be administered by methods well known in the art as described in Donnelly et al. (Ann. Rev. Immunol. 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The agent can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The agent can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the agent is administered intravenously, intraarterially, or intraperitoneally to the subject. In some embodiments, the agent is administered to the central nervous system of the subject. In some embodiments, the agent is administered to the subject orally.

In other embodiments compositions can be formulated for parenteral administration by injection, and such formulations can be presented in unit dosage form, with or without an added preservative. The compositions can take such forms as suspensions, solutions or emulsions in oily or aqueous vehicles, and can contain formulatory agents such as suspending, stabilizing and/or dispersing agents.

10. KITS

Further provided herein is a kit. The kit may include a gRNA, a DNA targeting system, an isolated polynucleotide sequence, a vector, a cell, or a combination thereof. The kit may further include instructions for use. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

11. METHODS OF USING THE AGENTS a) Methods for Treating a Disorder of Genomic Imprinting in a Subject Provided herein are methods for treating a disorder of genomic imprinting in a subject. The method may include modifying a ZNF274 binding site on maternal chromosome 15 at position 15q11-q13 of the subject, such that the binding of a ZNF274 protein to the ZNF274 binding site is reduced relative to a control. In some embodiments, the ZNF274 binding site comprises a polynucleotide having at least 90% sequence identity to SEQ ID NO: 1, SEQ ID NO: 42, SEQ ID NO: 43, SEQ ID NO: 44, SEQ ID NO: 45, SEQ ID NO: 46, or complement thereof.

In some embodiments, binding of the ZNF274 protein to the ZNF274 binding site is reduced by at least 90% relative to a control. In some embodiments, binding of the ZNF274 protein to the ZNF274 binding site is eliminated. In some embodiments, the maternal chromosome 15 at position 15q11-q13 of the subject is silenced prior to modification of the ZNF274 binding site. In some embodiments, the disorder comprises Prader-Willi syndrome (PWS).

In some embodiments, the ZNF274 binding site is modified by fully deleting the ZNF274 binding site, partially deleting the ZNF274 binding site, mutating one or more nucleotides of the ZNF274 binding site, cutting the ZNF274 binding site at one or more nucleotide positions, or a combination thereof. In some embodiments, the ZNF274 binding site is modified by administering to the subject or a cell of the subject a DNA targeting system, as described herein, that binds to the ZNF274 binding site, wherein the DNA targeting system comprises at least one gRNA that binds and targets a polynucleotide sequence corresponding to SEQ ID NO: 1, SEQ ID NO: 42, SEQ ID NO: 43, SEQ ID NO: 44, SEQ ID NO: 45, SEQ ID NO: 46, complement thereof, or variant thereof. In some embodiments, the ZNF274 binding site is modified by administering an isolated polynucleotide encoding a DNA targeting system that binds to the ZNF274 binding site, the DNA targeting system comprising at least one gRNA that binds and targets a polynucleotide sequence corresponding to SEQ ID NO: 1, SEQ ID NO: 42, SEQ ID NO: 43, SEQ ID NO: 44, SEQ ID NO: 45, SEQ ID NO: 46, complement thereof, or variant thereof.

In other embodiments, the method may include administering to the subject a pharmaceutically effective amount of an agent that reduces the interaction of a ZNF274 protein with a ZNF274 binding site on maternal chromosome 15 at position 15q11-q13 of the subject relative to a control, wherein the ZNF274 binding site comprises a polynucleotide having at least 90% sequence identity to SEQ ID NO: 1, SEQ ID NO: 42, SEQ ID NO: 43, SEQ ID NO: 44, SEQ ID NO: 45, SEQ ID NO: 46, or complement thereof. In some embodiments, the agent comprises a sequence-specific nuclease, or a polynucleotide sequence encoding a sequence-specific nuclease. In some embodiments, the sequence-specific nuclease comprises a zinc finger nuclease, a TAL effector nuclease, or a CRISPR/Cas9 DNA targeting system.

In some embodiments, the expression of at least one gene within 15q11-q13 is increased. In some embodiments, the expression of at least one gene within the Prader-Will Syndrome critical region (PWSCR) of 15q11-q13 is increased. In some embodiments, the expression of at least one RNA transcript selected from the genome coordinates hg19 chr15:25,012,961-25,685,253 or chr15:23,695,603-25,026,558 is increased. In some embodiments, the expression of at least one RNA transcript selected from SNORD116, IPW, SNORD115, SNHG14, UBE3A-ATS, or a combination thereof, is increased. In some embodiments, the expression of at least one of SNRPN exon 2, SNRPN exon 3, SNRPN exon 4, UBE3A, MAGEL2, MKRN3, SNRPN exon U4, NDN, or a combination thereof, is increased. In some embodiments, the initiation of transcription from the SNRPN U1A promoter, the SNRPN U1B promoter, or a combination thereof, is increased. In some embodiments, the binding of H3K9me3 is reduced.

b) Methods for Screening

Further provided herein is a method of screening compounds for treating a disorder of genomic imprinting. Agents may be selected or designed based on their ability to interfere with ZNF274 binding to the ZNF274 binding site, and thereby activate the maternal PWSCR RNA transcripts.

12. EXAMPLES

Example 1

Materials and Methods

Culture conditions of iPSCs and neuronal differentiation. iPSCs were grown on irradiated mouse embryonic fibroblasts and fed daily with conventional hESC medium composed of DMEM-F12 supplemented with knock-out serum replacer, nonessential amino acids, L-glutamine, β-mercaptoethanol, and basic FGF. iPSCs were cultured in a humid incubator at 37° C. with 5% $CO_2$ and manually passaged once a week.

Neuronal differentiation of iPSCs was performed using a monolayer differentiation protocol with some modifications. Briefly, iPSC colonies were cultured in hESC medium for 24 h before switching to N2B27 medium. Cells were fed every other day with N2B27 medium containing Neurobasal Medium, 2% B-27 supplement, 2 mM L-glutamine, 1% Insulin-transferrin-selenium, 1% N2 supplement, 0.5% Penstrep, and was supplemented with fresh noggin at 500 ng/mL. After three weeks of neural differentiation, neural progenitors were plated on tissue culture plates coated with poly-ornithine/laminin. The neural differentiation medium consisted of Neurobasal Medium, B-27 supplement, nonessential amino acids, and L-glutamine, and was supplemented with 1 μM ascorbic acid, 200 μM cyclic adenosine monophosphate, 10 ng/mL brain-derived neurotrophic factor, and 10 ng/mL glial-derived neurotrophic factor. Unless otherwise specified, cells were harvested once neural cultures reached at least 10 weeks of age.

Lentiviral production, transduction, and clone screening. sgRNAs were designed using a web-based CRISPR design tool and cloned into lentiCRISPR (Addgene Plasmid 49535 and 52961; Addgene, Watertown, MA) and lentiGuidePuro (Addgene Plasmid 52963, Addgene, Watertown, MA). Lentiviral particles were made by transfecting 293FT cells with $2^{nd}$ generation packaging systems using Lipofectamine 2000 (Life Technologies, Carlsbad, CA). Prior to transduction, iPSCs were treated with 10 µM ROCK inhibitor, Y-27632, overnight. The next day, iPSCs were singlized using Accutase (Millipore, Burlington, MA) and transduced with lentivirus in suspension in the presence of 8 µg/mL polybrene in a low-attachment dish for two hours. Then, the iPSCs/lentivirus mixture were diluted 1:1 in hESC medium and plated on puromycin-resistant (DR4) MEF feeders at a low density, supplemented with 10 µM ROCK inhibitor, Y-27632, overnight. Attached cells were cultured in hESC medium for an additional 72 hours before starting drug selection using puromycin at 0.5 µg/mL during the first week and at 1 µg/mL during the second week. Puromycin-resistant iPSC colonies were individually picked into a new feeder well and screened for indels by performing PCR on genomic DNA and sequencing. The pluripotency of gene edited iPSCs was validated by immunocytochemistry using mouse anti-human stage specific embryonic antigen 4 (SSEA4) and rabbit anti-human OCT3/4, both from Molecular Probes (Eugene, OR), as previously described (Chen, et al. *Sc. Rep.* 2016, 6, 25368). Karyotyping and Affymetrix HD 6.0 array were performed by the Genetics and Genomics Division of the UCONN Stem Cell Core. Twenty G-banded metaphase cells from each iPSC line were examined to generate a karyotype for each line.

CRISPRs were transiently introduced by nucleofecting hESCs engineered to have PWS-like deletions (deletion of paternal SNORD116 or deletion of paternal SNRPN to SNORD116) or PWS iPSCs with two constructs carrying Cas9, gRNAs targeting ZNF274 or ZNF274 binding sites, and a puromycin resistance cassette. The hESC/iPSCs are selected for 48 hours with puromycin and resulting clones are screened for specific deletions using PCR spanning the deletion breakpoints.

RNA isolation and RT reaction. RNA was isolated from cells using RNA-Bee (Tel Test, Inc., Friendswood, TX). Samples were DNase-treated as needed with Amplification Grade DNaseI (Invitrogen, Carlsbad, CA) at 37° C. for 45 minutes, and cDNA was synthesized using the High Capacity cDNA Reverse Transcription Kit (Life Technologies, Carlsbad, CA) according to the manufacturer's instructions.

RT-qPCR and expression arrays. For single gene expression assay, expression levels of target genes were examined using TaqMan Gene Expression Assays (Applied Biosystems, Foster City, CA) on the Step One Plus (ThermoFisher Scientific, Waltham, MA) or on the BioRAD CFX96 Real Time PCR system (Bio-Rad Laboratories, Hercules, CA). An amount of RT reaction corresponding to 30 ng of RNA was used in a volume of 20 ul per reaction. Reactions were performed in technical duplicates or triplicates and the GAPDH Endogenous Control TaqMan Assay was used as an endogenous control, following the manufacturer's protocol. Relative quantity (RQ) value was calculated as $2^{-\Delta\Delta Ct}$ using the normal cell lines CTRL1 or CTRL2 as the calibrator sample.

Taqman Low Density Array (TLDA) technology was used to investigate gene expression levels over the entire 15q11.2-q13 region in our 10-week-old neurons. A custom-formatted Taqman low-density arrays (TLDA) was designed with 48 target genes, including two housekeeping genes, allowing for 8 samples (including CTRL2) per card. All primer/probe sets are inventoried in TABLE 8. Gene expression assays were supplied by Applied Biosystems (Foster City, CA). For TLDA analysis, 400 ng of DNAsc-treated RNA was used per RT reaction, according to the manufacturer's directions. A cDNA sample, equivalent to 150 ng effective RNA, ribonuclease-free water, and PCR master mix were loaded into each TLDA-card fill port. The samples were distributed on the plate by centrifugation. Real-time PCR was performed on the 7900HT or ViiA7 Real-Time PCR systems (Applied Biosystems, Foster City, CA). The same CTRL2 sample as our calibrator or Internal Positive Control (IPC) was systematically loaded into each card, and the Thermo Fisher Cloud interface was used to analyze the data with the IPC settings to normalize Cq values across the different plates.

Chromatin Immunoprecipitations. ChIP assays were performed as described (Cruvinel, et al. *Hum. Mol. Genet.* 2014, 23, 4674-4685; Cotney, et al. *Cold Spring Harb. Protoc.* 2015, 191-199; Martins-Taylor, et al. *Epigenetics* 2012, 7, 71-82). The antibodies anti-ZNF274 (Abnova, Cat #H00010782-M01; Abnova, Taiwan) and anti-trimethyl histone H3 (Lys9) (H3K9mc3; Millipore, Cat #07-442; Millipore, Burlington, MA) were used. Quantification of ChIPs was performed using SYBR Green quantitative PCR. PCR primers used to amplify the purified DNA can be found in TABLE 2. The enrichment of the DNA was calculated as percent input, as previously described (Martins-Taylor, et al. *Epigenetics* 2012, 7, 71-82). Normal rabbit IgG was used for the isotype controls and showed no enrichment. Data were presented as means with SD and represent the average of at least two biological replicates from independent cultures.

Detection of 5hmc levels. Percentages of 5-methyleytosine (5mC), 5-hydroxymethylcytosine (5hmC) and unmodified cytosine (C) in DNA were assessed using the EpiMark 5-hmC and 5-mC Analysis Kit (New England Biolabs, Ipswich, MA; catalog #E33I 7S). qPCR primers used in these assays are denoted in TABLE 2. TABLE 2 lists the SYBR primers sequences used. Reported values represent the average of at least two independent experiments, each analyzed in triplicate by quantitative PCR. Data were presented as means and SD of independent experiments.

Statistical tests. Statistical analysis was carried out using Prism software (GraphPad). For each condition shown, averaged values from a minimum of two biological replicates from independent cultures were calculated and the resulting standard deviation (SD) was reported in the error bars. Unless otherwise specified, for each experiment, averaged values for each sample were compared to that of the parental PWS cell line of the same genotype (PWS LD or PWS UPD) and the significance for each un-manipulated vs. KO pair was calculated using the one- or two-way analysis of variance (ANOVA) with the Dunnett post-test.

TABLE 2

Primers designed for ChIP and 5 mC analyses

| Name | Primer | SIZE (BP) | Use |
|---|---|---|---|
| SNOG1-BS1 | Forward 5'→3' (SEQ ID NO: 28) GAGTGAGGGACAACTTCCACTGA Reverse 5'→3' (SEQ ID NO: 35) TCCCACCCATGTACCTCACA | 120 | ChIP-qPCR |

TABLE 2-continued

Primers designed for ChIP and 5 mC analyses

| Name | Primer | SIZE (BP) | Use |
|---|---|---|---|
| SNOG1-BS2 | Forward 5'→3' (SEQ ID NO: 29) AACTGAGGTCCAGCACATTGCC Reverse 5'→3' (SEQ ID NO: 36) GTGCCTGTGATGTGAGACTTTCA | 120 | ChIP-qPCR |
| SNOG1-BS3 | Forward 5'→3' (SEQ ID NO: 30) TCTTCAAATGTGCTTGGATCGA Reverse 5'→3' (SEQ ID NO: 37) GCAACGTGCTGGACCTCAGT | 120 | ChIP-qPCR |
| SNOG1-BS4 | Forward 5'→3' (SEQ ID NO: 31) TGCCTCTTCGAACGTGCTT Reverse 5'→3' (SEQ ID NO: 38) CGTGCTGGACCTCAGTTCTG | 120 | ChIP-qPCR |
| SNOG1-BS5 | Forward 5'→3' (SEQ ID NO: 32) GGCATCCACAGGCCAAAGT Reverse 5'→3' (SEQ ID NO: 39) CCATGGCTGCCACACCATA | 120 | ChIP-qPCR |
| SNOG1-BS6 | Forward 5'→3' (SEQ ID NO: 33) TGAGGGTGTCTTTGGGATTCC Reverse 5'→3' (SEQ ID NO: 40) AGCTGTGCCACTGAGCAAAA | 120 | ChIP-qPCR |
| PWS-IC | Forward 5'→3' (SEQ ID NO: 34) ATCTGTCTGAGGAGCGGTCAGT Reverse 5'→3' (SEQ ID NO: 41) TCCCCAGGCTGTCTCTTGAG | 84 | 5hmC-qPCR |

Example 2

Generation and Characterization of ZNF274 KO Lines

Figure 8A:
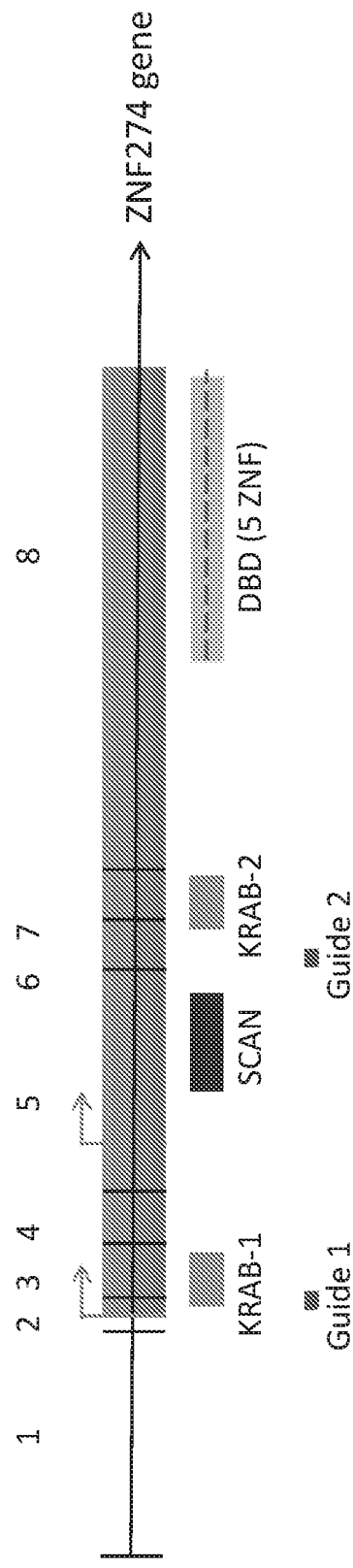
FIGS. 8A-8B show stem cell model generation.
Figure 8B:
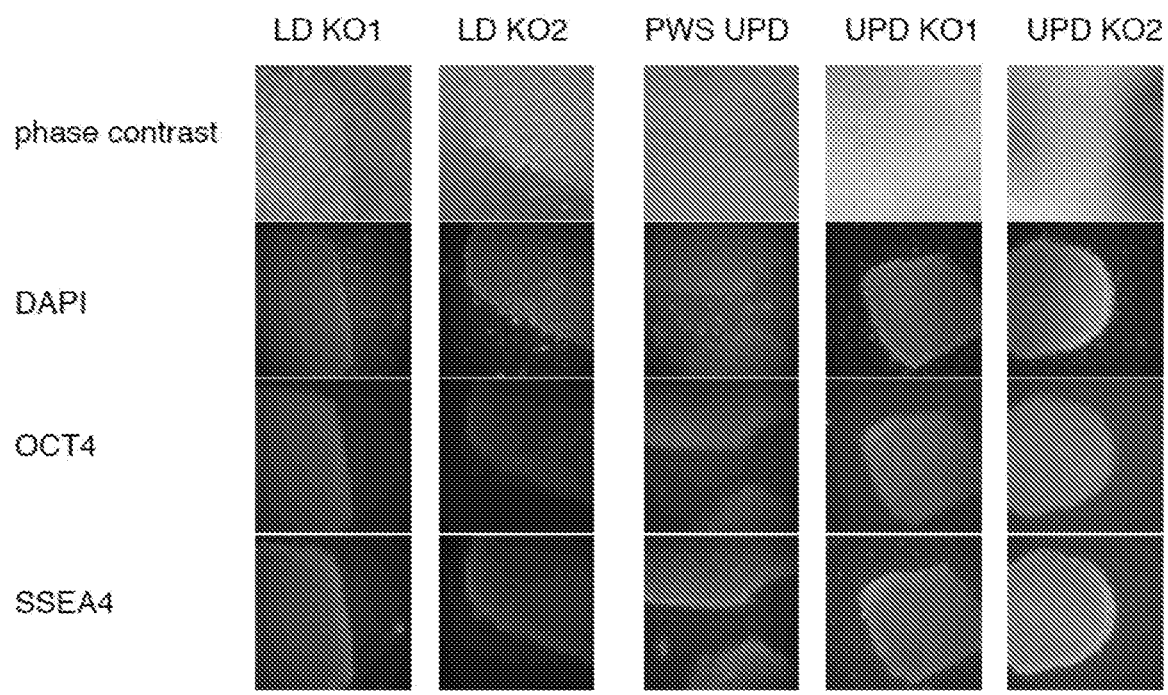

In addition to the previously characterized PWS LID iPSCs (Chamberlain, et al. Proc. *P Natl. Acad. Sci. USA* 2010, 107, 17668-17673), iPSC lines were generated from a PWS UPD patient (FIG. 8B and TABLE 3).

TABLE 3

Karyotyping and Affymetrix HD 6.0 array

| | Analysis | |
|---|---|---|
| cell lines | Karyotype | Affymetrix HD 6.0 array |
| PWS LD | 46, XX | Previously published |
| LD KO1 | 46, XX | arr[hg19] 15q11.2q13.1 (23,286,571-28,644,578) × 1 |
| LD KO2 | 46, XX | arr[hg19] 15q11.2q13.1 (23,286,571-28,659,911) × 1 |
| PWS UPD | 46, XX | na |
| UPD KO1 | 46, XX | na |
| UPD KO2 | 46, XX | na |
| UPD KO3 | 46, XX | na |

CRISPR/Cas9-mediated knockout of ZNF274 was performed in PWS-specific iPSCs in order to determine the impact of ZNF274 depletion on H3K9me3 accumulation at the SNORD116 locus. CRISPR/Cas9-mediated knockout of ZNF274 was performed in PWS LD and PWS UPD, by designing two different single guide RNAs (sgRNAs), in exon 2 and 6 of the ZNF274 gene (NM_133502) to target the two major isoforms of ZNF274 (FIG. 8A; TABLE 4). 5 clonal iPSC clones were selected after screening for non-homologous end-joining-mediated insertions/deletions (indels) resulting in a frameshift and a premature stop codon (Shalem et al., Science, 342:84-87 (2014)). As an additional control for lentiviral transduction and CRISPR/Cas9 integration and expression in the PWS LD line, a previously validated scrambled sgRNA that has no match in the human genome was used (TABLES 4 and 5). A clonal derivative, PWS LD sc1, was selected to confirm that introduction of the CRISPR constructs did not affect gene expression in the parental PWS LD line.

TABLE 4 sgRNA sequences

| | Sequence | PAM used | sense/anti-sense | Targeting exon in NM_133502 |
|---|---|---|---|---|
| ZNF274 Guide-1 | CCTCCAGGCTTCCGACGGCC (SEQ ID NO: 13) | TGG | sense | exon 2 |
| ZNF274 Guide-2 | CCTGCAGGACAACCTGCCGA (SEQ ID NO: 14) | GGG | sense | exon 6 |
| Scramble Guide | CAGTCGGGCGTCATCATGAT (SEQ ID NO: 15) | none | none | none |

TABLE 5

Transduced cell lines information

| Cell lines | Guide RNA |
|---|---|
| NM1 | none |
| NM2 | none |
| PWS LD | none |
| PWS LD sc1 | Scramble Guide |
| LD KO1 | ZNF274 Guide-1 and-2 |
| LD KO2 | ZNF274 Guide-2 |
| PWS UPD | none |
| UPD KO1 | ZNF274 Guide-2 |
| UPD KO2 | ZNF274 Guide-2 |
| UPD KO3 | ZNF274 Guide-2 |
| AS | none |

The genetic alterations induced by ZNF274 knockout (ZNF274 KO) are summarized in TABLE 6 for the PWS LID ZNF274 KO lines (LID K01 and LID K02) and UPD ZNF274 KO lines (UPD K01, UPD K02, and UPD K03)

TABLE 6

| | Mutations generated | | | |
|---|---|---|---|---|
| | Indels with Guide-1 | | Indels with Guide-2 | |
| Cell lines | allele 1 | allele 2 | allele 1 | allele 2 |
| LD KO1 | NM_133502: c.15_18del, p.Pro6Argfs*6 | NM_133502: c.14_23del, p.Leu5Profs*5 | NM_133502: c.757_763delins GA, p.Pro253Glufs*30 | NM_133502: c.761dup, p.Glu255Argfs*30 |
| LD KO2 | none | none | NM_133502: c.761_762insA, p.Glu255Argfs*30 | NM_133502: c.761_762insA, p.Glu255Argfs*30 |
| UPD KO1 | none | none | NM_133502: c.761_762insA, p.Glu255Argfs*30 | NM_133502: c.753_766del, p.Gln252Hisfs*27 |
| UPD KO2 | none | none | NM_133502: c.762_777del, p.Glu255Argfs*20 | NM_133502: c.762_777del, p.Glu255Argfs*20 |
| UPD KO3 | none | none | NM_133502: c.761_762insT, p.Glu255Argfs*30 | NM_133502: c.756_771del, p.Glu255Alafs*20 |

Karyotypic analysis of the engineered iPSC lines showed no detectable abnormalities (TABLE 3). Routine testing for pluripotency was performed (FIG. 8B), and no sequence changes within the top potential off-target loci were observed (TABLE 7).

TABLE 7

Off-target sequences predicted by the Zhang lab software (Hsu et al., Nat Biotechnol, 31:827-832 (2013)) for both ZHF274 sgRNAs, which were tested for sequence changes at and around those loci.

| | ZNF274 Guide-1 |
|---|---|
| 1 | CCTGCAGGCCTCGGACGGCCAGG (SEQ ID NO: 18) |
| 2 | CACCCAGGCCCCCGACGGCCAGG (SEQ ID NO: 19) |
| 3 | GCTCAAGTCTTCCGACCGCCAAG (SEQ ID NO: 20) |
| 4 | GCCCCAGGCCTCCGACTGCCGAG (SEQ ID NO: 21) |
| 5 | CCGCGAGGCTTCCGAGGGCCAGG (SEQ ID NO: 22) |
| | ZNF274 Guide-2 |
| 1 | TGGGCAGGAAAACCTGCCGAGGG (SEQ ID NO: 23) |
| 2 | CCTGGAGGAGAACCTGCCGTGAG (SEQ ID NO: 24) |
| 3 | CCTCAAGGACAACCTGCCCATAG (SEQ ID NO: 25) |
| 5 | CCAGCAGGTCAACCTGACGATGG (SEQ ID NO: 26) |
| 6 | CCACCAGGAAACCCTGCCGAAAG (SEQ ID NO: 27) |

Example 3

Figure 1B:
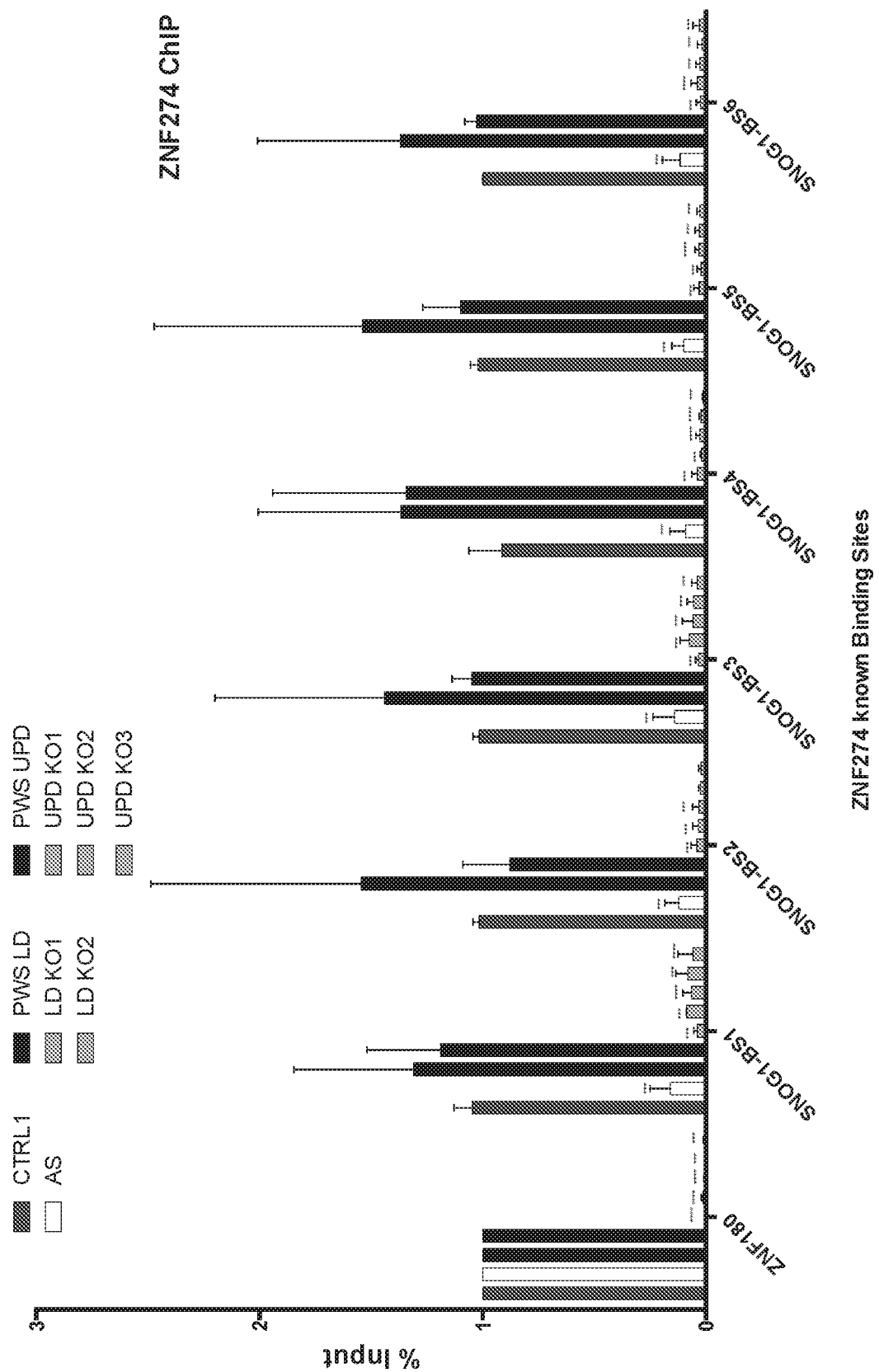
Figure 1C:
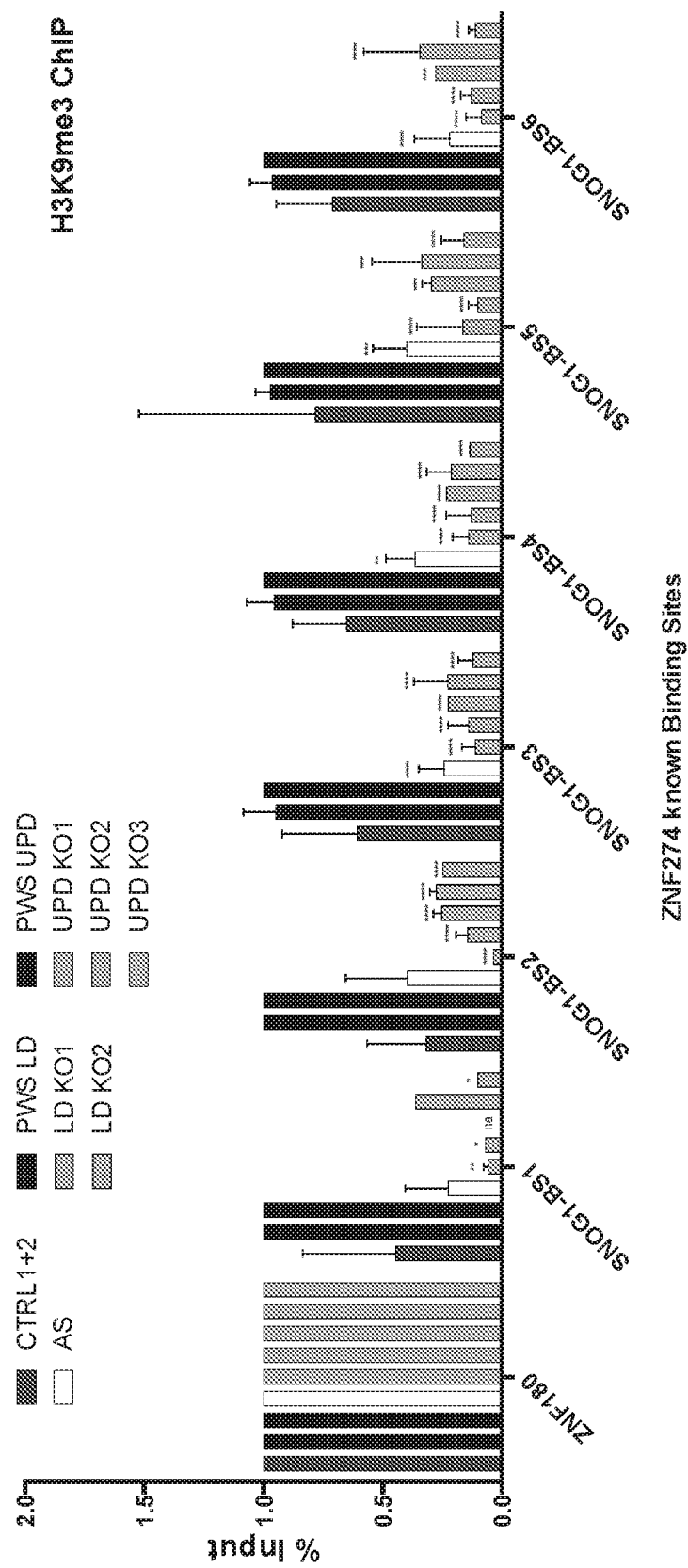
Figure 9A:
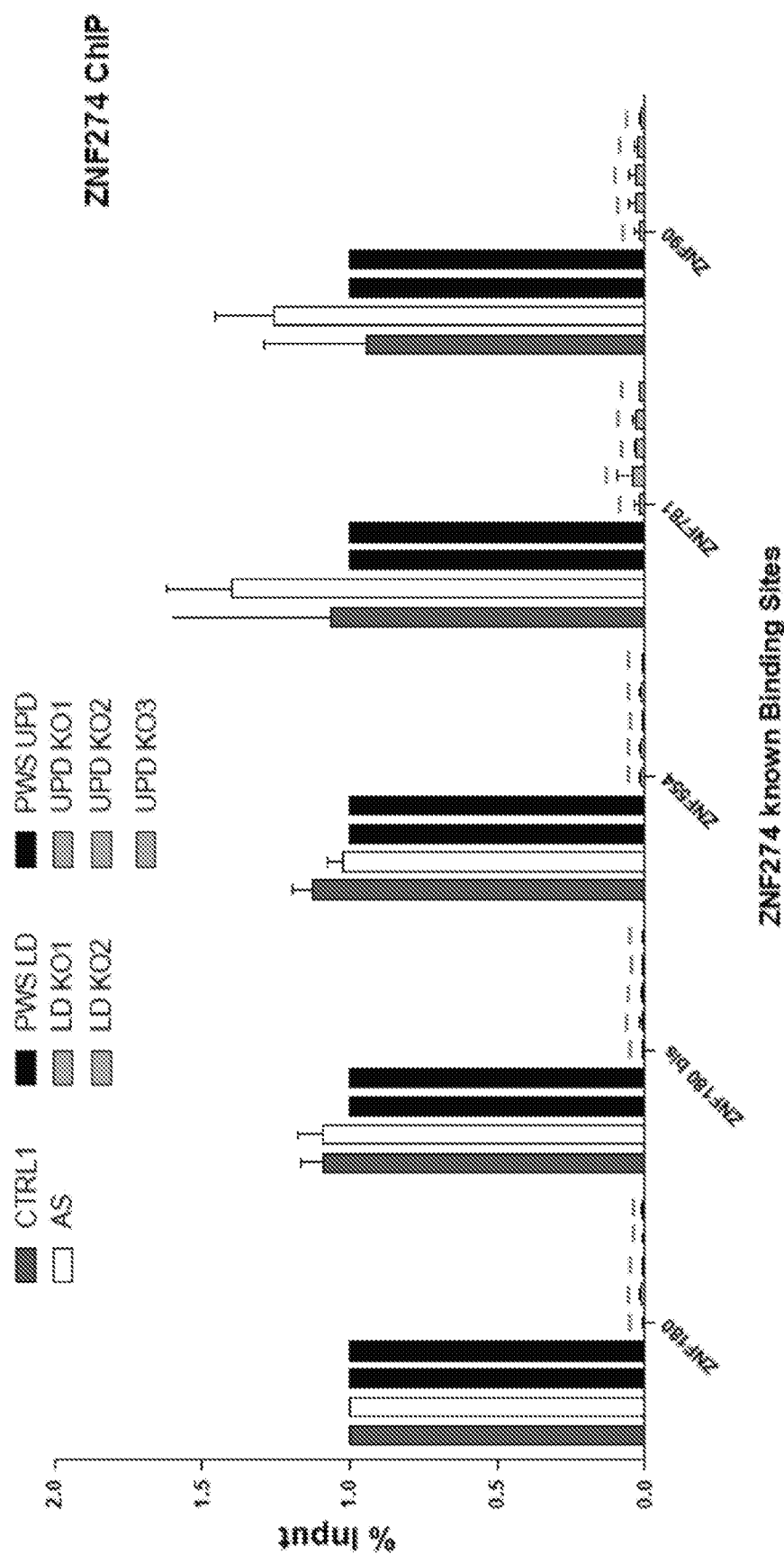
FIGS. 9A-9D show the effect of H3K9me3 accumulation upon ZNF274 KO.

CRISPR/Cas9-Mediated Knock Out of ZNF274 Depletes H3K9Me3 at the SNORD116 Locus in PWS-Specific iPSCs Chromatin ImmunoPrecipitation (ChIP) was performed on the PWS LD and UPD iPSCs and their derivative ZNF274 KO clones as well as from iPSCs from control individuals (CTR1 and CTRL2) and an Angelman syndrome (AS) patient with a large deletion of the maternal chromosome 15q11-q13 and a complete absence of ZNF274 binding to all PWS LD and UPD ZNF274 KO clones at all the 12 known ZNF274 binding sites was observed, demonstrating an efficient ZNF274 KO (FIG. 1B and FIG. 9A). This absence of ZNF274 binding was associated with a marked reduction of H3K9me3 at the six ZNF274 binding sites (BSs) (SNOG1-BS1 to SNOG1-BS6) in all PWS LD and UPD ZNF274 KO clones, demonstrating the efficient disruption of ZNF274 function at the SNORD116 locus in the KO iPSC lines. Although a complete absence of the ZNF274 protein was observed at all the known ZNF274 BSs tested, the level of H3K9me3 was not reduced at the ZNF274 BS in the ZNF180 3'UTR that was used as a reference.

Figure 9B:
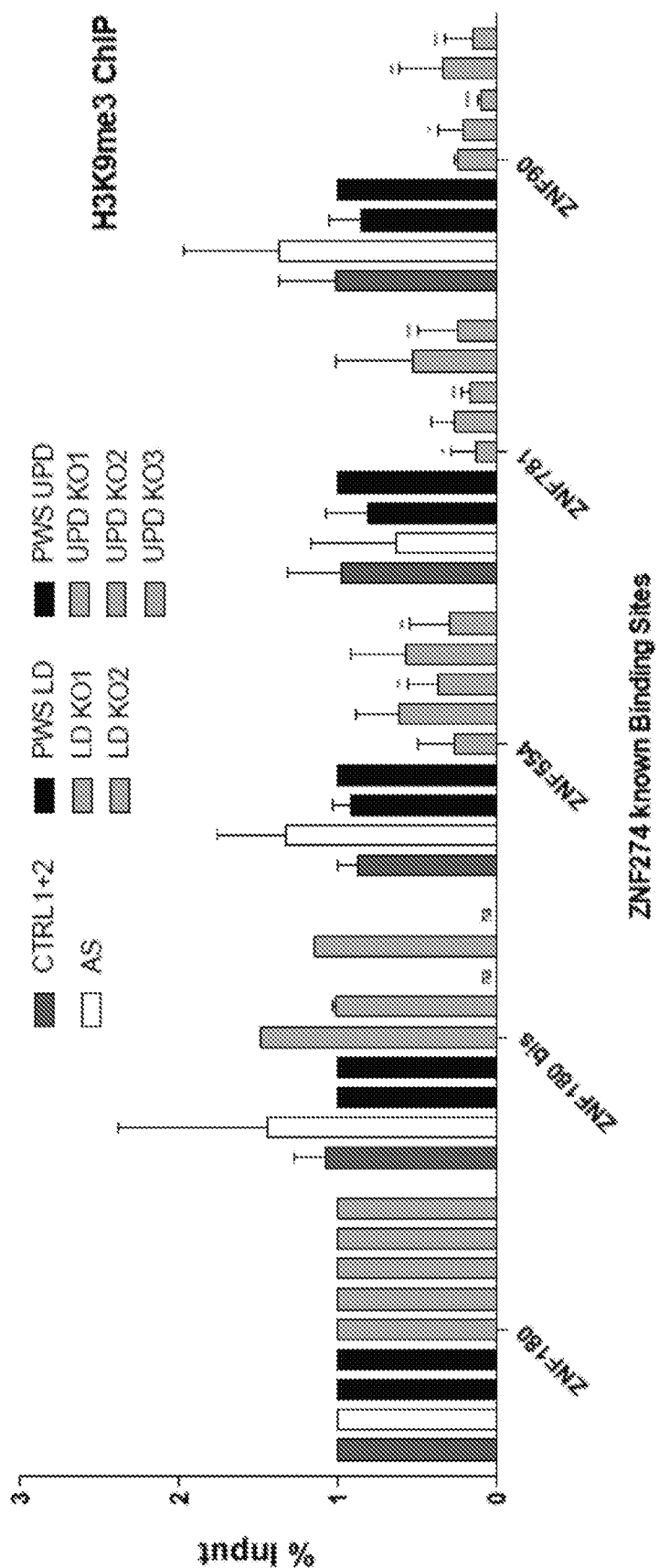
Figure 9C:
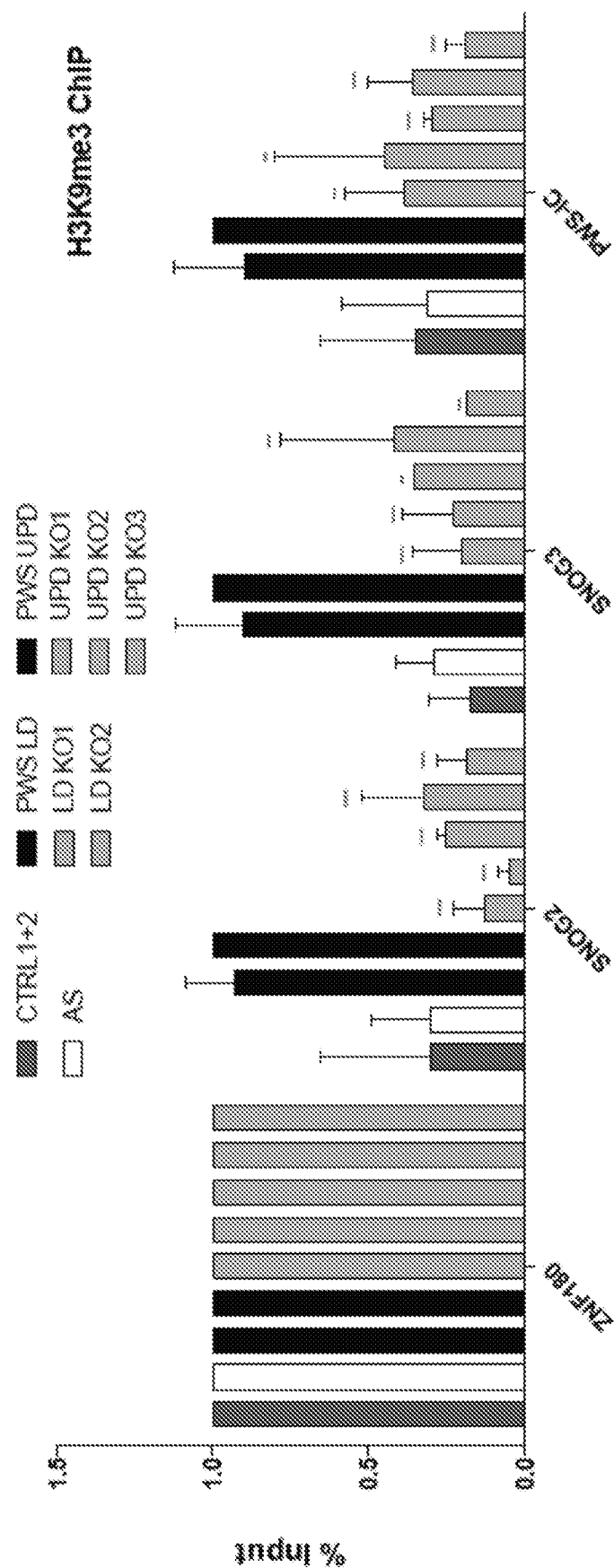
Figure 9D:
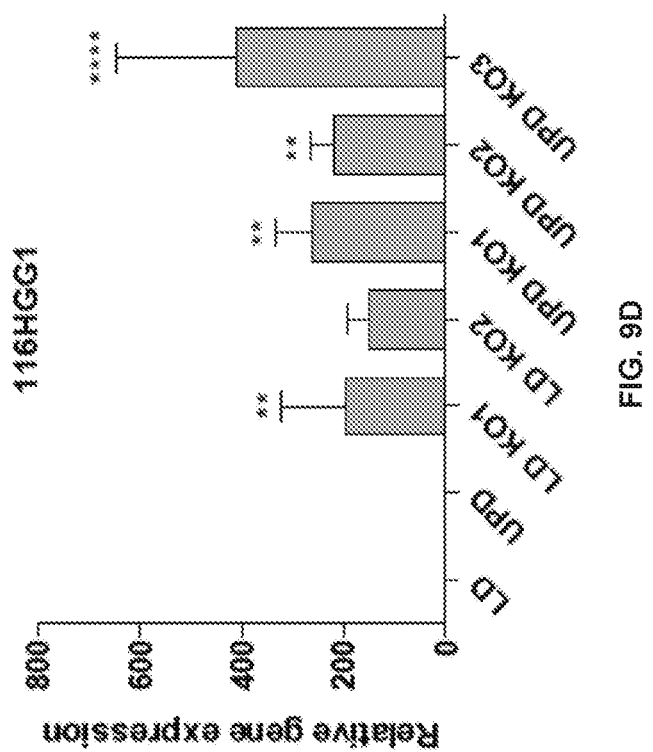

A likely explanation is that ZNF274 BSs are most often shared with a second zinc finger protein (ZNF75D). In fact, 89.1% of ZNF274 binding sites in KRAB domain-containing zinc finger protein genes are shared with ZNF75D. For example, the 3' UTR of ZNF180 and ZNF554 are two target regions bound by both ZNF274 and ZNF75D, and little or no effect on H3K9me3 levels was observed at those sites (FIG. 9B). The 3'-ends of ZNF781 and ZNF90, on the other hand, are two of the rare sites that were bound only by ZNF274 and, consistent with this observation, a more marked reduction of H3K9me3 was detected for those two BSs (FIG. 9B). The levels of H3K9me3 were also reduced in the PWS LD and UPD ZNF274 KO clones at SNOG2 and SNOG3, which are SNORD116 class group 2 and 3 loci located downstream of SNOG1-BS1 to SNOG1-BS6 (FIG. 9C). The spread of H3K9me3 deposition at the maternal-specific SNOG1 ZNF274 BSs was consistent with previous observations (Cruvinel, et al. Hum. Mol. Genet. 2014, 23, 4674-4685). A concomitant activation of expression of the SNORD116 host gene Group1 (116HGGI) transcript was observed in the ZNF274 KO PWS LD and UPD iPSCs (FIG. 9D).

These results suggested that ZNF274 KO in PWS iPSCs reduced H3K9me3, leading to chromatin de-condensation and partial transcriptional activation of 116HGGI within the PWS locus.

Example 4

Impact of ZNF274 KO on SNRPN Activation in PWS-Specific iPSCs

Figure 2A:
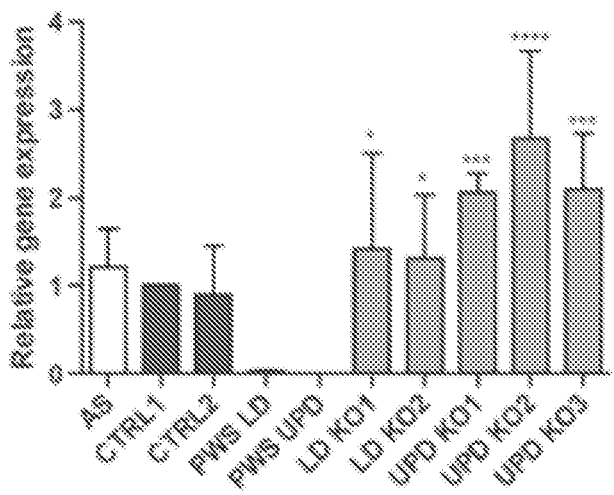
FIGS. 2A-2D show the effect of ZNF274 KO on SNRPN expression and PWS-IC methylation in iPSCs.
Figure 2B:
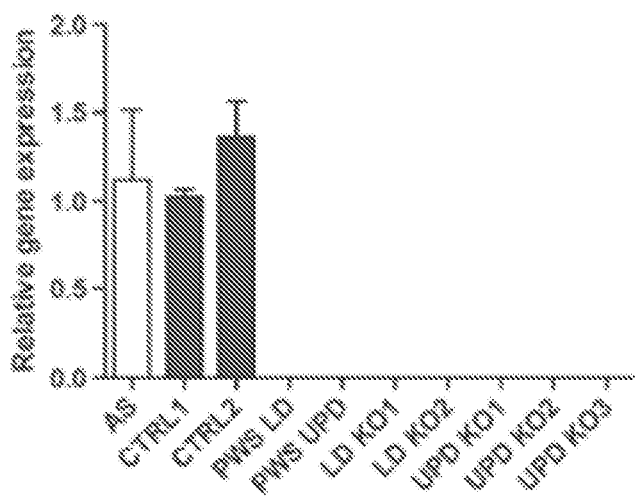
Figure 2C:
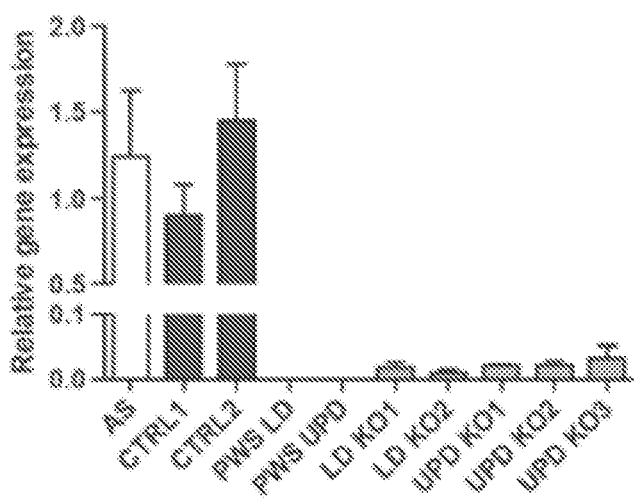
Figure 2D:
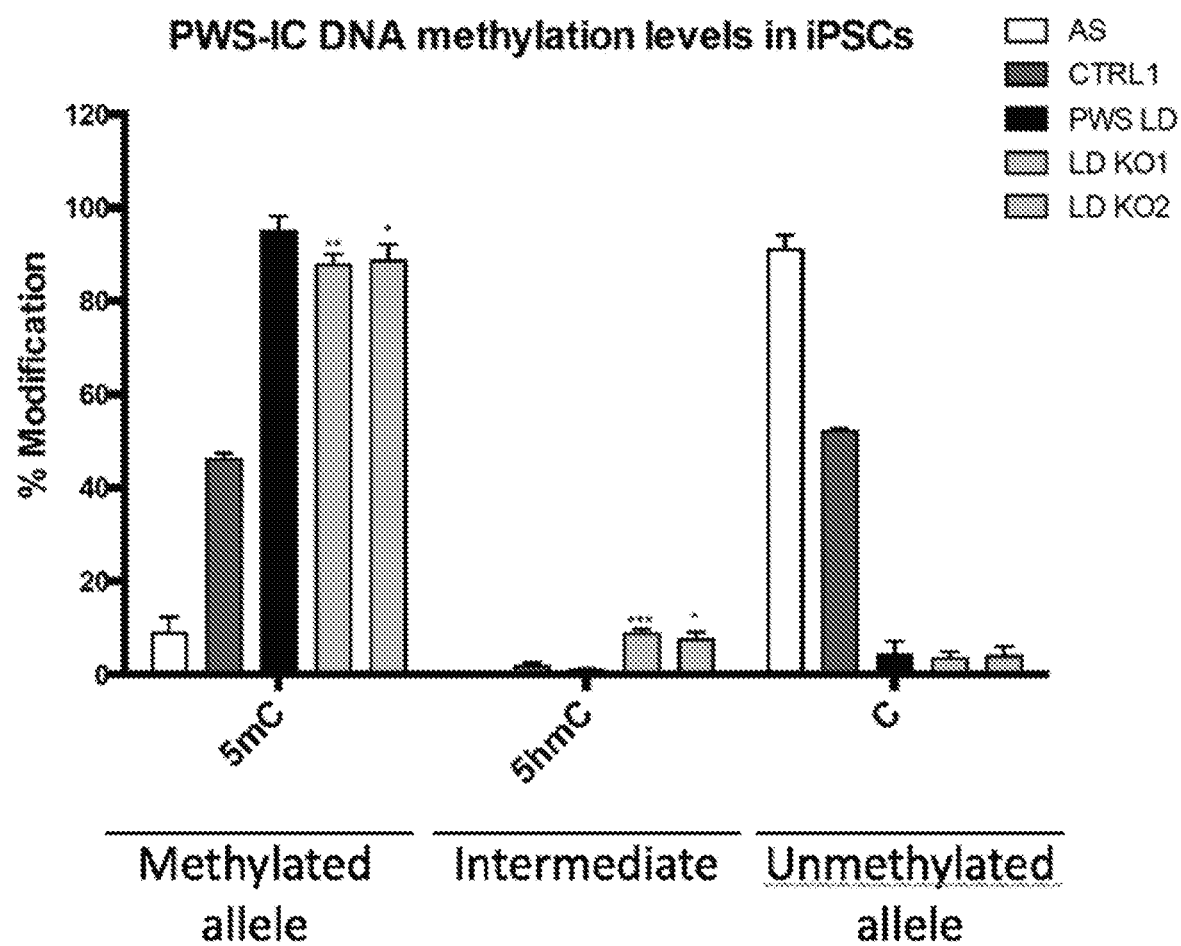

The mechanism by which ZNF274 KO activates 116HGGI expression by examining the regulatory elements of the PWS lncRNA was also investigated. For this, SNRPN transcripts driven by the major promoter in exon 1 and by its alternative upstream exon promoters, U1B and U1A, that drive PWS lncRNA predominantly in brain were analyzed. SNRPN transcripts driven by U1B and U1A skip exon 1 and splice into exon 2. We assayed for RNAs that splice from exon U4 to exon 2 since the U4 internal exon is included in most SNRPN U1B and U1A transcripts. ZNF274 KO-mediated activation of U4/exon 2 (FIG. 2A) was detected but no activation was detected of exon 1/exon 2 SNRPN transcripts (FIG. 2B), a finding that suggested that the ZNF274 complex represses maternal PWS transcripts through its action on the U1B and U1A promoters rather than the major SNRPN exon 1 promoter. Consistent with this suggestion, only partial activation of the SNRPN exon 3-4 coding transcript was detected (FIG. 2C) in the absence of SNRPN major exon 1 promoter usage (FIG. 2B). To further understand the impact of ZNF274 KO on the regulation of SNRPN and PWS, DNA methylation in the PWS-IC, which is contained within SNRPN exon 1 (FIG. 2D) was examined. In PWS LD iPSCs and their ZNF274 KO derivatives, almost identical levels of CpG methylation at the maternal PWS-IC (FIG. 2O) were observed. These findings were not only consistent with the observation that the maternal SNRPN exon 1 promoter was not activated by ZNF274 KO but suggested, importantly, that ZNF274 is an epigenetic regulator of chromosome 15q11-q13 imprinting that acts independently of the PWS-IC.

Example 5

ZNF274 KO Restores Maternal Gene Expression in PWS Neurons

Figure 3A:
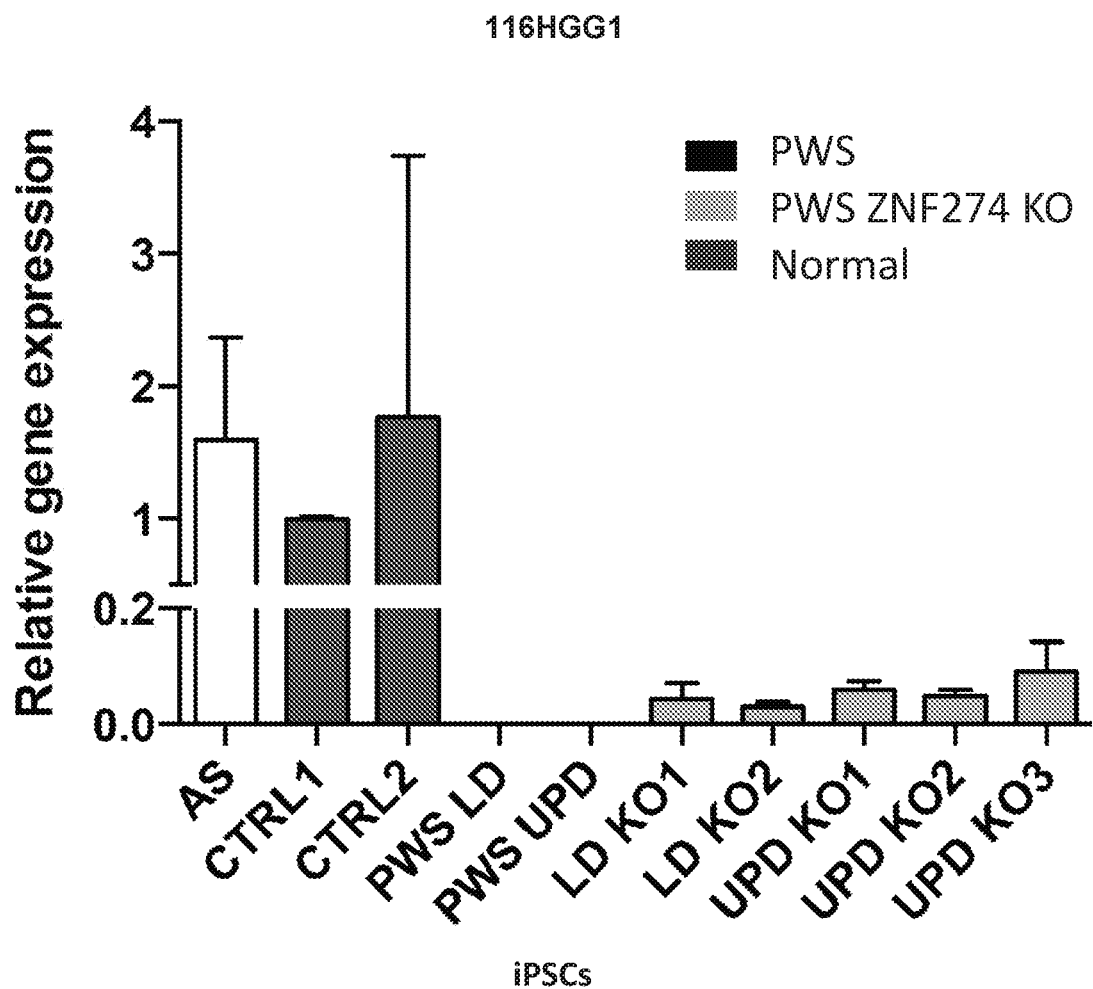
FIGS. 3A-3C show ZNF274 KO-mediated activation of maternal 116HGGJ transcripts during in vitro neurogenesis. Gene expression of the SNORD116 Host Gene Group I (116HGGI) in each cell line through the differentiation process: in (FIG. 3A) iPSCs (n=3 minimum), (FIG. 3B) 4-week-old neural precursor cells (NPCs) (n=1 minimum), and (FIG. 3C) mature 10-week-old neurons (n=2 minimum). The same color code as in FIG. 1B is used. Data were normalized to CTRL1 or CTRL2 for each panel and plotted as the mean with Standard Deviation (SD). Significance was calculated using one-way analysis of variance (ANOVA) test with a Dunnett post-test to compare the two LD KOs to PWS LD and the three UPD KOs to PWS UPD.
Figure 3B:
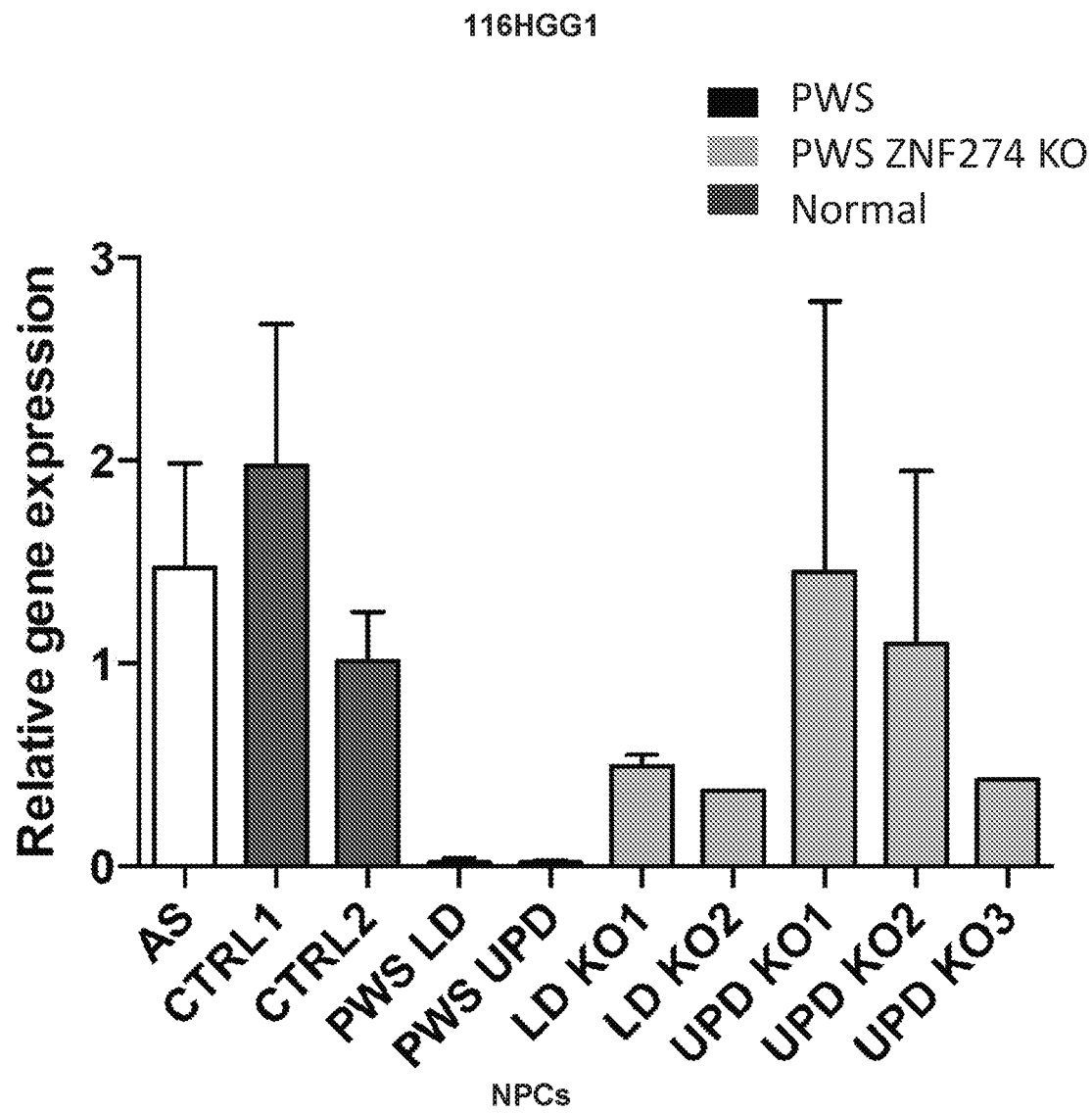
Figure 3C:
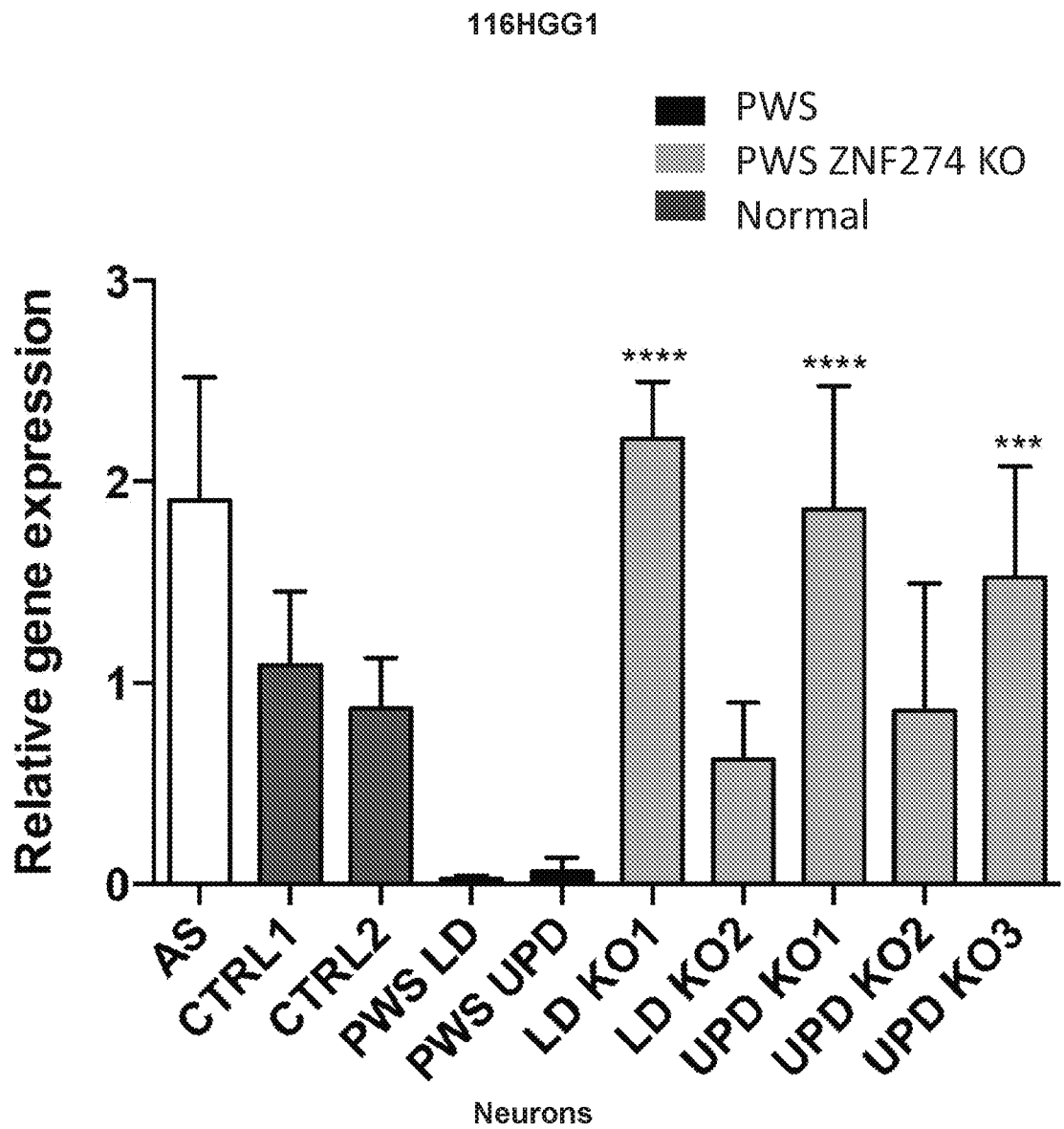

Given that the SNRPN exon U1B and U1A are active mainly in the brain, neural progenitor cells (NPCs) and neurons were derived from the iPSC lines to further understand the mechanism of the rescue of maternal PWS transcripts by ZNF274 KO (FIG. 3). Although ZNF274 KO increased the expression of maternal 116HGGI by ≥100× in PWS iPSCs (FIG. 9D), the levels attained were much lower than those in CTRL iPSC lines for 116HGGI (FIG. 3A). However, a more robust activation was observed upon neural differentiation with 116HGGI expression almost reaching control levels in ZNF274 KO NPCs and attaining or surpassing these in rescued neurons (FIG. 3B and FIG. 3C). ZNF274 KO in PWS LD and UPD lines resulted in a marked increase of 116HGGI expression relative to CTRL lines after 4 weeks of differentiation (FIG. 3B) and restored normal levels of expression in neurons after 10 weeks of differentiation (FIG. 3C).

Figure 4A:
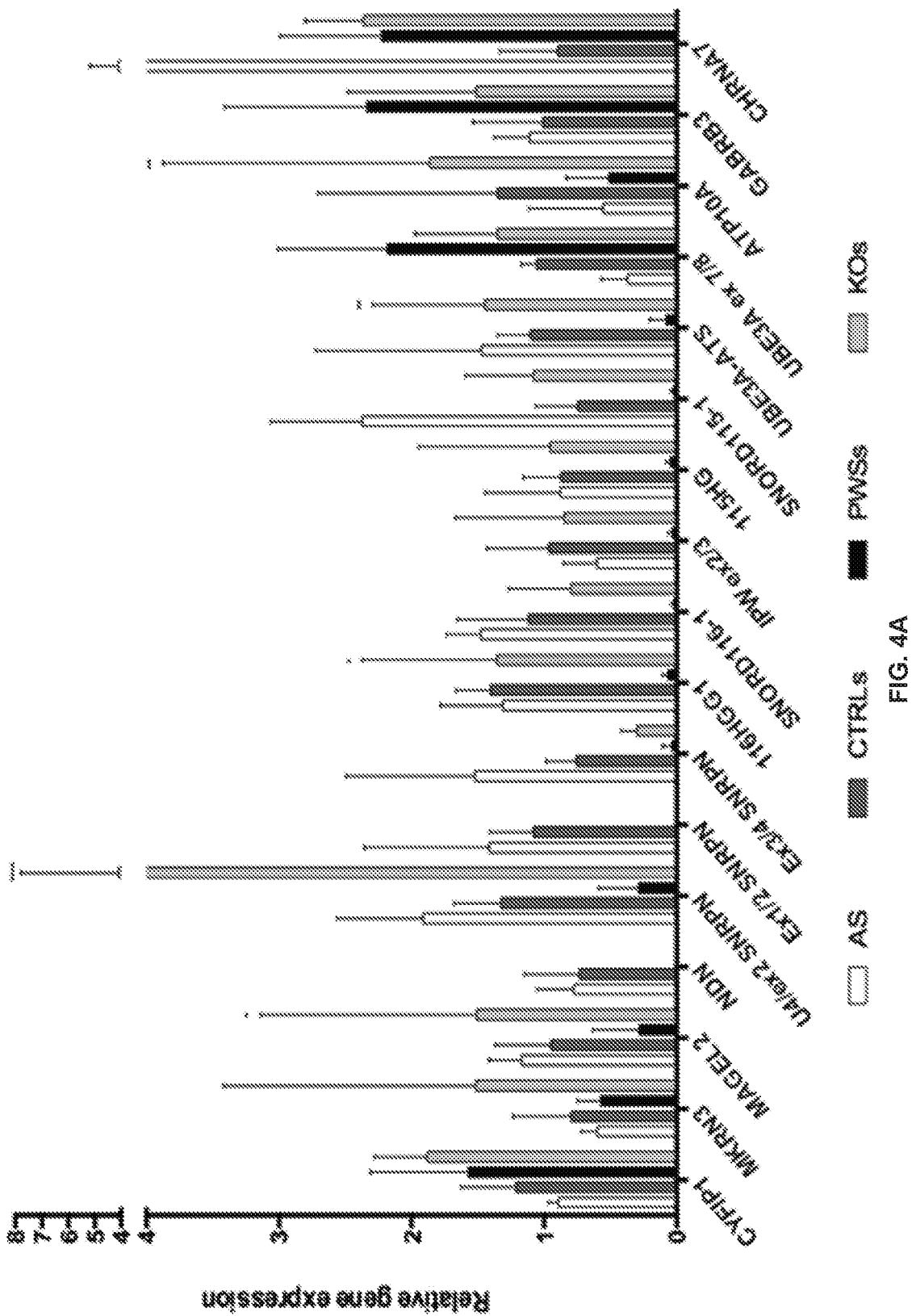
FIGS. 4A-4C show ZNF274 KO activates transcription in PWS neurons across chromosome 15q11.2-q13. Gene expression of 17 transcripts across the 15q11.2-q13 region in mature 10-week-old neurons. qRT-PCR data was combined from two normal cell lines (CTRLs) and ZNF274 KO from each parental line.
Figure 4B:
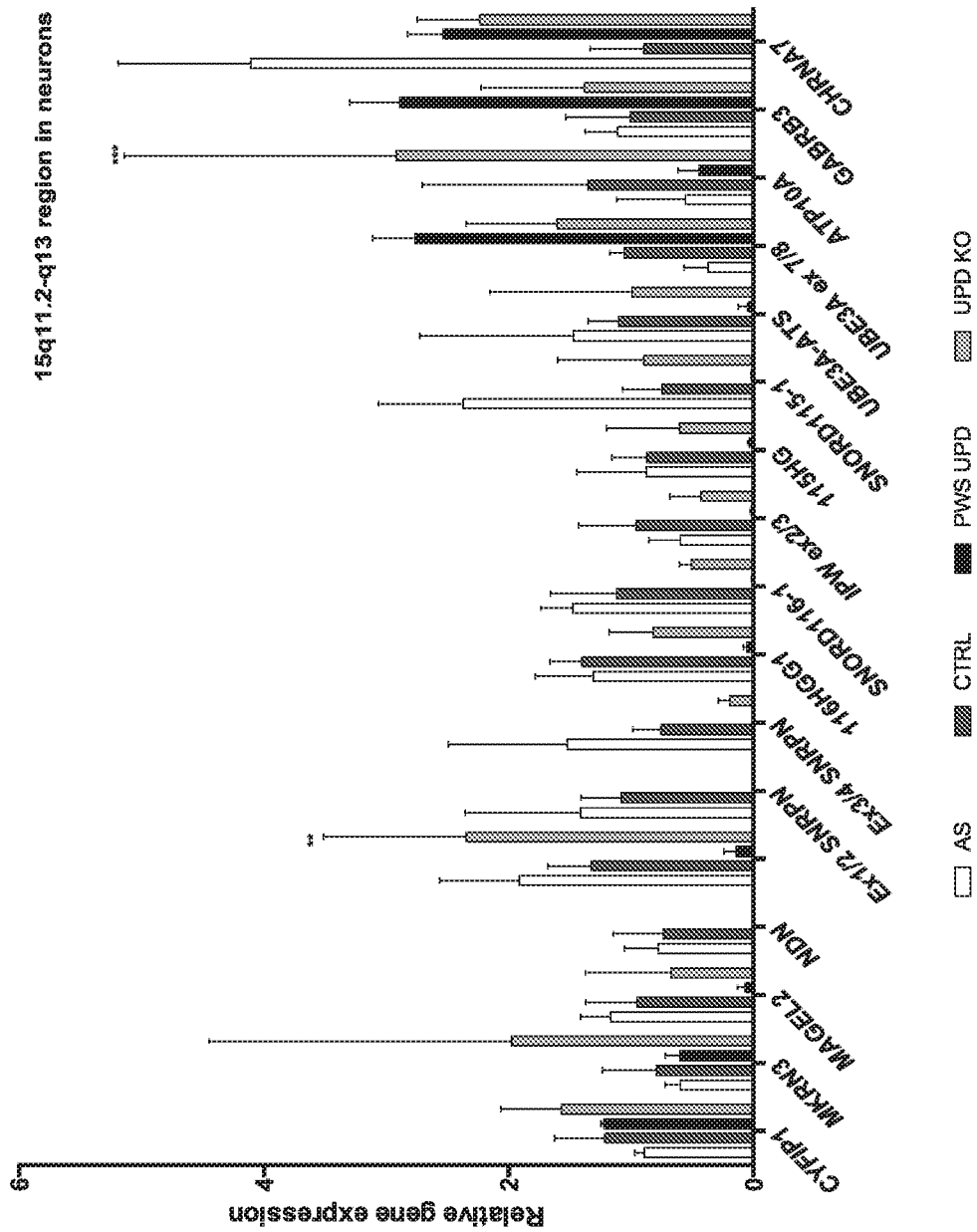
Figure 4C:
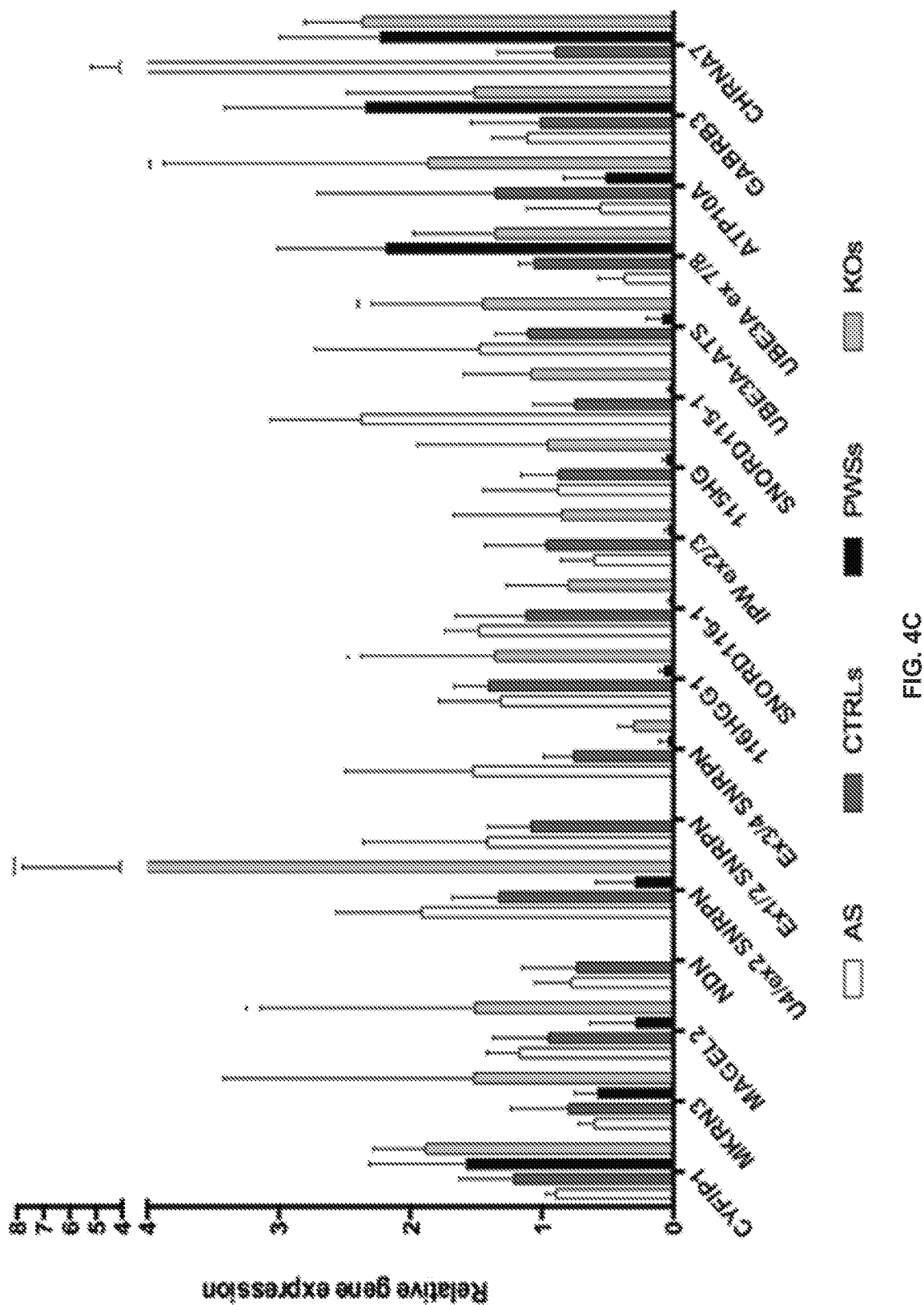

The expression of transcripts across chromosome 15q11-q13 was examined in iPSC-derived neurons from PWS LD and UPD, their ZNF274 KO derivatives, CTRLs and the AS LD. After exclusion of failed data points, all the lines were normalized to the same sample that was run in each single array: CTRL2. To validate the expression of neuronal genes, PAX6, FOXG1, RBFOX1, RBFOX3, and SOX2 were assayed in our samples (orange rows). FIGS. 4A, 4B, and 4C show that ZNF274 KO activates the transcription in PWS neurons across chromosome 15q11.2-q13. FIG. 4A and FIG. 4B show large deletion and UPD PWS data separately while FIG. 4C shows the combined data. In FIGS. 4A, 4B, and 4C, the AS in white and CTRLs in blue showed expected expression coming from the paternal allele, whereas PWSs in black and KOs in green showed expected expression coming from the maternal allele. With the KOs in green, there was expression of the majority of the 15q11-q13 region which indicated the general reactivation of the 15q11-q13 region from the maternal allele. Most of the transcripts of the 15q11-q13 region were re-expressed in ZNF274 KO PWS neurons with the exception of 2 transcripts. One of them was SNRPN exon1/2 transcript (no green expression=no rescue of this transcript upon ZNF2754 KO). TABLE 8 shows the Taqman assay list and color code. TABLE 9 shows the Ct values list. TABLE 10 shows the RQ values list. TABLE 11 shows the RQ mean values list. TABLE 12 shows the statistics.

Like 116HGGI, other transcripts (SNORD116-1 and IPW) within the PWS locus, were expressed in ZNF274 KO neurons at the same level as those in CTRL neurons (FIG. 4 and TABLES 8-12). Similar levels of ZNF274 KO-mediated reactivation of maternal neuronal transcripts were also detected downstream of the PWS locus (SNORD115-1, its 115HG host gene and the antisense overlapping UBE3A, UBE3A-ATS) (FIG. 4 and TABLES 8-12). While ZNF274 KO activated neuronal UBE3A-ATS to normal levels, a concomitant decrease in UBE3A expression was not observed at least relative to normal control UBE3A mRNA levels (FIG. 4 and TABLES 8-12).

Figure 5A:
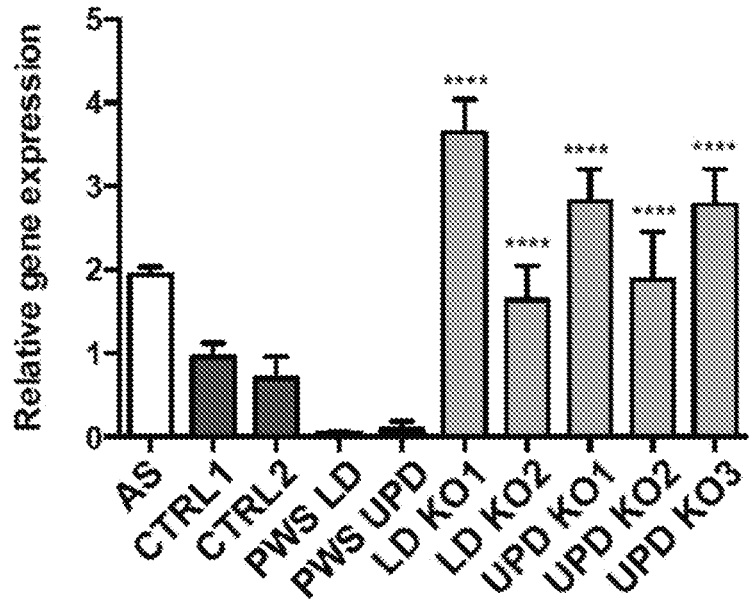
FIGS. 5A-5E show ZNF274 KO activates SNRPN upstream promoters in PWS iPSC-derived neurons without decreasing DNA methylation of the PWS-IC.
Figure 5B:
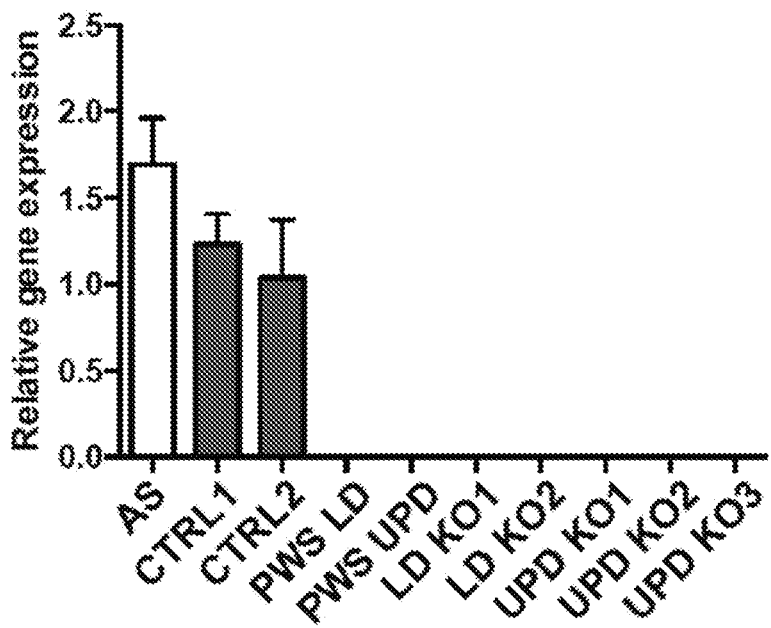
Figure 5C:
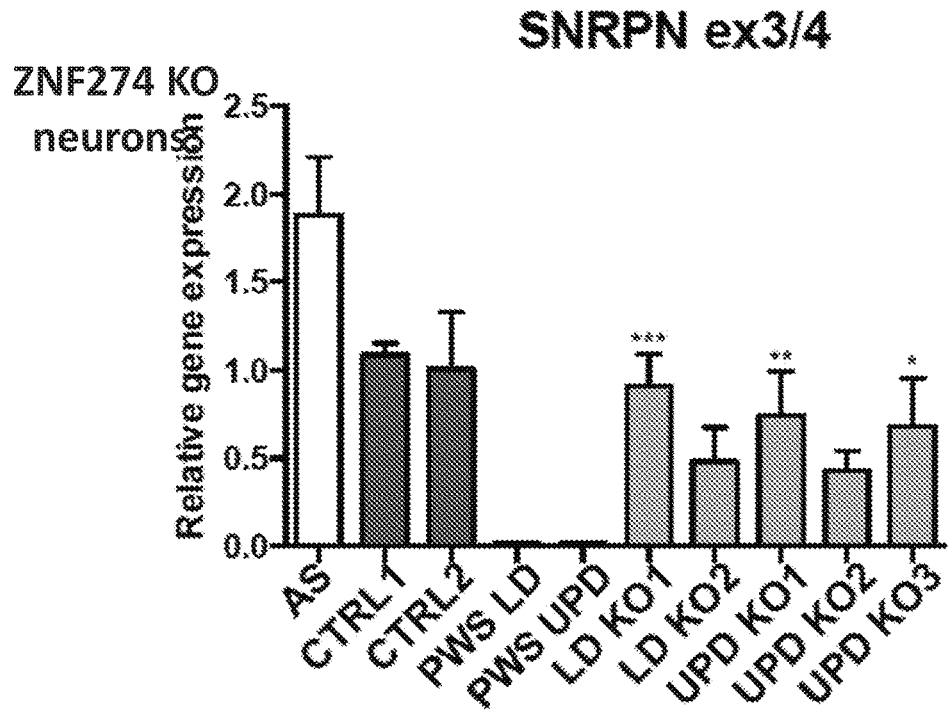
Figure 5D:
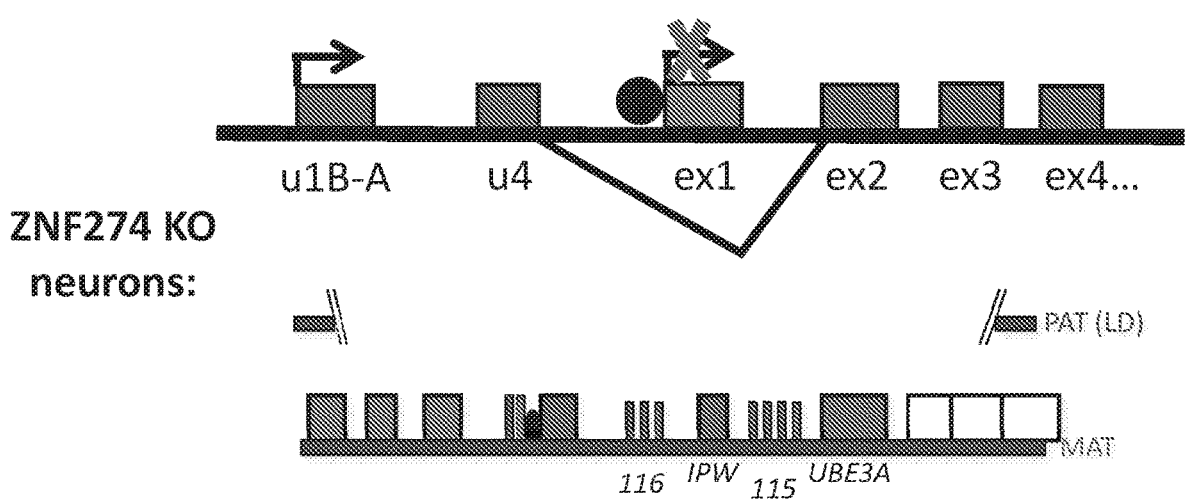
Figure 5E:
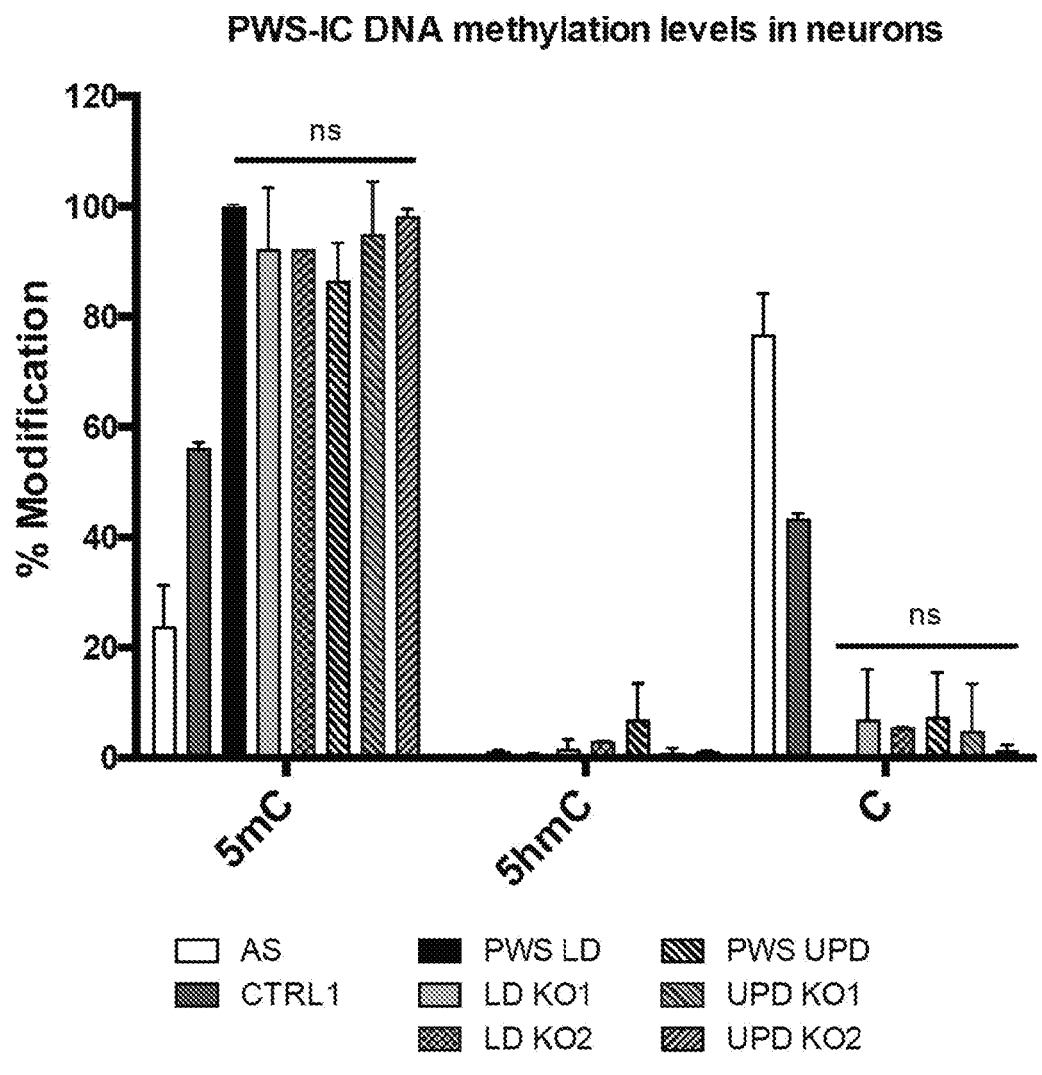
Figure 6:
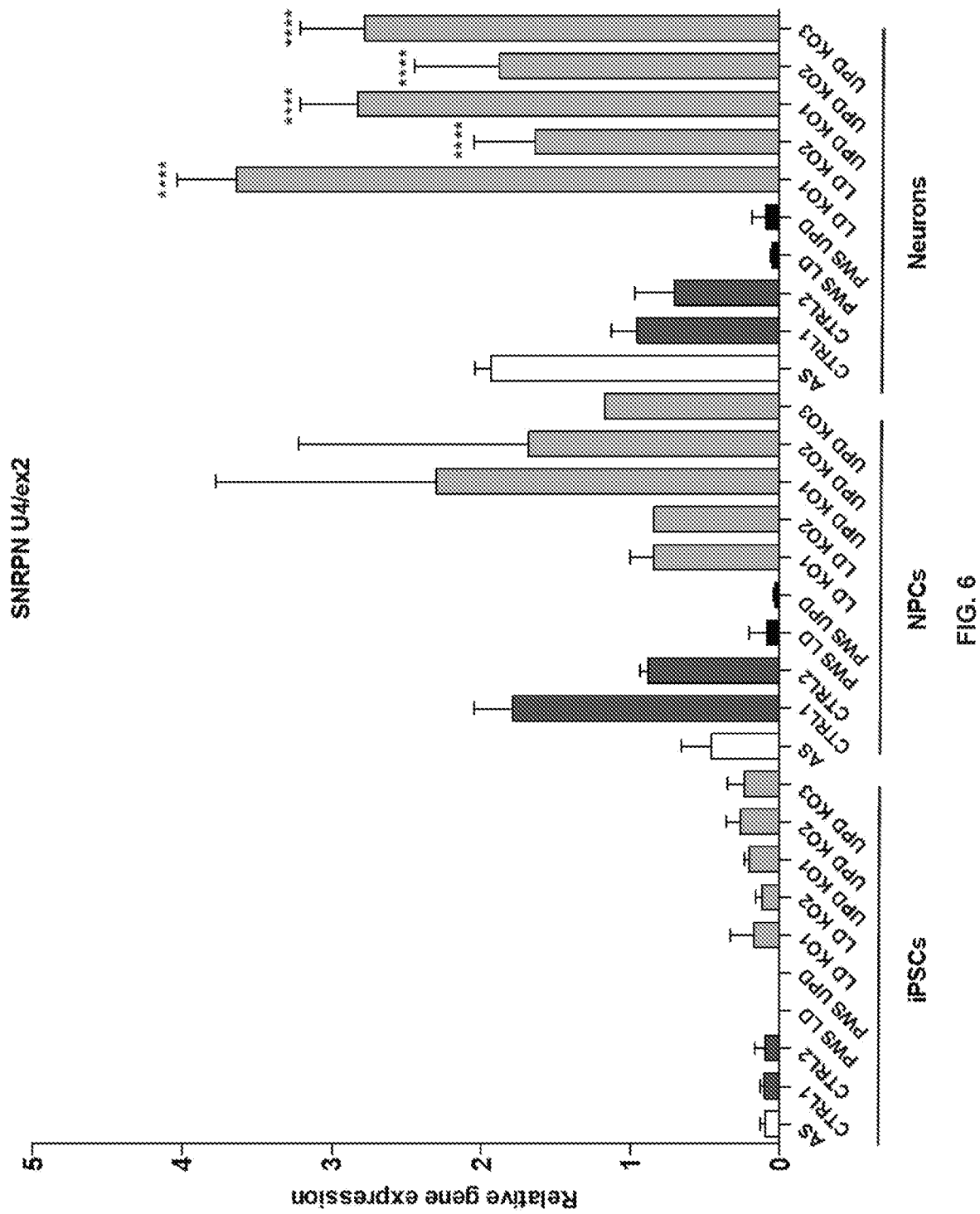
FIG. 6 shows ZNF274 KO activates SNRPN upstream promoters during neuronal differentiation of PWS iPSCs. Gene expression of the SNRPN U exons (U4/ex2) in iPSCs, NPCs, and neurons. The same color code as in FIG. 1B is used. Data were normalized to CTRL1 or CTRL2 neurons for each panel and plotted as the mean with Standard Deviation (SD). A minimum of 3, 1, and 2 biological replicates per cell line for iPSCs, NPCs, and neurons, respectively, were performed. Significance was calculated using one-way analysis of variance (ANOVA) test with a Dunnett post-test to compare the two LD KOs to PWS LD and the three UPD KOs to PWS UPD.

The SNRPN U4/exon 2 transcripts were completely rescued by ZNF274 KO in neurons while SNRPN transcripts utilizing exon 1 remained silent and exon 3/4 transcripts were partially activated (FIG. 4, FIGS. 5A-5C and TABLES 8-12). These results were consistent with the hypothesis that the ZNF274 complex regulates PWS transcripts via the SNRPN upstream promoters. The upstream exons are preferentially used in neurons and NPCs. In support of this, higher levels of SNRPN U4/exon 2 expression were attained in neurons and NPCs upon ZNF274 KO than in iPSCs (FIG. 5A and FIG. 5B) in accord with the reports that the U1B and U1A promoters are highly active in the brain (FIG. 6). While ZNF274 KO in PWS LD and UPD neurons activated robust expression of most maternal PWS transcripts (FIG. 4, FIGS. 5A-5C, FIG. 6 and TABLES 8-12), there was no change in 5mC levels at the PWS-IC (FIG. 2D and FIG. 5E), a finding consistent with the observation that ZNF274 KO did not activate SNRPN exon 1 transcription (FIG. 4, FIG. 5B and TABLES 8-12) and with the contention that ZNF274 binding to the maternal PWS locus mediated silencing by a mechanism independent of the PWS-IC. The hypothesis is consistent with reports that deletion of the PWS-IC does not result in the loss of imprinted expression in brain.

Further upstream in the imprinted PWS region, expression of MAGEL2 and MKRN3 was detected in PWS LD and UPD neurons and an up-regulation of both upon ZNF274 KO (FIG. 4 and TABLES 8-12). NDN was not detected in PWS LD and UPD neurons and was not activated by ZNF274 KO (FIG. 4 and TABLES 8-12). The latter result would suggest that, like SNRPN exon 1 but not other PWS transcripts, NDN imprinting was regulated by the PWS-TC, consistent with a mouse model in which deletion of the maternal PWS-TC activated Ndn expression. CYFIP1 and CHRNA7, genes outside the 15q11-q13 imprinted region, were expressed in neurons derived from all iPSC lines. The mRNA levels of both genes were the same in PWS LD and UPD, and were not affected in their ZNF274 KO derivatives (FIG. 4 and TABLES 8-12). These results suggested a role for ZNF274-mediated repression of most neuronal transcripts within but not outside of the imprinted chromosome 15q11-q13 region.

TABLE 8

Taqman assay list

| Genes short names | Card Names | Class | Imprinting | Allele |
|---|---|---|---|---|
| CYFIP1 | CYFIP1-Hs00383158_m1 | outside 15q11.2-q13 region (BP1-BP2) | | |
| NIPA1 | NIPA1-Hs00331974_m1 | outside 15q11.2-q13 region (BP1-BP2) | | |
| GOLGA6L2 | GOLGA6L2-Hs00704434_s1 | outside 15q11.2-q13 region (BP1-BP2) | | |
| MKRN3 | MKRN3-Hs00271653_s1 | 15q11.2-q13 region deleted in PWS LD | Genes submitted to parental imprinting | Paternal expression |
| MAGEL2 | MAGEL2-Hs00255922_s1 | 15q11.2-q13 region deleted in PWS LD | Genes submitted to parental imprinting | Paternal expression |
| NDN | NDN-Hs00267349_s1 | 15q11.2-q13 region deleted in PWS LD | Genes submitted to parental imprinting | Paternal expression |
| PWRN1 | PWRN1-Hs03676742_m1 | 15q11.2-q13 region deleted in PWS LD | Genes submitted to parental imprinting | Paternal expression |
| NPAP1 | NPAP1-Hs00255840_s1 | 15q11.2-q13 region deleted in PWS LD | Genes submitted to parental imprinting | Paternal expression |
| SNRPN U1B/U2 | SNRPN-Hs00909633_m1 | 15q11.2-q13 region deleted in PWS LD | Genes submitted to parental imprinting | Paternal expression |
| SNRPN U1A/U2 | SNRPN-Hs00266087_m1 | 15q11.2-q13 region deleted in PWS LD | Genes submitted to parental imprinting | Paternal expression |
| SNRPN U2/U4 | SNRPN-Hs00309634_m1 | 15q11.2-q13 region deleted in PWS LD | Genes submitted to parental imprinting | Paternal expression |
| SNRPN U4/ex 2 | SNRPN-Hs00909636_m1 | 15q11.2-q13 region deleted in PWS LD | Genes submitted to parental imprinting | Paternal expression |
| SNRPN ex 1/2 | SNURF; SNRPN-Hs00243205_m1 | 15q11.2-q13 region deleted in PWS LD | Genes submitted to parental imprinting | Paternal expression |
| SNRPN ex 3/4 | SNURF; SNRPN-Hs00256090_m1 | 15q11.2-q13 region deleted in PWS LD | Genes submitted to parental imprinting | Paternal expression |
| PWARS | PWARS-Hs03453340_s1 | 15q11.2-q13 region deleted in PWS LD | Genes submitted to parental imprinting | Paternal expression |
| PWARS/HBT8 | LOC100506965-hS00297979_s1 | 15q11.2-q13 region deleted in PWS LD | Genes submitted to parental imprinting | Paternal expression |
| 116HGG1 | SNRPN-Hs03454084_m1 | 15q11.2-q13 region deleted in PWS LD | Genes submitted to parental imprinting | Paternal expression |
| SNORD116GG1 (−1) | SNORD116-1-Hs03463102_g1 | 15q11.2-q13 region deleted in PWS LD | Genes submitted to parental imprinting | Paternal expression |
| 116HGG2 | SNRPN-Hs03454228_m1 | 15q11.2-q13 region deleted in PWS LD | Genes submitted to parental imprinting | Paternal expression |
| SNORD116GG2 (−11) | SNORD116-11-Hs04275268_gH | 15q11.2-q13 region deleted in PWS LD | Genes submitted to parental imprinting | Paternal expression |
| 116HGG3 | SNRPN-Hs01374551_m1 | 15q11.2-q13 region deleted in PWS LD | Genes submitted to parental imprinting | Paternal expression |
| SNORD116GG3 (−29) | SNORD116-23-Hs03300097_s1 | 15q11.2-q13 region deleted in PWS LD | Genes submitted to parental imprinting | Paternal expression |
| IPW | IPW-Hs03455409_s1 | 15q11.2-q13 region deleted in PWS LD | Genes submitted to parental imprinting | Paternal expression |
| IPW ex2/3 | SNRPN,IPW-Hs01374548_g1 | 15q11.2-q13 region deleted in PWS LD | Genes submitted to parental imprinting | Paternal expression |
| PWAR1 | PWAR1-Hs03309977_s1 | 15q11.2-q13 region deleted in PWS LD | Genes submitted to parental imprinting | Paternal expression |
| 115HG | SNRPN-Hs03454279_m1 | 15q11.2-q13 region deleted in PWS LD | Genes submitted to parental imprinting | Paternal expression |
| SNORD115-1 | SNORD115-1-Hs04231709_gH | 15q11.2-q13 region deleted in PWS LD | Genes submitted to parental imprinting | Paternal expression |
| 115-109HG | SNRPN-Hs01372958_m1 | 15q11.2-q13 region deleted in PWS LD | Genes submitted to parental imprinting | Paternal expression |
| UBE3A-ATS | SNRPN-Hs01372960_m1 | 15q11.2-q13 region deleted in PWS LD | Genes submitted to parental imprinting | Paternal expression |
| UBE3A ex 11/12 | UBE3A-Hs00963664_g1 | 15q11.2-q13 region deleted in PWS LD | Genes submitted to parental imprinting | Maternal expression in neurons |
| UBE3A ex 7/8 | UBE3A-Hs00166580_m1 | 15q11.2-q13 region deleted in PWS LD | Genes submitted to parental imprinting | Maternal expression in neurons |
| ATP10A | ATP10A-Hs00257114_m1 | 15q11.2-q13 region deleted in PWS LD | Genes submitted to parental imprinting | controversial |
| GABRB3 | GABRB3-Hs00241459_m1 | 15q11.2-q13 region deleted in PWS LD | | |
| GABRA5 | GABRA5-Hs00181291_m1 | 15q11.2-q13 region deleted in PWS LD | | |
| GABRG3 | GABRG3-Hs00264276_m1 | 15q11.2-q13 region deleted in PWS LD | | |
| CHRNA7 | CHRNA7-Hs01063373_m1 | outside 15q11.2-q13 region (BP4-BP5) | | |
| FOXG1 | FOXG1-Hs01850784_s1 | neuronal marker | | |
| RBFOX1 | RBFOX1-Hs01125659_m1 | neuronal marker | | |
| RBFOX3 | RBFOX3-Hs013700653_m1 | neuronal marker | | |
| NPY | NPY-Hs00173470_m1 | neuronal marker | | |
| SOX2 | SOX2-Hs01053049_s1 | neuronal marker | | |
| HTR2C | HTR2C-Hs00968672_m1 | neuronal marker | | |
| ZNF274 | ZNF274-Hs00249453_m1 | Target gene | | |

TABLE 8-continued

Taqman assay list

| Genes short names | Card Names | Class | Imprinting | Allele |
|---|---|---|---|---|
| ZNF180 | ZNF180-Hs00997627_m1 | Expected Downstream target | | |
| ZNF554 | ZNF554-Hs01014440_m1 | Expected Downstream target | | |
| GAPDH | GAPDH-Hs02758991_g1 | second internal calibrator assay | | |
| GAPDH-calibrator | GAPDH-Hs99999905_m1 | endogenous gene = used as calibrator | | |

TABLE 9

CT values list

CTR.L2 = reference

| | Biological replicate # | | | | | | | |
|---|---|---|---|---|---|---|---|---|
| | 1 | 1 | 1 | 1 | 1 | 1 | 2 | 3 |
| Genes | Technical replicate # | | | | | | | |
| short names | 1 | 2 | 3 | 4 | 5 | 6 | 1 | 1 |
| CYFIP1 | 26.480686 | 26.609007 | 26.28538 | 26.671919 | 26.893164 | 27.071867 | 26.002958 | 26.78815 |
| NIPA1 | 29.772608 | 30.461052 | 30.88137 | 31.299295 | 31.747791 | 30.766388 | 29.03148 | 31.278374 |
| GOLGA6L2 | ND | 34.76067 | 34.03716 | 34.00156 | 33.73146 | 34.23765 | ND | 33.13554 |
| MKRN3 | 25.992939 | 26.875992 | 26.346405 | 26.695805 | 26.69024 | 26.644539 | 25.595844 | 26.439054 |
| MAGEL2 | 27.702837 | 28.040808 | 28.353643 | 27.955694 | 28.393623 | 28.048744 | 27.584694 | 29.07255 |
| NDN | 25.133844 | 25.653016 | 25.20057 | 25.42243 | 24.970661 | 25.632611 | 24.333992 | 25.86526 |
| PWRN1 | 35.966595 | 36.3846 | 36.17162 | 37.388645 | Omitted | 38.57689 | Undetermined | Undetermined |
| NPAP1 | 31.441956 | 31.012466 | 31.696802 | 31.845058 | 31.949345 | 31.32736 | 30.58436 | 31.86742 |
| SNRPN U1B/U2 | ND | 33.328407 | 34.55538 | 33.93331 | 34.63552 | 35.890633 | ND | 36.134968 |
| SNRPN U1A/U2 | 26.231577 | 26.573927 | 26.962015 | 26.729408 | 24.92182 | 27.206545 | 25.997068 | 26.83809 |
| SNRPN U2/U4 | ND | 24.490181 | 24.191236 | 24.942046 | Omitted | 26.756815 | ND | 25.13091 |
| SNRPN U4/ex 2 | 27.785774 | 27.59442 | 27.990515 | 28.07801 | Omitted | 28.11807 | 27.034859 | 27.292852 |
| SNRPN ex 1/2 | 23.734818 | 23.58067 | 21.962234 | 24.88214 | Omitted | 23.887335 | 22.732279 | 23.440395 |
| SNRPN ex 3/4 | 23.718401 | 23.516106 | 23.874062 | 23.177275 | 24.376688 | 25.64473 | 23.961107 | 24.128504 |
| PWAR5 | ND | 24.04749 | 23.912054 | 24.046764 | 24.560589 | 24.948488 | ND | 24.45945 |
| PWAR6/HBT8 | 23.34317 | 23.170412 | 23.201069 | 22.951668 | 23.503712 | 23.813454 | 22.22644 | 23.4713 |
| 116HGG1 | 27.096735 | 27.372774 | 27.491112 | 27.321346 | 27.517607 | 27.79899 | 26.04551 | 27.146055 |
| SNORD116-HGG1 (−1) | 21.209124 | 20.557287 | 20.289179 | 20.134262 | 20.915354 | 20.719255 | 19.731356 | 21.404074 |
| 116HGG2 | 24.44691 | 24.219158 | 24.27932 | 24.116323 | 24.432854 | 24.48332 | 23.240923 | 24.439741 |
| SNORD116-HGG2 (−11) | 27.622147 | 25.111038 | 28.092163 | 25.572536 | 26.952675 | 26.597994 | 26.731564 | 27.42035 |
| 116HGG3 | 25.95773 | 26.569239 | 26.636862 | 26.207361 | 26.691038 | 27.10693 | 25.636295 | 26.264036 |
| SNORD116-HGG3 (−29) | 24.925589 | 23.713888 | 23.877728 | 23.838678 | 25.308273 | 25.23528 | 23.911364 | 24.874504 |
| IPW | 25.620756 | 25.576328 | 25.688171 | 25.999369 | 26.593628 | 25.994139 | 24.779993 | 25.418089 |
| IPW ex2/3 | 25.705717 | 25.649437 | 25.900547 | 25.299376 | 25.212244 | 26.211044 | 24.474379 | 25.734821 |
| PWAR1 | 26.843637 | 26.650043 | 26.827644 | 26.83137 | 27.78033 | 27.601366 | 26.161963 | 27.648773 |
| 115HG | 27.108881 | 26.709625 | 27.31334 | 27.265523 | 26.945013 | 27.413378 | 26.3064 | 27.797619 |
| SNORD115-1 | 19.01794 | 20.115414 | 19.406199 | 19.732845 | 19.740253 | 19.557661 | 18.519503 | 21.15373 |
| 115-109HG | ND | 24.863844 | 25.490976 | 25.369408 | 25.726519 | 26.24809 | ND | 26.174343 |
| UBE3A-ATS | 32.594887 | 31.98552 | 31.954311 | 32.505318 | 32.865337 | 33.692368 | 32.372643 | 32.43387 |
| UBE3A ex 11/12 | 25.730135 | 25.024763 | 25.67173 | 25.759333 | 26.008219 | 26.389225 | 25.161955 | 26.129337 |
| UBE3A ex 7/8 | 25.888016 | 26.377218 | 26.550234 | 26.224686 | 26.84011 | 26.699636 | 25.278322 | 26.689522 |
| ATP10A | 31.309206 | 31.59965 | 31.51412 | 31.103773 | 31.92915 | 31.63144 | 32.50826 | 34.52629 |
| GABRB3 | 26.086983 | 25.883589 | 25.907064 | 26.226212 | 26.398952 | 26.330416 | 25.173512 | 26.589338 |
| GABRA5 | 28.777285 | 28.535019 | 28.948584 | 28.820704 | 27.691633 | 28.869352 | 28.753052 | 29.77183 |
| GABRG3 | 30.153616 | 30.41996 | 30.62335 | 30.6275 | 29.63678 | 30.81438 | 29.72072 | 31.69794 |
| CHRNA7 | ND | 30.08985 | 30.39262 | 30.21716 | 30.05886 | 30.39859 | ND | 30.02143 |
| FOXG1 | 22.243864 | 22.35907 | 22.282621 | 22.109735 | 22.597328 | 22.855604 | 24.569414 | 24.359978 |
| RBFOX1 | 30.36486 | 30.981283 | 31.009476 | 30.433092 | 30.778242 | 31.101437 | 30.489977 | 33.035408 |
| RBFOX3 | 28.034452 | 28.449575 | 28.533897 | 28.090963 | 28.53066 | 28.77857 | 28.042582 | 29.772762 |
| NPY | 28.66647 | 28.230799 | 28.169308 | 28.416462 | 28.600035 | 28.460361 | 28.378944 | 30.348448 |
| SOX2 | ND | 21.016968 | 20.928877 | 20.615635 | 21.26141 | 22.35113 | ND | 21.360062 |
| HTR2C | 34.77221 | 34.81884 | 35.25441 | 35.18988 | 35.54013 | 35.09008 | 36.92302 | 37.0071 |
| ZNF274 | 27.04338 | 28.903107 | 26.980833 | 26.80467 | 27.016258 | 27.343533 | 26.196585 | 26.880066 |

TABLE 9-continued

CT values list

| | CTR.L2 = reference | | | | | | | |
|---|---|---|---|---|---|---|---|---|
| | Biological replicate # | | | | | | | |
| | 1 | 1 | 1 | 1 | 1 | 1 | 2 | 3 |
| Genes | Technical replicate # | | | | | | | |
| short names | 1 | 2 | 3 | 4 | 5 | 6 | 1 | 1 |
| ZNF180 | 27.972372 | 28.269459 | 28.323238 | 28.38838 | 28.346088 | 28.75915 | 26.676165 | 28.455437 |
| ZNF554 | 28.297579 | 28.154257 | 28.08486 | 28.168854 | 28.159172 | 28.845984 | 27.852283 | 28.854652 |
| GAPDH | ND | 21.577618 | 22.314138 | 21.715225 | 21.254545 | 22.452402 | ND | 21.867243 |
| GAPDH-calibrator | 20.180447 | 20.78053 | 20.78053 | 20.78053 | 29.78053 | 29.81019 | 19.80259 | 21.11595 |

Undetermined = Ct >40 or no expression
Omitted = reaction parameters abnormal
/ = Ct >30 for controls
// = Ct >32 for controls

TABLE 10

RQ values list

| | CTR.L2 = reference | | | CTRL1 | | | |
|---|---|---|---|---|---|---|---|
| | Biological replicate # | | | | | | |
| | 1 | 2 | 3 | 1 | 2 | 3 | 1 |
| | Technical replicate # | | | | | | |
| Genes short names | 1-6 | 1 | 1 | 1 | 1 | 1 | 1 |
| CYFIP1 | 1 | 1.072 | 1.119 | 2.052 | 0.963 | 1.082 | 0.845 |
| NIPA1 | 1 | 1.286 | 1.113 | 1.993 | 1.979 | 0.856 | 0.613 |
| GOLGA6L2 | | | | | | | |
| MKRN3 | 1 | 1.013 | 1.463 | 0.563 | 0.271 | 0.484 | 0.738 |
| MAGEL2 | 1 | 0.835 | 1.365 | 1.424 | 0.8 | 0.276 | 0.949 |
| NDN | 1 | 1.34 | 0.86 | 0.451 | 0.566 | 0.199 | 1.071 |
| PWRN1 | | | | | | | |
| NPAP1 | | | | | | | |
| SNRPN U1B/U2 | | | | | | | |
| SNRPN U1A/U2 | 1 | 0.905 | 0.866 | 0.939 | 1.087 | 0.863 | 0.011 |
| SNRPN U2/U4 | 1 | ND | 0.81 | 0.865 | 0.809 | 0.436 | 0.002 |
| SNRPN U4/ex 2 | 1 | 1.295 | 1.906 | 1.417 | 1.424 | 0.919 | ND |
| SNRPN ex 1/2 | 1 | 1.542 | 1.292 | 0.779 | 1.211 | 0.669 | 0.652 |
| SNRPN ex 3/4 | 1 | 0.65 | 0.961 | 0.756 | 0.806 | 0.363 | 0.707 |
| PWAR5 | 1 | ND | 1.012 | 0.732 | 1.403 | 0.919 | 1.187 |
| PWAR6/HBT8 | 1 | 1.669 | 1.05 | 0.646 | 0.973 | 0.591 | 1.184 |
| 116HGG1 | 1 | 1.595 | 1.532 | 1.5 | 1.643 | 1.156 | 1.857 |
| SNORD116HGG1 (−1) | 1 | 2.143 | 0.662 | 1.205 | 0.707 | 0.992 | 1.254 |
| 116HGG2 | 1 | 1.775 | 1.115 | 1.355 | 1.205 | 0.693 | 0.778 |
| SNORD116HGG2 (−11) | 1 | 1.427 | 0.45 | 2.543 | 0.81 | 0.492 | 0.562 |
| 116HGG3 | 1 | 0.962 | 1.513 | 1.062 | 0.954 | 0.665 | 0.854 |
| SNORD116HGG3 (−29) | 1 | 1.564 | 0.782 | 0.81 | 0.509 | 0.555 | 0.728 |
| IPW | 1 | 1.378 | 1.843 | 1.349 | 1.603 | 0.98 | 1.185 |
| IPW ex2/3 | 1 | 1.807 | 1.084 | 0.733 | 0.682 | 0.477 | 0.891 |
| PWAR1 | 1 | 1.234 | 0.817 | 0.949 | 1.046 | 0.767 | 1.074 |
| 115HG | 1 | 1.342 | 0.756 | 0.656 | 0.935 | 0.548 | 1.528 |
| SNORD115-1 | 1 | 1.087 | 0.476 | 0.806 | 0.886 | 0.253 | 1.672 |
| 115-109HG | 1 | ND | 0.719 | 0.58 | 0.938 | 0.394 | 1.201 |
| UBE3A-ATS | | | | | | | |
| UBE3A ex 11/12 | 1 | 1.141 | 0.884 | 0.641 | 0.671 | 0.449 | 1.044 |
| UBE3A ex 7/8 | 1 | 1.174 | 1.105 | 1.149 | 1.062 | 0.859 | 0.599 |
| ATP10A | 1 | 0.335 | 0.159 | 3.842 | 1.85 | 0.937 | 1.2 |
| GABRB3 | 1 | 1.45 | 0.901 | 0.654 | 1.755 | 0.293 | 1.421 |
| GABRA5 | 1 | 0.783 | 0.522 | 1.029 | 3.125 | 0.396 | 1.852 |
| GABRG3 | 1 | 1.039 | 0.488 | 2.142 | 5.729 | 0.33 | 0.738 |
| CHRNA7 | 1 | ND | 1.418 | 1.031 | 0.83 | 0.209 | 5.188 |
| FOXG1 | 1 | 0.154 | 0.31 | 1.824 | 1.279 | 2.273 | 0.136 |
| RBFOX1 | 1 | 0.706 | 0.268 | 14.207 | 30.092 | 14.877 | 25.441 |
| RBFOX3 | 1 | 0.765 | 0.488 | 1.255 | 3.397 | 0.476 | 1.249 |
| NPY | 1 | 0.939 | 0.317 | 4.038 | 3.557 | 4.092 | 0.737 |
| SOX2 | 1 | ND | 0.953 | 0.778 | 0.439 | 0.755 | 0.564 |
| HTR2C | | | | | | | |

TABLE 10-continued

RQ values list

| | CTR.L2 = reference | | | CTRL1 | | | |
|---|---|---|---|---|---|---|---|
| | Biological replicate # | | | | | | |
| | 1 | 2 | 3 | 1 | 2 | 3 | 1 |
| | Technical replicate # | | | | | | |
| Genes short names | 1-6 | 1 | 1 | 1 | 1 | 1 | 1 |
| ZNF274 | 1 | 1.384 | 1.303 | 1.228 | 0.829 | 0.522 | 1.224 |
| ZNF180 | 1 | 1.89 | 1.158 | 1.05 | 1.071 | 0.815 | 1.458 |
| ZNF554 | 1 | 1.048 | 0.77 | 1.663 | 1.046 | 1.119 | 1.057 |
| GAPDH | 1 | ND | 1.136 | 1.572 | 0.916 | 0.92 | 1.472 |

/ = Ct >30 for controls

// = Ct >32 for controls

TABLE 11

RQ values list

| Genes short names | CTRL2 = reference | CTRL1 | AS | PWS LD | PWS LD-SC1 | PWS UPD |
|---|---|---|---|---|---|---|
| Biological replicate # | 3 | 3 | 3 | 3 | 1 | 3 |
| Technical replicate # | 5, 1, 1 | 1 each | 1 each | 1 each | 1 each | 1 each |
| CYFIP1 | 1.0636667 | 1.3656667 | 0.89299995 | 2.205334 | 0.724 | 1.220667 |
| NIPA1 | 1.133 | 1.6093334 | 0.6843333 | 2.460667 | 0.865 | 3.845 |
| GOLGA6L2 | 1.7595 | 0.3643333 | 0.70133334 | 0 | 0.565 | 0.387 |
| MKRN3 | 1.1586667 | 0.43933335 | 0.59966666 | 0.5743334 | 0.487 | 0.602 |
| MAGEL2 | 1.0666667 | 0.8333333 | 1.1696666 | 0.5343333 | 0.187 | 0.07 |
| NDN | 1.0666667 | 0.4053333 | 0.77933335 | 0 | 0 | 0 |
| PWRN1 | 0.33333334 | 0 | 0 | 0 | 0 | 0 |
| NPAP1 | 1.1536666 | 0.7833333 | 0.32966664 | 0.7486667 | 0 | 0.05733334 |
| SNRPN U1B/U2 | 0.6555 | 0.29333332 | 0 | 0 | 0.088 | 0 |
| SNRPN U1A/U2 | 0.92366666 | 0.963 | 0.010333333 | 0.113 | 0.406 | 0.05 |
| SNRPN U2/U4 | 0.905 | 0.7033334 | 0.002333334 | 0.012 | 0.488 | 0.03333334 |
| SNRPN U4/ex 2 | 1.4003334 | 1.2533334 | 1.9154999 | 0.228 | 0.914 | 0.1403333 |
| SNRPN ex 1/2 | 1.278 | 0.8863333 | 1.4143333 | 0 | 0 | 0 |
| SNRPN ex 3/4 | 0.8703334 | 0.64166665 | 1.5243334 | 0.009666666 | 0.203 | 0.006666666 |
| PWAR5 | 1.006 | 1.018 | 1.1193334 | 0.007 | 0.112 | 0.02733333 |
| PWAR6/HBT8 | 1.2396666 | 0.7366667 | 1.1283333 | 0.04133333 | 0.094 | 0.02033333 |
| 116HGG1 | 1.3756666 | 1.433 | 1.3093333 | 0.07333333 | 0.086 | 0.05466667 |
| SNORD116G1 (−1) | 1.2683333 | 0.968 | 1.4793333 | 0.02733333 | 0.045 | 0.012 |
| 116HGG2 | 1.2966666 | 1.0843333 | 0.77633333 | 0.04066667 | 0.066 | 0.03066667 |
| SNORD116G2 (−11) | 0.95900005 | 1.2816666 | 1.0873333 | 0.043 | 0.021 | 0.026 |
| 116HGG3 | 1.1583333 | 0.8936667 | 0.63233334 | 0.03266667 | 0.1 | 0.03233333 |
| SNORD116G3 (−29) | 1.112 | 0.6246667 | 1.587 | 0.018 | 0.05 | 0.02666667 |
| IPW | 1.4070001 | 1.3106667 | 0.75333333 | 0.05233334 | 0.194 | 0.06366666 |
| IPW ex2/3 | 1.297 | 0.6306667 | 0.60033333 | 0.03233333 | 0.093 | 0.01833333 |
| PWAR1 | 1.017 | 0.9206667 | 0.675 | 0.05333333 | 0.141 | 0.03466667 |
| 115HG | 1.0326667 | 0.713 | 0.87833333 | 0.04133333 | 0.11 | 0.03466667 |
| SNORD115-1 | 0.85433334 | 0.64166665 | 2.372 | 0.02233333 | 0.056 | 0.018 |
| 115-109HG | 0.8595 | 0.63733333 | 0.91166663 | 0.001 | 0.125 | 0.01933334 |
| UBE3A-ATS | 1.0233334 | 1.186 | 1.4743334 | 0.02366667 | 0.338 | 0.04666667 |
| UBE3A ex 11/12 | 1.0083333 | 0.58699995 | 0.443 | 1.433667 | 1.647 | 2.651667 |
| UBE3A ex 7/8 | 1.093 | 1.0233334 | 0.37133333 | 1.939333 | 1.178 | 2.764667 |
| ATP10A | 0.498 | 2.2096667 | 0.557 | 0.671 | 0.249 | 0.4443333 |
| GABRB3 | 1.117 | 0.90066665 | 1.1123333 | 2.214333 | 1.056 | 2.892 |
| GABRA5 | 0.7683334 | 1.5166668 | 1.415 | 5.376 | 2.388 | 3.584667 |
| GABRG3 | 0.8423333 | 2.7336667 | 0.73933333 | 2.698333 | 0.916 | 5.373667 |
| CHRNA7 | 0.488 | 0.69 | 4.112 | 2.623 | 0.906 | 2.535 |
| FOXG1 | 0.658 | 1.7919999 | 0.04533334 | 8.449666 | 8.644 | 1.013333 |
| RBFOX1 | 0.751 | 19.725332 | 19.335 | 10.04433 | 0.935 | 0.493 |
| RBFOX3 | 0.75200003 | 1.7093334 | 1.856667 | 2.646 | 2.201 | 1.929667 |
| NPY | 0.97650003 | 3.8956668 | 0.2646667 | 3.206 | 0.211 | 0.3226667 |
| SOX2 | 0.46800002 | 0.6573333 | 0.532 | 1.322 | 1.335 | 1.069333 |
| HTR2C | 1.229 | 3.5909998 | 6.726334 | 5.684333 | 3.625 | 1.450334 |
| ZNF274 | 1.3493333 | 0.85966665 | 1.224667 | 2.265 | 1.809 | 1.497667 |
| ZNF180 | 0.93933326 | 0.9786667 | 1.195667 | 2.948334 | 1.98 | 2.124667 |
| ZNF554 | 1.0680001 | 1.276 | 0.77 | 2.643333 | 1.536 | 1.582667 |
| GAPDH | 1.068 | 1.136 | 0.993 | 0.943 | 1.567 | 0.8006666 |

TABLE 11-continued

| | RQ values list | | | | | |
|---|---|---|---|---|---|---|
| Genes short names | LD KO1 | LD KO2 | UPD KO1 | UPD KO2 | UPD KO3 | low expression? |
| Biological replicate # | 3 | 3 | 3 | 1 | 1 | |
| Technical replicate # | 1 each | 1 each | 1 each | 1 | 1-2 | |
| CYFIP1 | 2.458667 | 1.654667 | 1.787 | 1.4043335 | 1.434 | |
| NIPA1 | 6.633333 | 3.243667 | 3.658334 | 2.7533333 | 0.646 | |
| GOLGA6L2 | 2.496 | 1.58 | 6.039333 | 0 | | !! |
| MKRN3 | 2.173 | 0.8866667 | 4.530333 | 0.086 | 0.005 | |
| MAGEL2 | 4.285667 | 1.324667 | 1.32 | 0.15233333 | 0.301 | |
| NDN | 0.006666666 | 0.000333333 | 0.000333333 | 0 | 0.001 | |
| PWRN1 | 2.697333 | 1.131 | 0.766 | 0 | 0 | !! |
| NPAP1 | 6.574 | 0.6583334 | 0.6636667 | 0.081 | 0 | !! |
| SNRPN U1B/U2 | 1.803 | 0.303 | 0.9073333 | 0 | 0.52 | !! |
| SNRPN U1A/U2 | 3.875 | 2.204667 | 1.250667 | 1.226 | 1.861 | |
| SNRPN U2/U4 | 2.954 | 0.842 | 0.728 | 0.569 | 1.248 | |
| SNRPN U4/ex 2 | 10.58667 | 2.733 | 3.488667 | 1.1833333 | 2.412 | |
| SNRPN ex 1/2 | 0 | 0 | 0 | 0 | 0 | |
| SNRPN ex 3/4 | 0.4673334 | 0.2603333 | 0.1613333 | 0.20833333 | 0.254 | |
| PWAR5 | 2.593 | 0.401 | 0.7606667 | 0.25633332 | 0.722 | |
| PWAR6/HBT8 | 1.959333 | 0.4946667 | 0.6363334 | 0.19633333 | 0.453 | |
| 116HGG1 | 3.166 | 0.8313333 | 1.029333 | 0.64066666 | 0.745 | |
| SNORD116G1 (−1) | 1.634667 | 0.6486667 | 0.5173333 | 0.45466664 | 0.642 | |
| 116HGG2 | 2.37 | 0.6536667 | 0.992 | 0.38300002 | 0.736 | |
| SNORD116G2 (−11) | 1.211 | 0.8953333 | 0.5576667 | 0.44266668 | 0.457 | |
| 116HGG3 | 1.863667 | 0.3886667 | 1.034333 | 0.32066667 | 0.991 | |
| SNORD116G3 (−29) | 1.09 | 0.493 | 0.987 | 0.5876667 | 0.824 | |
| IPW | 3.003 | 0.6206667 | 1.657 | 0.51766664 | 1.085 | |
| IPW ex2/3 | 2.311667 | 0.4573333 | 0.6203334 | 0.204 | 0.525 | |
| PWAR1 | 3.948667 | 0.4526667 | 0.9966667 | 0.17366666 | 0.579 | |
| 115HG | 2.588667 | 0.6126667 | 1.151333 | 0.19733334 | 0.204 | |
| SNORD115-1 | 1.813333 | 0.8926666 | 1.395333 | 0.5186667 | 0.538 | |
| 115-109HG | 3.128 | 0.243 | 0.6526667 | 0.17799999 | 0.214 | |
| UBE3A-ATS | 2.497 | 1.784667 | 1.793333 | 0.3956667 | 0.402 | ! |
| UBE3A ex 11/12 | 1.031333 | 0.526 | 1.750667 | 0.7243333 | 0.784 | |
| UBE3A ex 7/8 | 1.316667 | 0.641 | 2.355333 | 0.98200005 | 1.231 | |
| ATP10A | 0.659 | 0.3913333 | 5.224001 | 0.8386667 | 2.27 | ! |
| GABRB3 | 2.881 | 0.9606667 | 2.201667 | 0.779 | 0.755 | |
| GABRA5 | 6.300334 | 1.712333 | 4.641 | 1.3026667 | 1.186 | |
| GABRG3 | 6.644667 | 1.669333 | 5.176 | 0.45033336 | 0.464 | ! |
| CHRNA7 | 2.94 | 1.783 | 2.616 | 1.8923334 | 2.143 | ! |
| FOXG1 | 11.67867 | 2.025333 | 4.179333 | 0.002666667 | 0.019 | |
| RBFOX1 | 9.399333 | 1.718667 | 14.40033 | 7.0433335 | 4.76 | |
| RBFOX3 | 4.609 | 1.233 | 1.163333 | 0.42033336 | 0.683 | |
| NPY | 0.1216667 | 0.114 | 0.3086667 | 0.10966667 | 0.106 | |
| SOX2 | 3.189 | 1.268 | 1.220333 | 0.53333336 | 0.298 | |
| HTR2C | 22.83167 | 1.036333 | 2.226 | | 11.395 | !! |
| ZNF274 | 1.928333 | 0.8183333 | 0.7163334 | 0.8373334 | 0.683 | |
| ZNF180 | 4.574667 | 1.939 | 2.645333 | 1.2316667 | 1.187 | |
| ZNF554 | 3.29 | 1.531333 | 1.417 | 1.281 | 0.971 | |
| GAPDH | 0.768 | 1.142 | 0.6336667 | 0.71166664 | 0.685 | |

! = Ct > 30 for controls
!! = Ct > 32 for controls

TABLE 12

| | Statistics | | | | | |
|---|---|---|---|---|---|---|
| Genes short names | LD KO1 | LD KO2 | UPD KO1 | UPD KO2 | UPD KO3 | low expression? |
| CYFIP1 | ns | ns | ns | ns | na | |
| NIPA1 | **** | ns | ns | ns | ns | |
| GOLGA6L2 | na | na | na | na | na | !! |
| MKRN3 | * | ns | **** | ns | na | |
| MAGEL2 | **** | ns | ns | ns | na | |
| NDN | ns | ns | ns | ns | na | |
| PWRN1 | na | na | na | na | na | !! |
| NPAP1 | na | na | na | na | na | !! |
| SNRPN U1B/U2 | na | na | na | na | na | !! |
| SNRPN U1A/U2 | **** | ** | ns | ns | na | |
| SNRPN UA/U4 | * | ns | ns | ns | na | |

TABLE 12-continued

| Genes short names | LD KO1 | LD KO2 | UPD KO1 | UPD KO2 | UPD KO3 | low expression? |
|---|---|---|---|---|---|---|
| SNRPN U4/ex 2 | **** | **** | **** | ns | na | |
| SNRPN ex 1/2 | ns | ns | ns | ns | na | |
| SNRPN ex 3/4 | ns | ns | ns | ns | na | |
| PWAR5 | * | ns | ns | ns | na | |
| PWAR6/HBT8 | ** | ns | ns | ns | na | |
| 116HGG1 | **** | ns | ns | ns | na | |
| SNORD116HGG1 (−1) | * | ns | ns | ns | na | |
| 116HGG2 | *** | ns | ns | ns | na | |
| SNORD116HGG2 (−11) | ns | ns | ns | ns | na | |
| 116HGG3 | ** | ns | ns | ns | na | |
| SNORD116HGG3 (−29) | ns | ns | ns | ns | na | |
| IPW | **** | ns | * | ns | na | |
| IPW ex2/3 | *** | ns | ns | ns | na | |
| PWAR1 | **** | ns | ns | ns | na | |
| 115HG | **** | ns | ns | ns | na | |
| SNORD115-1 | ** | ns | ns | ns | na | |
| 115-109HG | ** | ns | ns | ns | na | |
| UBE3A-ATS | **** | ** | * | ns | na | ! |
| UBE3A ex 11/12 | ns | ns | ns | ** | na | |
| UBE3A ex 7/8 | ns | ns | ns | * | na | |
| ATP10A | ns | ns | **** | ns | na | ! |
| GABRB3 | ns | ns | ns | ** | na | |
| GABRA5 | ns | **** | ns | *** | na | |
| GABRG3 | **** | ns | ns | **** | na | ! |
| CHRNA7 | ns | ns | ns | ns | na | ! |
| FOXG1 | ns | * | ns | ns | na | |
| RBFOX1 | ns | ** | **** | * | na | |
| RBFOX3 | ns | ns | ns | ns | na | |
| NPY | ns | ns | ns | ns | na | |
| SOX2 | ns | ns | ns | ns | na | |
| HTR2C | na | na | na | na | na | !! |
| ZNF274 | ns | ns | ns | ns | na | |
| ZNF180 | ns | ns | ns | ns | na | |
| ZNF554 | ns | ns | ns | ns | na | |
| GAPDH | ns | ns | ns | ns | na | |

* $P < 0.05$,
** $P < 0.01$,
*** $P < 0.001$,
**** $P < 0.0001$

Example 6

Discussion

Maternally inherited silent PWS transcripts were activated by CRISPR-mediated knockout of ZNF274. Loss of ZNF274 resulted in a reduction of H3K9mc3 within the PWS locus (FIG. 1B, FIG. 1C, and FIG. 9) and activated expression of maternal transcripts in PWS iPSCs, NPCs, and neurons (FIGS. 1-6 and TABLES 8-12). Expression of maternal transcripts induced by ZNF274 KO in PWS neurons attained normal levels, and robust activation was observed not only within the PWS locus but also throughout the chromosome 15q11-q13 imprinted region (FIGS. 3-6 and TABLES 8-12). Two PWS maternal mRNAs that were not rescued by ZNF274 KO were the SNRPN transcript driven by the exon 1 promoter and NDN (FIG. 2B, FIG. 4, FIG. 5B and TABLES 8-12). For SNRPN, the ZNF274 KO may not have altered CpG methylation of the maternal PWS-IC (FIG. 2D and FIG. 5E) and, hence, did not activate the major SNRPN exon 1 promoter. NDN expression was not rescued by ZNF274 KO. The expression of both MAGEL2 and MKRN3 were up regulated in PWS LD and UPD neurons by ZNF274 KO (FIG. 4 and TABLES 8-12) suggesting that ZNF274 binding to the SNORD116 cluster contributed to silencing of maternal alleles (FIG. 7).

A decrease in the levels of UBE3A was not detected despite robust activation of UBE3A-ATS (FIG. 4 and TABLES 8-12). UBE3AATS mediated silencing of UBE3A may not have been detectable due to the relative immaturity of the neurons differentiated from the iPSCs or because the level of expression of the maternal UBE3A mRNA was intrinsically higher than that of the paternal allele and thus was more resistant to antisense-mediated silencing. In this regard, UBE3A expression in both PWS LD and UPD iPSC-derived neurons was increased relative to CTRLs (FIG. 4 and TABLES 8-12).

The activation of maternal transcripts in human PWS fibroblasts and a mouse model of PWS was demonstrated by using novel compounds that target histone methyltransferase G9a. The activation of maternal PWS RNAs via G9a inhibition was associated with reduced levels of H3K9me3 and H3K9me2 at the SNORD116 locus as well as reduced levels of H3K9mc2 at the PWS-IC, without affecting DNA methylation levels at the PWS-IC. At least in humans, the ZNF274/SETDB1 complex was also required for H3K9me3-mediated silencing of maternal chromosome 15q11-q13 transcripts. While it remains to be determined if the G9a- and ZNF274/SETDB 1-histone methylation are mutually independent or complimentary, there appear to be mechanistic differences. For example, NDN and SNRPN exon 1 were activated by G9a inhibition but not by ZNF274 KO (FIG. 2B, FIG. 4, FIG. 5B, and TABLES 8-12). This difference could be that the ZNF274/SETDB1 complex specifically regulated brain-specific PWS lncRNA promoters whereas for using the novel compounds, H3K9me2 reduction at the PWS-IC was responsible for NDN and SNRPN exon 1 expression, independently of the cell type.

Figure 7:
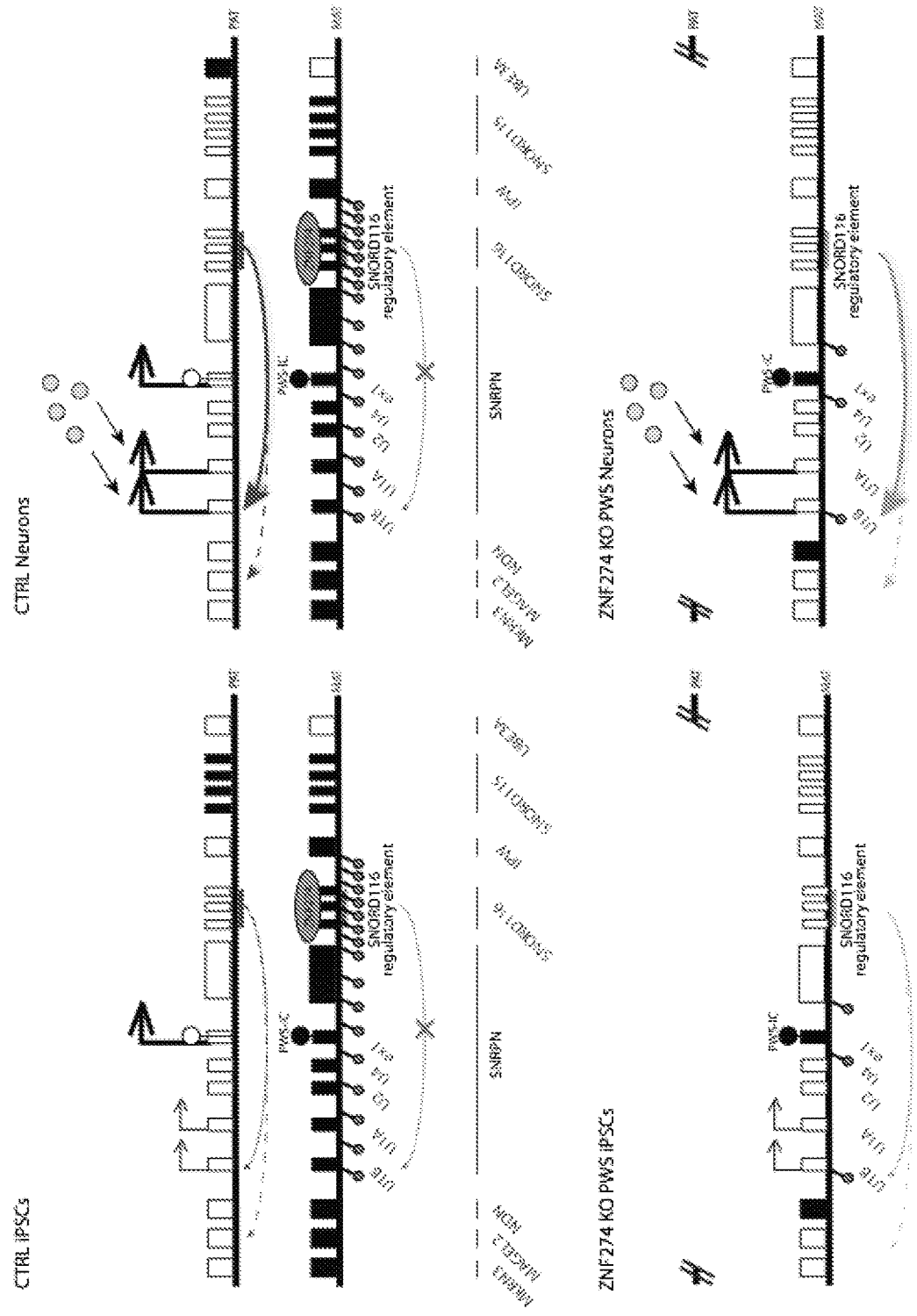
FIG. 7 shows a model of ZNF274-mediated silencing at the PWS locus. Open and closed boxes denote expressed and silenced 15q11.2-q13 genes, respectively, for the CTRL and PWS ZNF274 KO lines in iPSCs and neurons. The closed (methylated-5mC)/open (un-methylated-C) circles denote the PWS-IC. Arrows indicate the transcription start sites of SNRPN (we did not add arrows to other genes for clarity in the figure); thickness is relative to the degree of expression. Gene names are denoted sequentially between the CTRL and PWS ZNF274 KO lines. Red lollipops represent H3K9me3 signal. ZNF274 is denoted by the magenta ellipse. Colored segment over SNORD116 represents a putative regulatory element acting in cis on the SNRPN upstream exons. Yellow circles represent potential brain specific transcription factors activating the SNRPN upstream exons.

The ZNF274 complex may repress a cis-acting regulatory element that is required for initiating transcription from the SNRPN U1B and U1A promoters (FIG. 7). The regulatory element repressed by the ZNF274-complex could be an enhancer that activates the SNRPN U1B/U1A promoters. Alternatively, the element could be 116HG lncRNA cloud that functions to regulate the transcription of other genes. In our model (FIG. 7), a low level of expression of transcripts driven by the SNRPN upstream promoters in ZNF274 KO iPSCs was upregulated upon neuronal differentiation by brain-specific transcription factors. The activation of normally silent maternal PWS neuronal transcripts in the stem cell knockout model indicates that ZNF274 may be a potential target for future therapeutic application in PWS. The data (FIG. 1B, FIG. 9A, and FIG. 9B) was consistent with the observation that ZNF274 acts in concert with other ZNF proteins to deposit H3K9me3 at genomic target sites. ZNF274 KO may result in complete loss of H3K9me3 at only about 10% of its target sites.

Example 7

Also disclosed herein is a technology for generating PWS-specific iPSC (induced pluripotent stem cells) and their neuronal differentiation to study aspects of epigenetic regulation and the PWS disease mechanism. A ZNF274/SETDB1-containing epigenetic complex that binds maternal PWSCR was discovered to effect epigenetic silencing via the accumulation of H3K9me3 at the PWSCR. CRISPR lentiviral vectors were used to target ZNF274 and generated ZNF274 knock out clonal derivatives of the PWS iPSC lines, PWS1-7 large deletion (B17-21 and ZKL6), and UPD 1-2 (ZKU4B and ZKU21A). The two parental PWS iPSC lines and each of their 2 ZNF274 KO clonal derivatives as well as 2 normal controls (LcNL-1 and MCH2-10) have been differentiated into neurons. The RT-qPCR analyses (FIG. 10) indicates that upon ZNF274 knock out, a complete re-activation of neuronal transcripts was achieved for the 3 RNA transcripts form the PWS region, SNORD116, IPW, and SNORD115. These findings indicate that CRISPR-mediated KO of ZNF274 efficiently re-activated silent maternal PWSCR transcripts (SNORD116 and IPW) in neurons derived from PWS iPSCs.

Using induced pluripotent stem cell (iPSC) models of PWS, an epigenetic complex was discovered that is comprised of the zinc-finger protein ZNF274 and the SET domain bifurcated 1 (SETDB1) histone H3 lysine 9 (H3K9) methyltransferase and that silences the maternal alleles at the PWS locus. ZNF274 was knocked out and rescued the expression of silent maternal alleles in neurons derived from PWS iPSC lines, without affecting DNA methylation at the PWS-Imprinting Center (PWS-IC). The ZNF274 complex can be a separate imprinting mark that represses maternal PWS gene expression in neurons and can be a target for therapeutic applications to rescue the PWS phenotype.

Example 8

Deletion of ZNF274 Binding Sites Restores Maternal SNRPN and SNORD116 Expression in Neurons Derived from PWS iPSCs In order to develop an approach to activating PWSCR RNA transcripts by blocking the binding of ZNF274, a computational approach was developed to search for a consensus DNA binding site for ZNF274. 21 ZNF274 ChIP-Seq datasets were analyzed from 8 different cultured cell lines performed by the ENCODE Consortium, and 1572 reproducibly bound sites in the human genome were identified. The sequence was extracted of each of these sites from the reference human genome, and this set was analyzed with the Multiple Em for Motif Elicitation (MEME) suite. A single binding motif for ZNF274 that was strongly enriched in these putative binding regions was identified. Using this consensus binding site, all ZNF274 binding sites genome-wide were predicted using the Find Individual Motif Occurences (FIMO) routine from the MEME suite. The ZNF274 motif (TGAGTGAGAACTCATACC) was identified within 5 of the SNORD116s. There was a cluster of 30 SNORD116s in the PWSCR that have been classified into 3 groups based on DNA sequence similarity. Group 1 consists of SNORD116s 1 through 9 (FIG. 11), and the ZNF274 motif was identified in SNORD116-3, -5, -7, -8, and -9. ZNF274 binds to these 5 SNORD116 regions as shown by ChIP-Seq (Crunivel et al., *Hum Mol Genet.* 23: 4674-85, 2014). SNORD116-2, -4, and -6 each displayed a G to A substitution at position 8 in this motif (FIG. 11) and were not identified as being bound by ZNF274 in ChIP-Seq data. SNORD116-1 contained a different single nucleotide change from the ZNF274 consensus binding site (FIG. 11) and its potential to be bound by ZNF274 was currently undetermined. There was a 48 nt of sequence identity between the Group1 SNORD116s except for those substitutions within the ZNF274 motif (FIG. 11) thus allowing the design of blocking molecules that specifically target SNORD116 and not other genomic ZNF274 binding sites.

The ZNF274 binding site over SNORD116 was determined to specifically block or deplete ZNF274 binding at the PWS locus to reactivate maternal transcripts. In terms of relevance to animal models, the ZNF274 motif is conserved at the SNORD116 Group 1s of all nonhuman primate species that we have analyzed, including all nine Group1 SNORD116s in rhesus. In other disclosed aspects the ZNF274 binding motif to the PWSCR SNORD116s was validated in cells using guide RNAs to target CRISPR/Cas9 to cleave the binding site and reduce ZNF274 binding.

The ZNF274 binding sites comprising the ZNF274 binding consensus motif TGAGTGAGAACTCATACC (SEQ ID NO: 1) on chromosome 15 was deleted from various cell lines using CRISPR using gRNAs targeted to different parts of CTTGGAAAAGCTGAACAAAATGAGTGAGAACTCATACCGTCGTTCTCATCAGAACTGAG (SEQ ID NO: 42), which includes the ZNF274 binding consensus and 20 nucleotides on either side of it, which confers specificity to the ZNF274 binding sites within SNORD116. The cell lines used included LcNL1, MCH2-10, PWS1-7, B17-21, and ZDL17, which are described above. LcNL1 and MCH2-10 are iPSCs from two different neurotypical individuals. PWS 1-7 is an iPSC line derived from an individual with PWS caused by a large deletion of 15q11-q13. B17-21 is a derivative of PWS1-7 in which ZNF274 was knocked out by sequential use of two different CRISPRs (CCTCCAGGCTTCCGACGGCC (SEQ ID NO: 13) and CCTGCAGGACAACCTGCCGA (SEQ ID NO: 14)) to mutate (frameshift) ZNF274. ZDL17 is a derivative of PWS1-7 in which the two CRISPRs (SEQ ID NO: 13 and SEQ ID NO: 14) were used simultaneously to delete ZNF274. Another pair of gRNAs (CTGCGGTTCCACCATCACGC (SEQ ID NO: 47) and AGCAGCCTTAGGTCCGGTGA (SEQ ID NO: 48)) were also used simultaneously to delete ZNF274.

30-5 bis1 was a derivative of PWS1-7 in which the VQR variant of SpCas9 (NGAN (SEQ ID NO: 49) or NGNG (SEQ ID NO: 50) PAM sequence) was used with a gRNA (GAAAAGCTGAACAAAATGAG, SEQ ID NO: 43) in a lentiviral vector to delete 5 of 6 ZNF274 binding sites. Binding site 6 was partially mutated, as well, in this cell line. A gRNA (CTCAGTTCCGATGAGAACGA, SEQ ID NO: 44) was also used with canonical spCas9. SNOG1del #10 and SNOG1del #84 were derivatives of PWS1-7 in which the full cluster of 6 ZNF274 binding sites were deleted (as well as intervening sequence) using two CRISPRs (canonical SpCas9, NGG PAM sequence) and the gRNAs in GCCACTCTCATTCAGCACGT (SEQ ID NO: 45) and GCAGATTTCATATGTACCAC (SEQ ID NO: 46) simultaneously.

All cells were differentiated into 10-week forebrain glutamatergic neurons. RNA was isolated from the neurons and subjected to quantitative RT-PCR using commercially-available TaqMan probe-primer sets to detect SNORD116HGG2 (group 2 of SNORD116, SNOG2), SNRPN exons 1 and 2 (canonical 1st and 2nd exons of SNRPN), SNRPN exons 3 and 4 (gene body of SNRPN), and SNRPN exons U4 to exon 2 (transcripts originating from upstream exons of SNRPN). The probe primer sets used were as described above.

Figure 12:
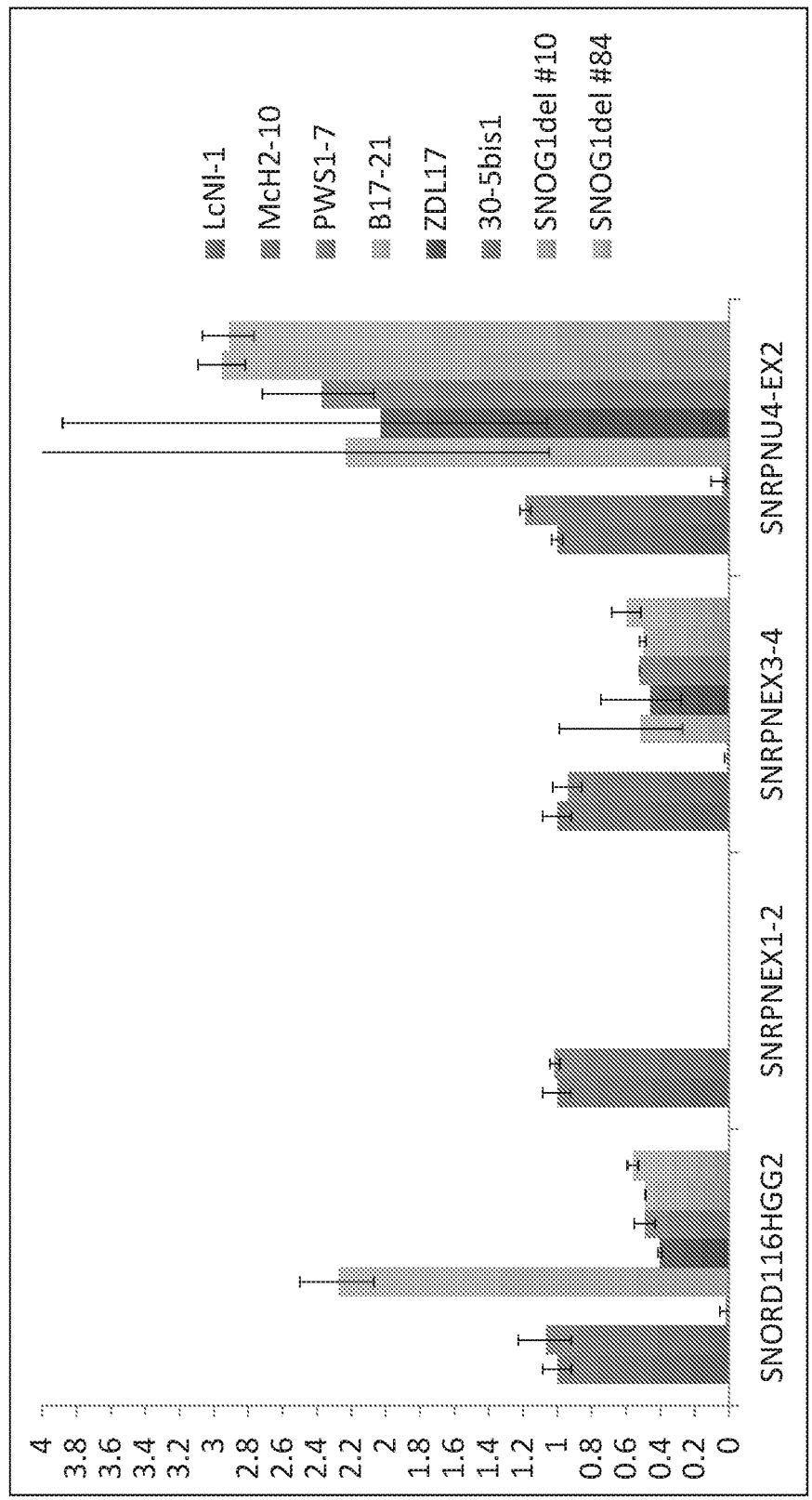
FIG. 12 shows activation of maternal SNRPN and the remaining copies of SNORD116 in neurons from engineered stem cell lines with altered ZNF274 binding sites at the SNORD116 locus (30-5bis1, SNOG1del #10 and SNOG1del #84).

As shown in FIG. 12, deletion of the ZNF274 binding sites restored maternal SNRPN and SNORD116 expression in neurons derived from PWS iPSCs. The results from B17-21 and ZDL17 using the ZNF274 KO is described above. When five of six ZNF274 binding sites were deleted from maternal SNORD116 in PWS iPSCs or when the full cluster of six ZNF274 binding sites were deleted from maternal SNORD116 in PWS iPSCs (including the intervening sequences), full expression activation of maternal SNRPN and the remaining pieces of SNORD116 resulted. This activation occurred due to the activation of upstream exons of SNRPN rather than activation of the canonical SNRPN promoter, which is also known as the PWS imprinting center. The same expression results that were achieved using the ZNF274 KO described above were achieved by mutating the ZNF274 binding sites in maternal SNORD116.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A guide RNA (gRNA) molecule comprising a polynucleotides sequence corresponding to SEQ ID NO: 13, SEQ ID NO: 14, SEQ ID NO: 43, SEQ ID NO: 44, SEQ ID NO: 45, SEQ ID NO: 46, SEQ ID NO: 47, SEQ ID NO: 48 or SEQ ID NO: 48.

Clause 2. A DNA targeting system that binds to a ZNF274 binding site, the DNA targeting system comprising at least one gRNA that binds and targets a polynucleotide sequence comprising a nucleotide sequence corresponding to at least one of SEQ ID NO: 1, SEQ ID NO: 42, SEQ ID NO: 43, SEQ ID NO: 44, SEQ ID NO: 45, SEQ ID NO: 46, or variant thereof.

Clause 3. The DNA targeting system of clause 2, wherein the at least one gRNA comprises a polynucleotide sequence corresponding to at least one of SEQ ID NO: 43, SEQ ID NO: 44, SEQ ID NO: 45, SEQ ID NO: 46, or variant thereof.

Clause 4. A DNA targeting system that binds to a gene encoding a ZNF274 protein, the DNA targeting system comprising at least one gRNA that binds and targets a polynucleotide sequence comprising a nucleotide sequence corresponding to at least one of SEQ ID NO: 13, SEQ ID NO: 14, SEQ ID NO: 16, SEQ ID NO: 17, SEQ ID NO: 47, SEQ ID NO: 48, or variant thereof.

Clause 5. The DNA targeting system of clause 4, wherein the at least one gRNA comprises a polynucleotide sequence corresponding to at least one of SEQ ID NO: 13, SEQ ID NO: 14, SEQ ID NO: 47, SEQ ID NO: 48, or variant thereof.

Clause 6. The DNA targeting system of any one of clauses 2-5, further comprising a Clustered Regularly Interspaced Short Palindromic Repeats associated (Cas) protein.

Clause 7. The DNA targeting system of clause 6, wherein the Cas protein comprises a *Streptococcus pyogenes* Cas9 molecule, or variant thereof.

Clause 8. The DNA targeting system of clause 7, wherein the Cas protein comprises a VQR variant of the *S. pyogenes* Cas9 molecule.

Clause 9. The DNA targeting system of clause 6, wherein the Cas protein comprises a Cas9 that recognizes a Protospacer Adjacent Motif (PAM) of NGG (SEQ ID NO: 2), NGA (SEQ ID NO: 3), NGAN (SEQ ID NO: 49) or NGNG (SEQ ID NO: 50).

Clause 10. An isolated polynucleotide sequence comprising the gRNA molecule of clause 1.

Clause 11. An isolated polynucleotide sequence encoding the DNA targeting system of any one of clauses 2-9.

Clause 12. A vector comprising the isolated polynucleotide sequence of clause 10 or 11.

Clause 13. A vector encoding the gRNA molecule of clause 1 and a Clustered Regularly Interspaced Short Palindromic Repeats associated (Cas) protein.

Clause 14. The vector of clause 13, wherein the Cas protein comprises a *Streptococcus pyogenes* Cas9 molecule, or variant thereof.

Clause 15. The vector of clause 14, wherein the Cas protein comprises a VQR variant of the *S. pyogenes* Cas9 molecule.

Clause 16. A cell comprising the gRNA of clause 1, the DNA targeting system of any one of clauses 2-9, the isolated polynucleotide sequence of clause 10 or 11, or the vector of any one of clauses 12-15, or a combination thereof.

Clause 17. The cell of clause 16, wherein the cell is an Induced Pluripotent Stem Cell (iPSC) from a Prader-Willi syndrome (PWS) patient.

Clause 18. The cell of clause 17, wherein the iPSC is a PWS1-7 large deletion cell line or UPD 1-2 cell line.

Clause 19. A kit comprising the gRNA of clause 1, the DNA targeting system of any one of clauses 2-9, the isolated polynucleotide sequence of clause 10 or 11, or the vector of any one of clauses 12-15, or the cell of any one of clauses 16-18, or a combination thereof.

Clause 20. A pharmaceutical composition comprising the gRNA of clause 1, the DNA targeting system of any one of clauses 2-9, the isolated polynucleotide sequence of clause 10 or 11, or the vector of any one of clauses 12-15, or the cell of any one of clauses 16-18, or a combination thereof.

Clause 21. A method for treating a disorder of genomic imprinting in a subject, the method comprising: modifying a zinc-finger protein 274 (ZNF274) binding site on maternal chromosome 15 at position 15q11-q13 of the subject, such that the binding of a ZNF274 protein to the ZNF274 binding site is reduced relative to a control, wherein the ZNF274 binding site comprises a polynucleotide having at least 90% sequence identity to SEQ ID NO: 1 or SEQ ID NO: 42.

Clause 22. The method of clause 21, wherein binding of the ZNF274 protein to the ZNF274 binding site is reduced by at least 90% relative to a control.

Clause 23. The method of clause 21, wherein binding of the ZNF274 protein to the ZNF274 binding site is eliminated.

Clause 24. The method of any one of clauses 21-23, wherein the maternal chromosome 15 at position 15q11-q13 of the subject is silenced prior to modification of the ZNF274 binding site.

Clause 25. The method of any one of clauses 21-24, wherein the disorder comprises Prader-Will syndrome (PWS).

Clause 26. The method of any one of clauses 21-25, wherein the ZNF274 binding site is modified by fully deleting the ZNF274 binding site, partially deleting the ZNF274 binding site, mutating one or more nucleotides of the ZNF274 binding site, cutting the ZNF274 binding site at one or more nucleotide positions, or a combination thereof.

Clause 27. The method of any one of clauses 21-26, wherein the ZNF274 binding site is modified by administering to the subject or a cell of the subject a DNA targeting system that binds to the ZNF274 binding site, wherein the DNA targeting system comprises at least one gRNA that binds and targets a polynucleotide sequence corresponding to SEQ ID NO: 1, SEQ ID NO: 42, or variant thereof.

Clause 28. The method of any one of clauses 21-26, wherein the ZNF274 binding site is modified by administering an isolated polynucleotide encoding a DNA targeting system that binds to the ZNF274 binding site, the DNA targeting system comprising at least one gRNA that binds and targets a polynucleotide sequence corresponding to SEQ ID NO: 1, SEQ ID NO: 42, or variant thereof.

Clause 29. The method of clause 27 or 28, wherein the DNA targeting system comprises at least one gRNA that binds and targets a polynucleotide sequence comprising a nucleotide sequence corresponding to at least one of SEQ ID NO: 1, SEQ ID NO: 42, SEQ ID NO: 43, SEQ ID NO: 44, SEQ ID NO: 45, SEQ ID NO: 46, or variant thereof.

Clause 30. The method of any one clauses 27-29, wherein the at least one gRNA comprises a polynucleotide sequence corresponding to at least one of SEQ ID NO: 43, SEQ ID NO: 44, SEQ ID NO: 45, SEQ ID NO: 46, or variant thereof.

Clause 31. The method of any one clauses 27-30, wherein the DNA targeting system further comprises a Clustered Regularly Interspaced Short Palindromic Repeats associated (Cas) protein.

Clause 32. A method for treating a disorder of genomic imprinting in a subject, the method comprising: administering to the subject a pharmaceutically effective amount of an agent that reduces the interaction of a ZNF274 protein with a ZNF274 binding site on maternal chromosome 15 at position 15q11-q13 of the subject relative to a control, wherein the ZNF274 binding site comprises a polynucleotide having at least 90% sequence identity to SEQ ID NO: 1 or SEQ ID NO: 42.

Clause 33. The method of clause 32, wherein the agent comprises a sequence-specific nuclease, or a polynucleotide sequence encoding a sequence-specific nuclease.

Clause 34. The method of clause 33, wherein the sequence-specific nuclease comprises a zinc finger nuclease, a TAL effector nuclease, or a CRISPR/Cas9 DNA targeting system.

Clause 35. The method of clause 34, wherein the CRISPR/Cas9 DNA targeting system binds to the ZNF274 binding site and comprises at least one gRNA that binds and targets a polynucleotide sequence comprising a nucleotide sequence corresponding to at least one of SEQ ID NO: 1, SEQ ID NO: 42, SEQ ID NO: 43, SEQ ID NO: 44, SEQ ID NO: 45, SEQ ID NO: 46, or variant thereof.

Clause 36. The method of clause 34 or 35, wherein the at least one gRNA comprises a polynucleotide sequence corresponding to at least one of SEQ ID NO: 43, SEQ ID NO: 44, SEQ ID NO: 45, SEQ ID NO: 46, or variant thereof.

Clause 37. The method of any one of clauses 34-36, wherein the CRISPR/Cas9 DNA targeting system further comprises a Clustered Regularly Interspaced Short Palindromic Repeats associated (Cas) protein.

Clause 38. The method of clause 37, wherein the Cas protein comprises a Cas9.

Clause 39. The method of clause 37 or 38, wherein the Cas protein comprises a *Streptococcus pyogenes* Cas9 molecule, or variant thereof.

Clause 40. The method of clause 39, wherein the Cas protein comprises a VQR variant of the *S. pyogenes* Cas9 molecule.

Clause 41. The method of any one of clauses 21-40 where the expression of at least one gene within 15q11-q13 is increased.

Clause 42. The method of any one of clauses 21-40, where the expression of at least one gene within the Prader-Will Syndrome critical region (PWSCR) of 15q11-q13 is increased.

Clause 43. The method of any one of clauses 21-40, wherein the expression of at least one RNA transcript selected from the genome coordinates hg19 chr15:25,012,961-25,685,253 or chr15:23,695,603-25,026,558 is increased.

Clause 44. The method of any one of clauses 21-40, wherein the expression of at least one RNA transcript selected from SNORD116, IPW, SNORD115, SNHG14, UBE3A-ATS, or a combination thereof, is increased.

Clause 45. The method of any one of clauses 21-40, wherein the expression of at least one of SNRPN exon 2, SNRPN exon 3, SNRPN exon 4, UBE3A, MAGEL2, MKRN3, SNRPN exon U4, NDN, or a combination thereof, is increased.

Clause 46. The method of any one of clauses 21-40, wherein the initiation of transcription from the SNRPN ULA promoter, the SNRPN U1B promoter, or a combination thereof, is increased.

Clause 47. The method of any one of clauses 21-40, wherein the binding of H3K9me3 is reduced.

Clause 48. A formulation for treating a disorder of genomic imprinting in a subject, the formulation comprising an agent that reduces relative to a control the binding of a ZNF274 protein to a ZNF274 binding site on a maternal nucleotide sequence, the ZNF274 binding site comprising a polynucleotide having at least 90% sequence identity to SEQ ID NO: 1 or SEQ ID NO: 42.

Clause 49. The formulation of clause 48, wherein the disorder is Prader-Will syndrome (PWS).

Clause 50. The formulation of clause 48, where the agent activates expression of at least one gene within 15q11-q13.

Clause 51. The formulation of clause 48, where the agent activates expression of at least one gene within the Prader-Will Syndrome critical region (PWSCR) of 15q11-q13.

Clause 52. The formulation of clause 45, wherein the agent activates the expression of at least one RNA transcript selected from the genome coordinates hg19 chr15:25,012,961-25,685,253 or chr15:23,695,603-25,026,558 is increased.

Clause 53. The formulation of clause 48, wherein the agent activates expression of at least one RNA transcript selected from SNORD116, IPW, SNORD115, SNHG14, UBE3A-ATS, or a combination thereof.

Clause 54. The formulation of clause 48, wherein the agent activates expression of at least one of SNRPN exon 2, SNRPN exon 3, SNRPN exon 4, UBE3A, MAGEL2, MKRN3, SNRPN exon U4, NDN, or a combination thereof.

Clause 55. The formulation of clause 48, wherein the agent activates the initiation of transcription from the SNRPN U1A promoter, the SNRPN U1B promoter, or a combination thereof.

Clause 56. The formulation of clause 48, wherein the agent reduces the binding of H3K9me3.

Clause 57. The method of any one of clauses 21-47 or the formulation of any one of clauses 48-56 wherein the control comprises a ZNF274 binding site that has not been modified.

We claim:

1. A DNA targeting system that binds to a ZNF274 binding site, the DNA targeting system comprising at least one gRNA that binds and targets a polynucleotide sequence comprising a nucleotide sequence corresponding to at least one of SEQ ID NO: 1, SEQ ID NO: 42, SEQ ID NO: 43, SEQ ID NO: 44, SEQ ID NO: 45, SEQ ID NO: 46; and
 a Clustered Regularly Interspaced Short Palindromic Repeats associated (Cas) protein.

2. A DNA targeting system that binds to a gene encoding a ZNF274 protein, the DNA targeting system comprising at least one gRNA that binds and targets a polynucleotide sequence comprising a nucleotide sequence corresponding to at least one of SEQ ID NO: 13, SEQ ID NO: 16, SEQ ID NO: 17, SEQ ID NO: 47, SEQ ID NO: 48; and
 a Clustered Regularly Interspaced Short Palindromic Repeats associated (Cas) protein.

3. An isolated polynucleotide sequence encoding the DNA targeting system of claim 1.

4. A formulation for treating a disorder of genomic imprinting in a subject, the formulation comprising an agent that reduces relative to a control the binding of a ZNF274 protein to a ZNF274 binding site on a maternal nucleotide sequence, wherein the agent is a DNA targeting system comprising at least one gRNA that binds and targets a polynucleotide sequence comprising a nucleotide sequence corresponding to at least one of SEQ ID NO: 1, SEQ ID NO: 42, SEQ ID NO: 43, SEQ ID NO: 44, SEQ ID NO: 45, SEQ ID NO: 46; and a Clustered Regularly Interspaced Short Palindromic Repeats associated (Cas) protein.

5. The formulation of claim 4, wherein the disorder is Prader-Will syndrome (PWS).

6. The formulation of claim 4, where the agent activates expression of at least one gene within 15q11-q13, or
 wherein the agent activates expression of at least one gene within the Prader-Will Syndrome critical region (PWSCR) of 15q11-q13, or
 wherein the agent activates the expression of at least one RNA transcript selected from the genome coordinates hg19 chr15:25,012,961-25,685,253 or chr15:23,695,603-25,026,558 is increased, or
 wherein the agent activates expression of at least one RNA transcript selected from SNORD116, IPW, SNORD115, SNHG14, UBE3A-ATS, or a combination thereof, or
 wherein the agent activates expression of at least one of SNRPN exon 2, SNRPN exon 3, SNRPN exon 4, UBE3A, MAGEL2, MKRN3, SNRPN exon U4, NDN, or a combination thereof, or
 wherein the agent activates the initiation of transcription from the SNRPN U1A promoter, the SNRPN U1B promoter, or a combination thereof, or
 wherein the agent reduces the binding of H3K9me3.

* * * * *

```
                        SEQUENCE LISTING

<160> NUMBER OF SEQ ID NOS: 50

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
tgagtgagaa ctcatacc                                                    18

<210> SEQ ID NO 2
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 2 ngg                                                                     3

<210> SEQ ID NO 3
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 3 nga                                                                     3

<210> SEQ ID NO 4
<211> LENGTH: 48
<212> TYPE: DNA
<213> ORGANISM: Artificial Sequence
<220> FEATURE:
<223> OTHER INFORMATION: Synthetic

<400> SEQUENCE: 4
aaaaacattc cttggaaaag ctgaacaaaa tgagtgagaa ctcataac                    48
```

```
<210> SEQ ID NO 5
<211> LENGTH: 48
<212> TYPE: DNA
<213> ORGANISM: Artificial Sequence
<220> FEATURE:
<223> OTHER INFORMATION: Synthetic

<400> SEQUENCE: 5
aaaaacattc cttggaaaag ctgaacaaaa tgagtgaaaa ctcatacc            48

<210> SEQ ID NO 6
<211> LENGTH: 48
<212> TYPE: DNA
<213> ORGANISM: Artificial Sequence
<220> FEATURE:
<223> OTHER INFORMATION: Synthetic

<400> SEQUENCE: 6
aaaaacattc cttggaaaag ctgaacaaaa tgagtgagaa ctcatacc            48

<210> SEQ ID NO 7
<211> LENGTH: 48
<212> TYPE: DNA
<213> ORGANISM: Artificial Sequence
<220> FEATURE:
<223> OTHER INFORMATION: Synthetic

<400> SEQUENCE: 7
aaaaacattc cttggaaaag ctgaacaaaa tgagtgaaaa ctcatacc            48

<210> SEQ ID NO 8
<211> LENGTH: 48
<212> TYPE: DNA
<213> ORGANISM: Artificial Sequence
<220> FEATURE:
<223> OTHER INFORMATION: Synthetic

<400> SEQUENCE: 8
aaaaacattc cttggaaaag ctgaacaaaa tgagtgagaa ctcatacc            48

<210> SEQ ID NO 9
<211> LENGTH: 48
<212> TYPE: DNA
<213> ORGANISM: Artificial Sequence
<220> FEATURE:
<223> OTHER INFORMATION: Synthetic

<400> SEQUENCE: 9
aaaaacattc cttggaaaag ctgaacaaaa tgagtgaaaa ctcatacc            48

<210> SEQ ID NO 10
<211> LENGTH: 48
<212> TYPE: DNA
<213> ORGANISM: Artificial Sequence
<220> FEATURE:
<223> OTHER INFORMATION: Synthetic

<400> SEQUENCE: 10
aaaaacattc cttggaaaag ctgaacaaaa tgagtgagaa ctcatacc            48

<210> SEQ ID NO 11
<211> LENGTH: 48
<212> TYPE: DNA
<213> ORGANISM: Artificial Sequence
<220> FEATURE:
<223> OTHER INFORMATION: Synthetic
```

<400> SEQUENCE: 11
aaaaacattc cttggaaaag ctgaacaaaa tgagtgagaa ctcatacc        48

<210> SEQ ID NO 12
<211> LENGTH: 48
<212> TYPE: DNA
<213> ORGANISM: Artificial Sequence
<220> FEATURE:
<223> OTHER INFORMATION: Synthetic

<400> SEQUENCE: 12
aaaaacattc cttggaaaag ctgaacaaaa tgagtgagaa ctcatacc        48

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cctccaggct tccgacggcc        20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
cctgcaggac aacctgccga        20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
cagtcgggcg tcatcatgat        20

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
cctccaggct tccgacggcc tgg        23

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
cctgcaggac aacctgccga ggg        23

<210> SEQ ID NO 18

```
<211> LENGTH: 23
<212> TYPE: DNA
<213> ORGANISM: Artificial Sequence
<220> FEATURE:
<223> OTHER INFORMATION: Synthetic

<400> SEQUENCE: 18
cctgcaggcc tcggacggcc agg                                              23

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
cacccaggcc cccgacggcc agg                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
gctcaagtct tccgaccgcc aag                                              23

<210> SEQ ID NO 21
<211> LENGTH: 23
<212> TYPE: DNA
<213> ORGANISM: Artificial Sequence
<220> FEATURE:
<223> OTHER INFORMATION: Synthetic

<400> SEQUENCE: 21
gccccaggcc tccgactgcc gag                                              23

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
ccgcgaggct tccgagggcc agg                                              23

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
tgggcaggaa aacctgccga ggg                                              23

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
```
cctggaggag aacctgccgt gag                                           23

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
cctcaaggac aacctgccca tag                                           23

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
ccagcaggtc aacctgacga tgg                                           23

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
ccaccaggaa accctgccga aag                                           23

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
gagtgaggga caacttccac tga                                           23

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
aactgaggtc cagcacattg cc                                            22

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
tcttcaaatg tgcttggatc ga                                            22

<210> SEQ ID NO 31
<211> LENGTH: 19
<212> TYPE: DNA

```
<213> ORGANISM: Artificial Sequence
<220> FEATURE:
<223> OTHER INFORMATION: Synthetic

<400> SEQUENCE: 31
tgcctcttcg aacgtgctt                                                  19

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
ggcatccaca ggccaaagt                                                  19

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
tgagggtgtc tttgggattc c                                               21

<210> SEQ ID NO 34
<211> LENGTH: 22
<212> TYPE: DNA
<213> ORGANISM: Artificial Sequence
<220> FEATURE:
<223> OTHER INFORMATION: Synthetic

<400> SEQUENCE: 34
atctgtctga ggagcggtca gt                                              22

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tcccacccat gtacctcaca                                                 20

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
gtgcctgtga tgtgagactt tca                                             23

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
gcaacgtgct ggacctcagt                                                 20
```

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
cgtgctggac ctcagttctg                                       20

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
ccatggctgc cacaccata                                        19

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
agctgtgcca ctgagcaaaa                                       20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
tccccaggct gtctcttgag                                       20

<210> SEQ ID NO 42
<211> LENGTH: 59
<212> TYPE: DNA
<213> ORGANISM: Artificial Sequence
<220> FEATURE:
<223> OTHER INFORMATION: Synthetic

<400> SEQUENCE: 42
cttggaaaag ctgaacaaaa tgagtgagaa ctcataccgt cgttctcatc agaactgag    59

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gaaaagctga acaaaatgag                                       20

<210> SEQ ID NO 44
<211> LENGTH: 20
<212> TYPE: DNA
<213> ORGANISM: Artificial Sequence
<220> FEATURE:

<223> OTHER INFORMATION: Synthetic

<400> SEQUENCE: 44
ctcagttccg atgagaacga                                                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
gccactctca ttcagcacgt                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
gcagatttca tatgtaccac                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
ctgcggttcc accatcacgc                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
agcagcctta ggtccggtga                                                    20

<210> SEQ ID NO 49
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 49 ngan                                                                      4

<210> SEQ ID NO 50
<211> LENGTH: 4
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t

<400> SEQUENCE: 50 ngng                                                                  4
```